United States Patent
Kuboyama et al.

(10) Patent No.: US 10,342,758 B2
(45) Date of Patent: Jul. 9, 2019

(54) CATIONIC LIPID

(71) Applicant: Kyowa Hakko Kirin Co., Ltd., Tokyo (JP)

(72) Inventors: Takeshi Kuboyama, Tokyo (JP); Tomohiro Era, Tokyo (JP); Tomoyuki Naoi, Tokyo (JP); Kaori Yagi, Tokyo (JP); Shintaro Hosoe, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 14/412,069

(22) PCT Filed: Jul. 8, 2013

(86) PCT No.: PCT/JP2013/068682
§ 371 (c)(1),
(2) Date: Dec. 30, 2014

(87) PCT Pub. No.: WO2014/007398
PCT Pub. Date: Jan. 9, 2014

(65) Prior Publication Data
US 2015/0174261 A1    Jun. 25, 2015

Related U.S. Application Data

(60) Provisional application No. 61/789,466, filed on Mar. 15, 2013.

(30) Foreign Application Priority Data

Jul. 6, 2012 (JP) .................................. 2012-152423
Apr. 25, 2013 (JP) .................................. 2013-092327

(51) Int. Cl.

| | | |
|---|---|---|
| A61K 9/00 | (2006.01) | |
| A61K 9/51 | (2006.01) | |
| A61K 47/16 | (2006.01) | |
| A61K 47/54 | (2017.01) | |
| C12N 15/11 | (2006.01) | |
| C12N 15/88 | (2006.01) | |
| A61K 31/713 | (2006.01) | |
| C07C 211/21 | (2006.01) | |
| C07C 215/08 | (2006.01) | |
| C07C 215/10 | (2006.01) | |
| C07C 217/08 | (2006.01) | |

(Continued)

(52) U.S. Cl.
CPC .................. *A61K 9/00* (2013.01); *A61K 9/51* (2013.01); *A61K 31/713* (2013.01); *A61K 47/16* (2013.01); *A61K 47/54* (2017.08); *C07C 211/21* (2013.01); *C07C 215/08* (2013.01); *C07C 215/10* (2013.01); *C07C 217/08* (2013.01); *C07C 229/12* (2013.01); *C07C 237/06* (2013.01); *C07C 271/12* (2013.01); *C07C 271/16* (2013.01); *C07D 207/06* (2013.01); *C07D 207/08* (2013.01); *C07D 207/09* (2013.01); *C07D 211/06* (2013.01); *C07D 211/22* (2013.01); *C12N 15/11* (2013.01); *C12N 15/88* (2013.01); *A61K 31/7088* (2013.01)

(58) Field of Classification Search
None
See application file for complete search history.

(56) References Cited

U.S. PATENT DOCUMENTS 2,782,184 A  2/1957 Husted et al.
2,899,426 A  8/1959 Bloom
(Continued)

FOREIGN PATENT DOCUMENTS

DE    25 07 007    9/1975
EP    0 407 124    1/1991
(Continued)

OTHER PUBLICATIONS

Kumar et al, (J Adv Oral Research, 3 (2), May 2012).*
Gupta et al (Int J Pharm Bio Sci, 7(2), 630-637, Apr. 2016).*
International Search Report dated Aug. 20, 2013 in International (PCT) Application No. PCT/JP2013/068682.
Examination report No. 3 for standard patent application dated Jan. 12, 2018 in Australian Application No. 2013285842.
CAS Registry No. 1340261-27-9; STN Entry Date Nov. 3, 2011.
CAS Registry No. 1339884-41-1; STN Entry Date Nov. 2, 2011.
CAS Registry No. 1342347-10-7; STN Entry Date Nov. 8, 2011.
CAS Registry No. 1343698-31-6; STN Entry Date Nov. 10, 2011.
(Continued)

*Primary Examiner* — Celeste A Roney
(74) *Attorney, Agent, or Firm* — Wenderoth, Lind & Ponack, L.L.P

(57) ABSTRACT

Provided are a cationic lipid which facilitates the introduction of a nucleic acid into, for example, a cell or the like; a composition containing the cationic lipid and a nucleic acid; a method for introducing a nucleic acid into a cell by using a composition containing the cationic lipid and the nucleic acid; and the like. The cationic lipid is, for example, a cationic lipid represented by formula (A): formula (A):

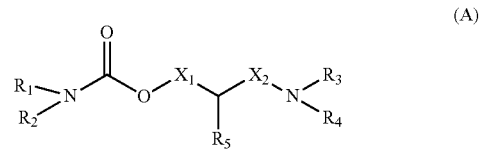

(A)

(wherein $R^1$ is alkenyl or the like, $R^2$ is alkenyl or the like, $R^3$ and $R^4$ are each alkyl, or are combined together to form alkylene, or $R^3$ and $R^5$ are combined together to form alkylene, $R^5$ is a hydrogen atom or the like, or is combined together with $R^3$ to form alkylene, $X^1$ is alkylene, and $X^2$ is a single bond or alkylene).

12 Claims, 9 Drawing Sheets

Specification includes a Sequence Listing.

(51) Int. Cl.

| | | |
|---|---|---|
| C07C 229/12 | (2006.01) | |
| C07C 237/06 | (2006.01) | |
| C07C 271/12 | (2006.01) | |
| C07C 271/16 | (2006.01) | |
| C07D 207/06 | (2006.01) | |
| C07D 207/08 | (2006.01) | |
| C07D 207/09 | (2006.01) | |
| C07D 211/06 | (2006.01) | |
| C07D 211/22 | (2006.01) | |
| A61K 31/7088 | (2006.01) | |

(56) References Cited

U.S. PATENT DOCUMENTS

| | | | |
|---|---|---|---|
| 3,808,339 | A | 4/1974 | Bordenca |
| 3,872,171 | A | 3/1975 | Cronin et al. |
| 4,021,572 | A | 5/1977 | Van Scott et al. |
| 4,034,040 | A | 7/1977 | Cronin et al. |
| 4,087,552 | A | 5/1978 | Cronin et al. |
| 4,139,560 | A | 2/1979 | Reinehr et al. |
| 4,144,320 | A | 3/1979 | Hernestam et al. |
| 4,258,061 | A | 3/1981 | Cronin et al. |
| 4,357,476 | A | 11/1982 | Reinchr et al. |
| 4,491,583 | A | 1/1985 | Cronin et al. |
| 5,753,613 | A | 5/1998 | Ansell et al. |
| 6,333,433 | B1 | 12/2001 | Banerjee et al. |
| 6,395,713 | B1 | 5/2002 | Beigelman et al. |
| 8,557,875 | B2 | 10/2013 | Kono |
| 2007/0213257 | A1* | 9/2007 | Sweedler ............... A61K 38/10 536/24.5 |
| 2008/0274116 | A1 | 11/2008 | Keil et al. |
| 2009/0163372 | A1 | 6/2009 | Rosemeyer |
| 2009/0234271 | A1 | 9/2009 | Kajimoto et al. |
| 2011/0009641 | A1 | 1/2011 | Anderson et al. |
| 2011/0294871 | A1 | 12/2011 | Keil et al. |
| 2012/0053233 | A1 | 3/2012 | Kono |
| 2012/0065138 | A1 | 3/2012 | Keil et al. |
| 2013/0165381 | A1 | 6/2013 | Keil et al. |
| 2013/0245126 | A1 | 9/2013 | Serizawa |
| 2013/0273138 | A1 | 10/2013 | Serizawa |
| 2013/0296323 | A1 | 11/2013 | Serizawa et al. |
| 2014/0039032 | A1 | 2/2014 | Kuboyama et al. |
| 2014/0045913 | A1 | 2/2014 | Kuboyama et al. |
| 2014/0171516 | A1 | 6/2014 | Serizawa |
| 2014/0187646 | A1 | 7/2014 | Serizawa |
| 2014/0194527 | A1 | 7/2014 | Serizawa |
| 2014/0275091 | A1 | 9/2014 | Serizawa et al. |
| 2014/0329885 | A1 | 12/2014 | Keil et al. |
| 2015/0025077 | A1 | 1/2015 | Serizawa et al. |
| 2015/0359906 | A1 | 12/2015 | Keil et al. |
| 2016/0304487 | A1 | 10/2016 | Kuboyama et al. |
| 2017/0036990 | A1 | 2/2017 | Keil et al. |

FOREIGN PATENT DOCUMENTS

| | | |
|---|---|---|
| EP | 1 492 876 | 12/2007 |
| FR | 2 358 884 | 2/1978 |
| JP | 47-4599 | 3/1972 |
| JP | 49-011256 | 3/1974 |
| JP | 49-100011 | 9/1974 |
| JP | 53-088850 | 8/1978 |
| JP | 61-209245 | 9/1986 |
| JP | 10-509418 | 9/1998 |
| JP | 2005-532278 | 10/2005 |
| JP | 2007-536324 | 12/2007 |
| JP | 2009-501699 | 1/2009 |
| JP | 2009-203173 | 9/2009 |
| WO | 96/10390 | 4/1996 |
| WO | 99/05094 | 2/1999 |
| WO | 02/47620 | 6/2002 |
| WO | 03/080847 | 10/2003 |
| WO | 2004/039971 | 5/2004 |
| WO | 2006/069782 | 7/2006 |
| WO | 2006/138380 | 12/2006 |
| WO | 2009/108690 | 9/2009 |
| WO | 2010/042877 | 4/2010 |
| WO | 2010/054401 | 5/2010 |
| WO | 2010/128669 | 11/2010 |
| WO | 2011/136368 | 11/2011 |
| WO | 2013/016058 | 1/2013 |
| WO | 2013/089151 | 6/2013 |
| WO | 2013/089152 | 6/2013 |
| WO | 2013/130654 | 9/2013 |

OTHER PUBLICATIONS

CAS Registry No. 1343768-50-2; STN Entry Date Nov. 10, 2011.
Delaye, P-O. etc al., "Switching Regioselectivity in the Allylation of Imines by N-Side Chain Tuning", Organic Letters, 2012, vol. 14, No. 12, pp. 3004-3007 (Published online Jun. 5, 2012).
Sjöholm et al., "Investigation of the Lewis acid mediated stereoselective cyclization of cationic aminyl radicals leading to substituted pyrrolidines", Journal of the Chemical Society, Perkin Trans 1, 2001, pp. 891-899.
Bertolino et al., "Polyisoprenoid amphiphilic compounds as inhibitors of squalene synthesis and other microsomal enzymes", Biochimica et Biophysica Acta, Lipids and Lipid Metabolism, 1978, vol. 530, pp. 17-23.
International Preliminary Report on Patentability dated Jan. 6, 2015 in International (PCT) Application No. PCT/JP2013/068682.
Examination report No. 2 for standard patent application dated Aug. 11, 2017 in Australia Application No. 2013285842.
Mahidhar et al., "Distance of Hydroxyl Functionality from the Quaternized Center Influence DNA Binding and in Vitro Gene Delivery Efficacies of Cationic Lipids with Hydroxyalkyl Headgroups" Journal of Medicinal Chemistry, vol. 47, No. 23, 2004, pp. 5721-5728.
Taveira et al., "Preparation and antitubercular activities of alkylated amino alcohols and their glycosylated derivatives", Bioorganic & Medicinal Chemistry, vol. 15, 2007, pp. 7789-7794.
Singh et al., "Anchor Dependency for Non-Glycerol Based Cationic Lipofectins: Mixed Bag of Regular and Anomalous Transfection Profiles", Chemistry European Journal, vol. 8, No. 4, 2002, pp. 900-909.
Banerjee et al., "Novel Series of Non-Glycerol-Based Cationic Transfection Lipids for Use in Liposomal Gene Delivery", Journal of Medicinal Chemistry, vol. 42, 1999, pp. 4292-4299.
Li et al., "Combinatorial Synthesis and High-Throughput Screening of Alkyl Amines for Nonviral Gene Delivery", Bioconjugate Chemistry, vol. 24, 2013, pp. 1543-1551.
CAS Registry No. 19405-08-4; STN Entry Date Nov. 16, 1984.
CAS Registry No. 1309766-94-6; STN Entry Date Jun. 20, 2011.
CAS Registry No. 86337-01-1; STN Entry Date Nov. 16, 1984.
CAS Registry No. 959299-04-8; STN Entry Date Dec. 21, 2007.
CAS Registry No. 1026571-62-9; STN Date Jun. 8, 2008.
CAS Registry No. 1081825-59-3.
CAS Registry No. 1299407-84-3; STN Entry Date May 24, 2011.
CAS Registry No. 437718-61-1.
Donetti et al., "Secondary Amines From Cyanamides: A New Method for Removing the -CN Group," Tetrahedron Letters, No. 39, pp. 3327-3328, 1969.
Mahidhar et al., "Distance of Hydroxyl Functionality from the Quaternized Center Influence DNA Binding and in Vitro Gene Delivery Efficacies of Cationic Lipids with Hydroxyalkyl Headgroups", Journal of Medicinal Chemistry, vol. 47, pp. 5721-5728, 2004.
Taveira et al., "Preparation and antitubercular activities of alkylated amino alcohols and their glycosylated derivatives", Bioorganic & Medicinal Chemistry, vol. 15, pp. 7789-7794, 2007.
Groult et al., "Reaction of Aminoalcohols With Butadiene Catalysed by Palladium Complexes", Tetrahedron, vol. 39, No. 9, pp. 1543-1550, 1983.
Mantegani et al., "Terpene Compounds as Drugs. IV. Terpenyl Derivatives of Local Anesthetics", Journal of Medicinal Chemistry, vol. 11, No. 3, p. 637, 1968.
Abidi et al., "Determination of Isomeric Olefinic Groups in Unsaturated Terpene Aminoethanols by Carbon-13 Nuclear Magnetic Resonance Spectrometry", Analytical Chemistry, vol. 54, No. 3, pages 510-516, 1982.

(56) References Cited

OTHER PUBLICATIONS

Abidi et al., "Direct Conversion of Terpenylalkanolamines to Ethylidyne N-Nitroso Compounds", Journal of Organic Chemistry, vol. 51, pp. 2687-2694, 1986.
CAS Registry No. 87283-02-1; STN Entry Date Nov. 16, 1984.

* cited by examiner

[Fig. 1]
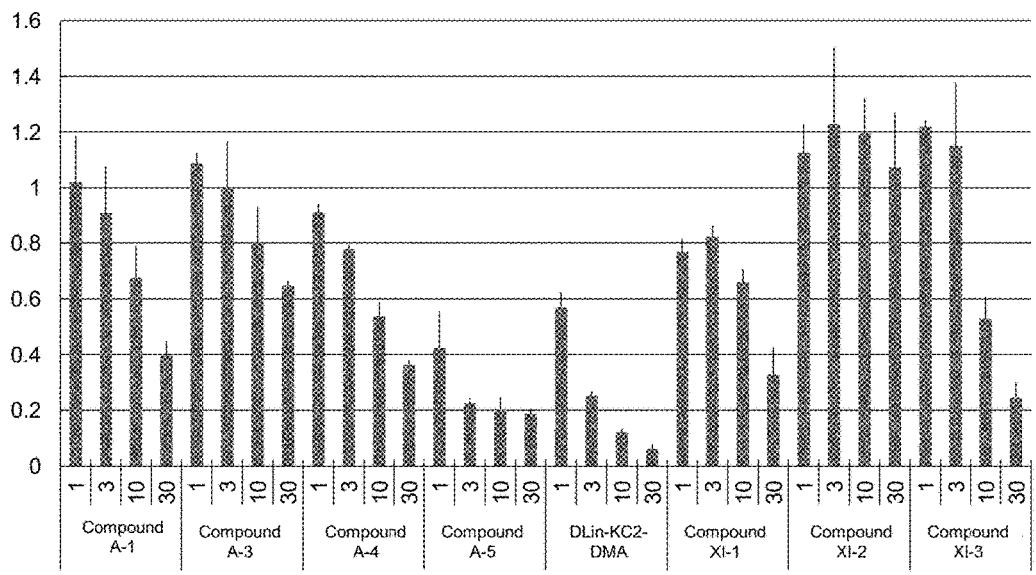
[Fig. 2]
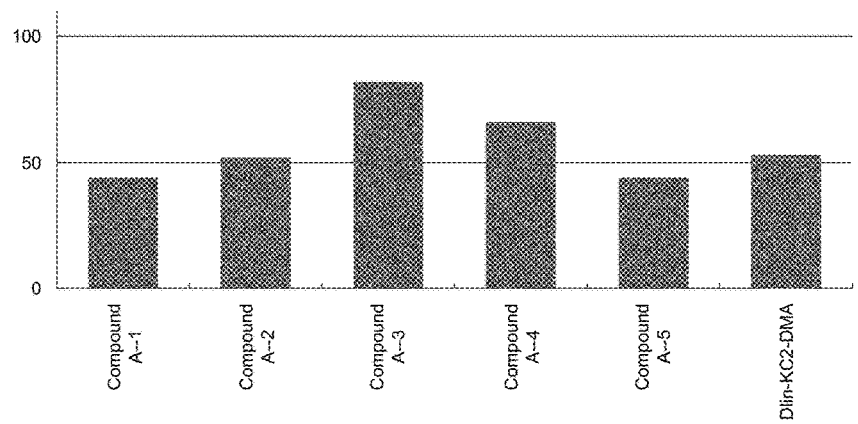

[Fig. 3]
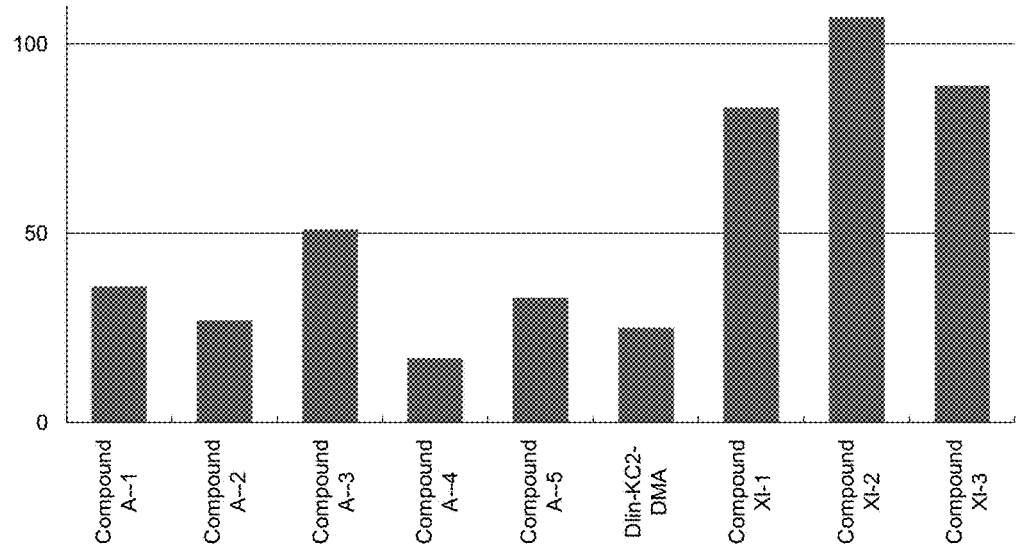
[Fig. 4]
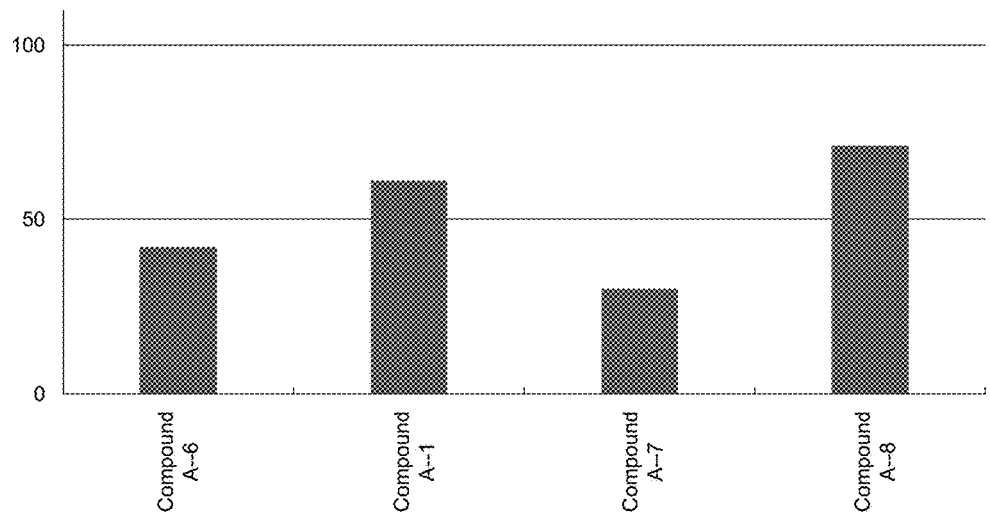

[Fig. 5]
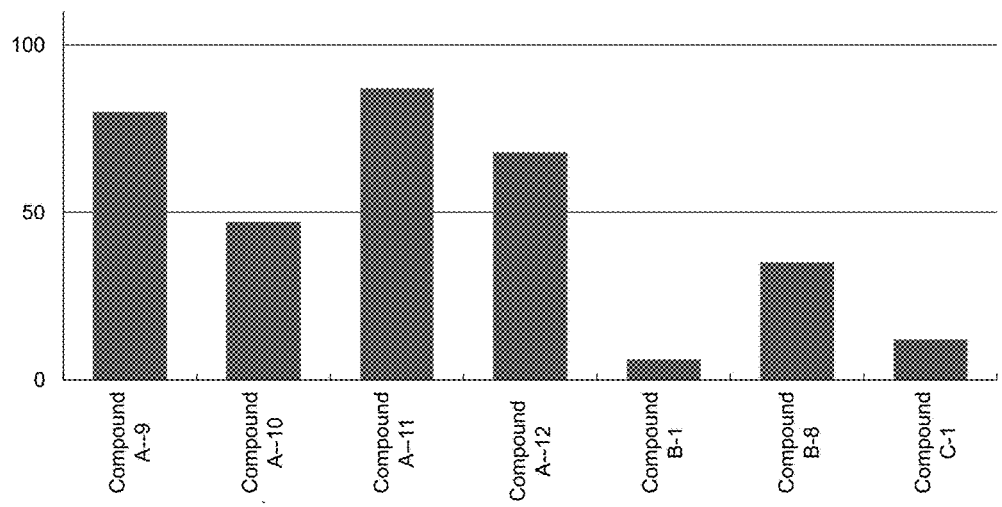
[Fig. 6]
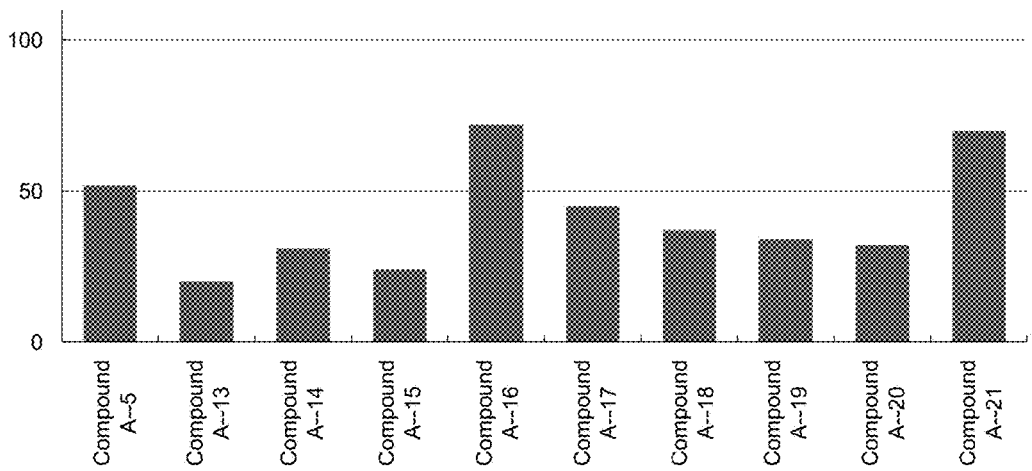

[Fig. 7]
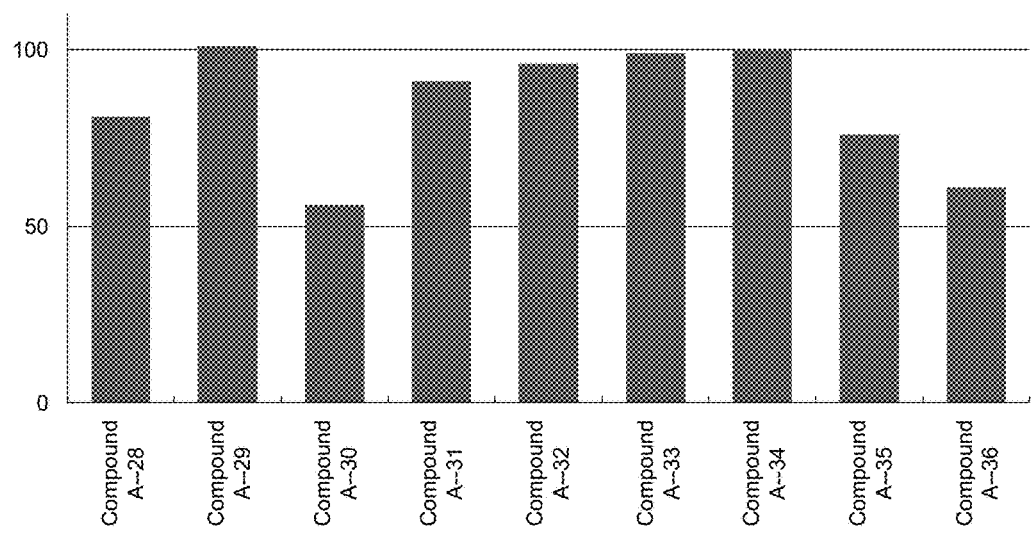

[Fig. 8]
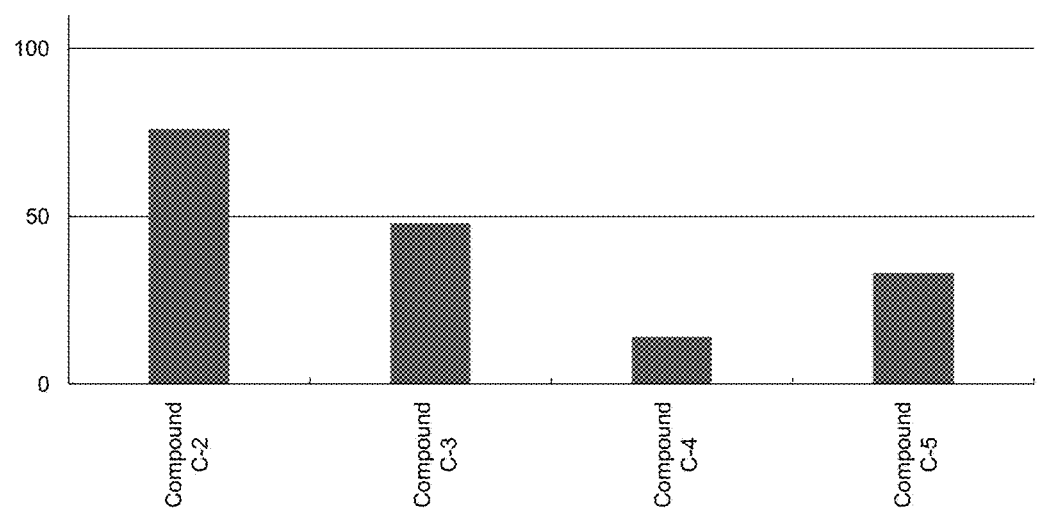

[Fig. 9]
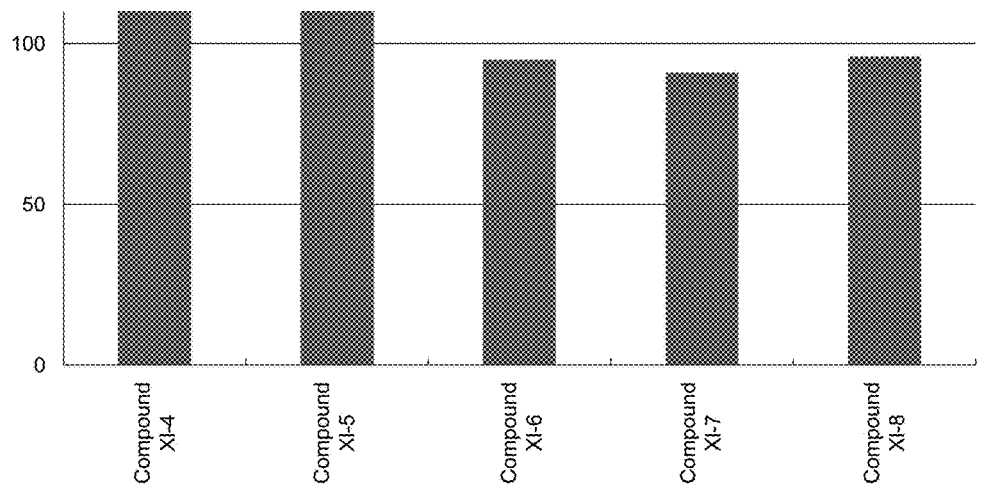
[Fig. 10]
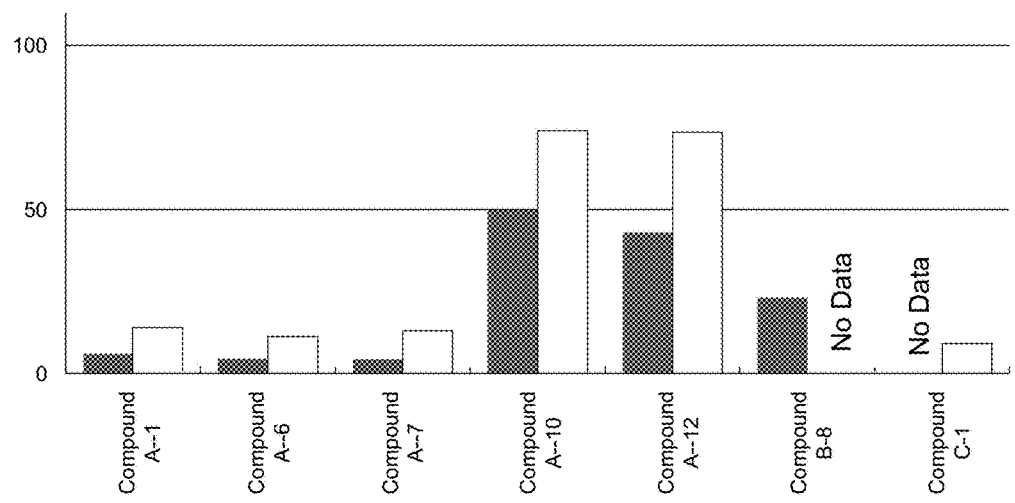

[Fig. 11]
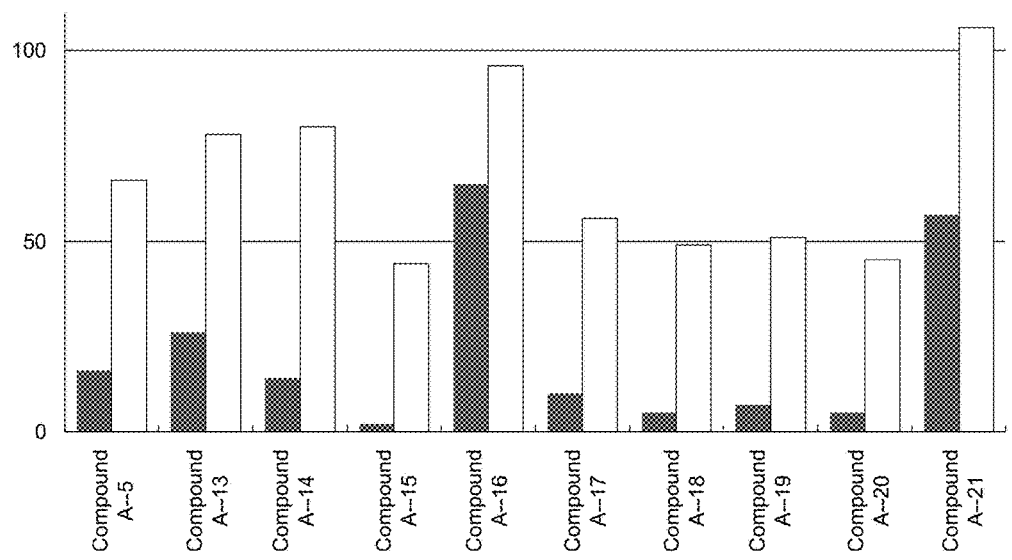

[Fig. 12]
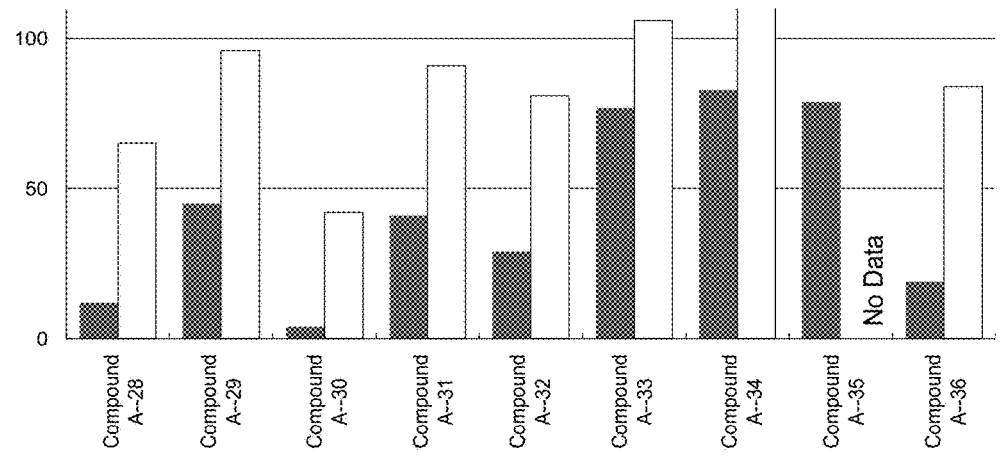
[Fig. 13]
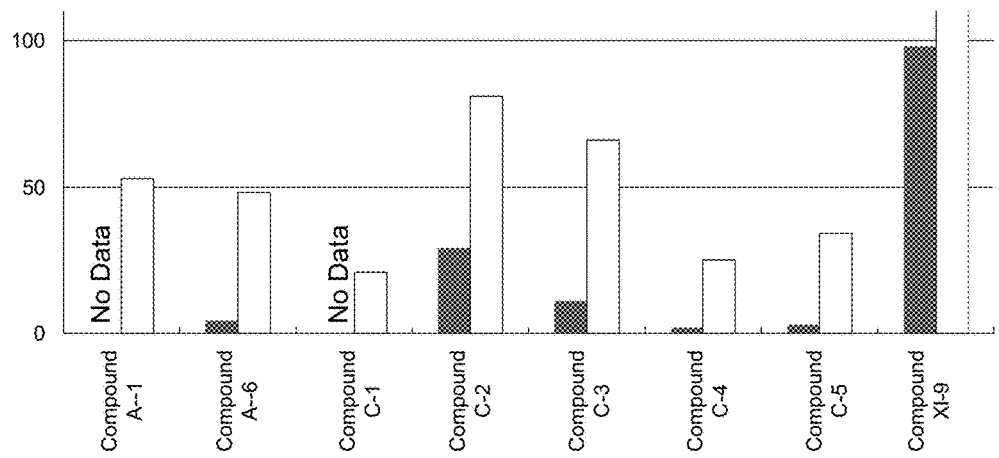

[Fig. 14]
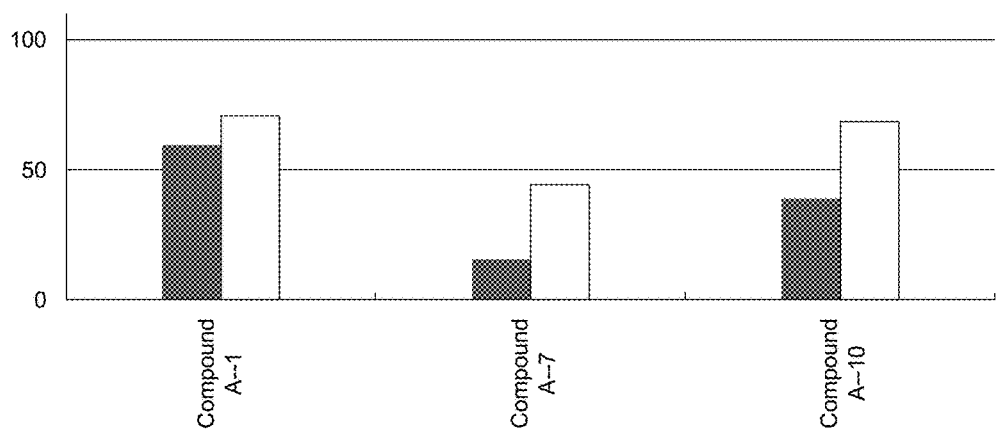

SEQUENCE LISTING

<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Apolipoprotein-B siRNA sense
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (21)..(21)
<223> OTHER INFORMATION: um

<400> SEQUENCE: 1
gucaucacac ugaauaccaa u                                              21

<210> SEQ ID NO 2
<211> LENGTH: 23
<212> TYPE: RNA
<213> ORGANISM: Artificial Sequence
<220> FEATURE:
<223> OTHER INFORMATION: Apolipoprotein-B siRNA antisense
<220> FEATURE:
<221> NAME/KEY: misc_feature
<222> LOCATION: (1)..(1)
<223> OTHER INFORMATION: 5'-phosphorylated Adenosine

<400> SEQUENCE: 2
auugguauuc agugugauga cac                                            23

<210> SEQ ID NO 3
<211> LENGTH: 21
<212> TYPE: DNA
<213> ORGANISM: Artificial Sequence
<220> FEATURE:
<223> OTHER INFORMATION: Coagulation Factor VII siRNA sense
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (4)..(4)
<223> OTHER INFORMATION: n = uracil
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (9)..(9)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature

```
<222> LOCATION: (16)..(17)
<223> OTHER INFORMATION: n = uracil
<220> FEATURE:
<221> NAME/KEY: modified_base
<222> LOCATION: (4)..(5)
<223> OTHER INFORMATION: 2'-fluoro
<220> FEATURE:
<221> NAME/KEY: modified_base
<222> LOCATION: (7)..(10)
<223> OTHER INFORMATION: 2'-fluoro
<220> FEATURE:
<221> NAME/KEY: modified_base
<222> LOCATION: (14)..(17)
<223> OTHER INFORMATION: 2'-fluoro
<220> FEATURE:
<221> NAME/KEY: modified_base
<222> LOCATION: (19)..(19)
<223> OTHER INFORMATION: 2'-fluoro
<220> FEATURE:
<221> NAME/KEY: misc_feature
<222> LOCATION: (21)..(21)
<223> OTHER INFORMATION: 5'-phosphorothioated Thymidine

<400> SEQUENCE: 3
ggancancnc aagncnnact t                                              21

<210> SEQ ID NO 4
<211> LENGTH: 21
<212> TYPE: DNA
<213> ORGANISM: Artificial Sequence
<220> FEATURE:
<223> OTHER INFORMATION: Coagulation Factor VII siRNA antisense
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (8)..(9)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (2)..(2)
<223> OTHER INFORMATION: 2'-fluoro
<220> FEATURE:
<221> NAME/KEY: modified_base
<222> LOCATION: (7)..(9)
<223> OTHER INFORMATION: 2'-fluoro
<220> FEATURE:
<221> NAME/KEY: modified_base
<222> LOCATION: (14)..(14)
<223> OTHER INFORMATION: 2'-fluoro
<220> FEATURE:
<221> NAME/KEY: modified_base
<222> LOCATION: (17)..(19)
<223> OTHER INFORMATION: 2'-fluoro
<220> FEATURE:
<221> NAME/KEY: misc_feature
<222> LOCATION: (21)..(21)
<223> OTHER INFORMATION: 5'-phosphorothioated Thymidine

<400> SEQUENCE: 4
gnaagacnng agangancct t                                              21
```

CATIONIC LIPID

TECHNICAL FIELD

The present invention relates to a cationic lipid which facilitates the introduction of a nucleic acid into, for example, a cell or the like; a composition containing the cationic lipid; and the like.

BACKGROUND ART

A cationic lipid is an amphiphilic molecule having a lipophilic region containing one or more hydrocarbon groups and a hydrophilic region containing at least one positively charged polar head group. The formation of a complex which is positively charged as a whole between a cationic lipid and a macromolecule such as a nucleic acid facilitates the entry of the macromolecule such as a nucleic acid into a cytoplasm through a cell plasma membrane, and therefore, the cationic lipid is useful. This process, which can be performed in vitro and in vivo, is known as transfection.

Patent Documents 1 and 2 disclose cationic lipids and lipid particles containing the lipid, which are advantageous for in vivo delivery of a nucleic acid into a cell and for use in a nucleic acid-lipid particle composition suitable for therapy of diseases. For example, Patent Document 1 discloses a cationic lipid such as

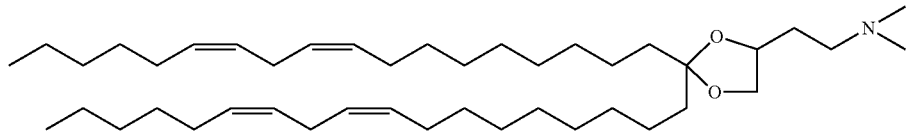 [SMILES: CCCCC/C=C\C/C=C\CCCCCCCCC1(CCCCCCCC/C=C\C/C=C\CCCCC)OCC(CCN(C)C)O1]

2,2-dilinoleyl-4-(2-dimethylaminoethyl)[1,3]-dioxolane (DLin-KC2-DMA); and for example, Patent Document 2 discloses a cationic lipid such as

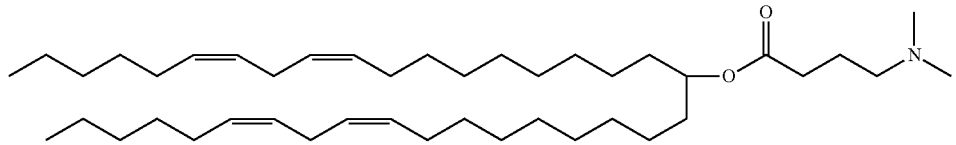 [SMILES: CCCCC/C=C\C/C=C\CCCCCCCCC(CCCCCCCC/C=C\C/C=C\CCCCC)OC(=O)CCCN(C)C]

(6Z,9Z,28Z,31Z)-heptatriaconta-6,9,28,31-tetraen-19-yl 4-(dimethylamino)butanoate (DLin-MC3-DMA).

PRIOR ART DOCUMENT

Patent Document

Patent Document 1: WO2010/042877
Patent Document 2: WO2010/054401

SUMMARY OF THE INVENTION

Problem to be Solved by the Invention

An object of the present invention is to provide a cationic lipid which facilitates the introduction of a nucleic acid into, for example, a cell or the like; a composition containing the cationic lipid; and the like.

Means for Solving the Problem

The present invention relates to the following (1) to (22).
(1) A cationic lipid represented by formula (A):

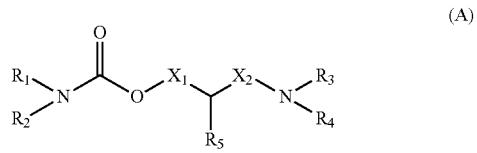

(wherein $R^1$ is linear or branched alkyl, alkenyl, or alkynyl, each having 8 to 24 carbon atoms, $R^2$ is linear or branched alkyl, alkenyl, or alkynyl, each having 8 to 24 carbon atoms, alkoxyethyl, alkoxypropyl, alkenyloxyethyl, alkenyloxypropyl, alkynyloxyethyl, or alkynyloxypropyl, $R^3$ and $R^4$ may be the same or different and are each alkyl having 1 to 3 carbon atoms, or are combined together to form alkylene having 2 to 8 carbon atoms, or $R^3$ and $R^5$ are combined together to form alkylene having 2 to 8 carbon atoms, $R^5$ is a hydrogen atom, alkyl having 1 to 6 carbon atoms, alkenyl having 3 to 6 carbon atoms, amino, monoalkylamino, hydroxy, alkoxy, carbamoyl, monoalkylcarbamoyl, dialkylcarbamoyl, or alkyl having 1 to 6 carbon atoms or alkenyl having 3 to 6 carbon atoms, each substituted with one to three of the same or different substituents selected from amino, monoalkylamino, hydroxy, alkoxy, carbamoyl, monoalkylcarbamoyl, and dialkylcarbamoyl, or is combined together with $R^3$ to form alkylene having 2 to 8 carbon atoms, $X^1$ is alkylene having 1 to 6 carbon atoms, and $X^2$ is a single bond or alkylene having 1 to 6 carbon atoms, provided that the sum of the number of carbon atoms in $X^1$ and $X^2$ is 7 or less, and when $R^5$ is a hydrogen atom, $X^2$ is a single bond, and when $R^5$ and $R^3$ are combined together to form alkylene having 2 to 6 carbon atoms, $X^2$ is a single bond, or methylene or ethylene), formula (B):

(wherein
R⁶ is linear or branched alkyl, alkenyl, or alkynyl, each having 8 to 24 carbon atoms, and
R⁷ is linear or branched alkyl, alkenyl, or alkynyl, each having 8 to 24 carbon atoms, alkoxyethyl, alkoxypropyl, alkenyloxyethyl, alkenyloxypropyl, alkynyloxyethyl, or alkynyloxypropyl), or
formula (C):

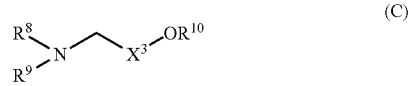

(wherein
R⁸ is linear or branched alkyl, alkenyl, or alkynyl, each having 8 to 24 carbon atoms,
R⁹ is linear or branched alkyl, alkenyl, or alkynyl, each having 8 to 24 carbon atoms, alkoxyethyl, alkoxypropyl, alkenyloxyethyl, alkenyloxypropyl, alkynyloxyethyl, or alkynyloxypropyl,
X³ is alkylene having 1 to 3 carbon atoms, and R¹⁰ is a hydrogen atom or alkyl having 1 to 3 carbon atoms).
(2) The cationic lipid according to the above (1), wherein R¹, R², R⁶, R⁷, R⁸, and R⁹ are each tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15- trienyl, (Z)-icos-11-enyl, (11Z,14Z)-icosa-11,14-dienyl, or (Z)-docos-13-enyl.
(3) The cationic lipid according to the above (1), wherein R¹, R², R⁶, R⁷R⁸, and R⁹ are each (Z)-octadec-9-enyl, (9Z,12Z)-octadeca-9,12-dienyl, or (11Z,14Z)-icosa-11,14-dienyl.
(4) The cationic lipid according to any one of the above (1) to (3), wherein X¹ is alkylene having 1 to 3 carbon atoms, and X² is a single bond or methylene.
(5) The cationic lipid according to any one of the above (1) to (4), wherein X³ is methylene or ethylene.
(6) The cationic lipid according to any one of the above (1) to (5), wherein R³ and R⁴ may be the same or different, and are each methyl or ethyl, or are combined together to form n-pentylene or n-hexylene.
(7) The cationic lipid according to any one of the above (1) to (5), wherein R³ and R⁵ are combined together to form n-propylene or n-butylene, and R⁴ is methyl or ethyl.
(8) The cationic lipid according to any one of the above (1) to (7), wherein R⁵ and R¹⁰ are each a hydrogen atom or methyl.
(9) A composition containing the cationic lipid described in any one of the above (1) to (8) and a nucleic acid.
(10) The composition according to the above (9), wherein the cationic lipid and the nucleic acid form a complex, or a combination of a neutral lipid and/or a polymer with the cationic lipid and the nucleic acid form a complex.
(11) The composition according to the above (9), wherein the cationic lipid and the nucleic acid form a complex, or a combination of a neutral lipid and/or a polymer with the cationic lipid and the nucleic acid form a complex, and the composition contains a lipid membrane which encapsulates the complex.
(12) The composition according to any one of the above (9) to (11), wherein the nucleic acid is a nucleic acid which has an activity of suppressing the expression of a target gene by utilizing RNA interference (RNAi).
(13) The composition according to the above (12), wherein the target gene is a gene which is expressed in the liver, lung, kidney, or spleen.
(14) A method for introducing the nucleic acid into a cell by using the composition described in any one of the above (9) to (13).
(15) The method according to the above (14), wherein the cell is a cell which is present in the liver, lung, kidney, or spleen of a mammal.
(16) The method according to the above (14) or (15), wherein the method for introduction into a cell is a method for introduction of the composition into a cell by intravenous administration.
(17) A method for treating a disease associated with the liver, lung, kidney, or spleen, comprising a step of administering the composition described in the above (13) to a mammal.
(18) The method according to the above (17), wherein the method of administration is intravenous administration.
(19) A pharmaceutical composition for use in the treatment of a disease, comprising the composition described in the above (12).
(20) The pharmaceutical composition according to the above (19), which is for intravenous administration.
(21) A therapeutic agent for a disease associated with the liver, lung, kidney, or spleen, which comprises the composition described in the above (13).
(22) The therapeutic agent for a disease associated with the liver, lung, kidney, or spleen according to the above (21), which is for intravenous administration.

Effects of the Invention

By administering a composition containing the cationic lipid of the present invention and a nucleic acid to a mammal or the like, the nucleic acid can be easily introduced into, for example, a cell or the like.

BRIEF DESCRIPTION OF THE DRAWINGS

FIG. 1 shows the expression ratio of a target gene mRNA after the introduction of preparations obtained in Example 49 (preparations using Compounds A-1, and A-3 to A-5, respectively) and preparations obtained in Comparative Example 1 (preparations using DLin-KC2-DMA and Compounds XI-1 to XI-3, respectively) into cells of a human liver tumor-derived cell line HepG2. The ordinate represents the expression ratio of the target gene mRNA when the expression level of a negative control was taken as 1, and the abscissa represents the nucleic acid concentration (nM), and the compound numbers of the cationic lipids used.

FIG. 2 shows the cholesterol level in serum at 48 hours after the administration of preparations obtained in Example 49 (preparations using Compounds A-1 to A-5, respectively) and a preparation obtained in Comparative Example 1 (a preparation using DLin-KC2-DMA) to mice, respectively, at a dose corresponding to 0.3 mg/kg of siRNA. The ordinate represents the relative value of the cholesterol level in serum when the cholesterol level in serum of a saline-administered group was taken as 100.

FIG. 3 shows the cholesterol level in serum at 48 hours after the administration of preparations obtained in Example 49 (preparations using Compounds A-1 to A-5, respectively) and preparations obtained in Comparative Example 1 (preparations using DLin-KC2-DMA and Compounds XI-1 to XI-3, respectively) to mice, respectively, at a dose corresponding to 3 mg/kg of siRNA. The ordinate represents the relative value of the cholesterol level in serum when the cholesterol level in serum of a saline-administered group was taken as 100.

FIG. 4 shows the Factor VII protein level in plasma at 48 hours after the administration of preparations obtained in Example 50 or 51 (preparations using Compounds A-6, A-1, A-7 and A-8, respectively) to mice, respectively, at a dose corresponding to 0.3 mg/kg of siRNA. The ordinate represents the relative value of the Factor VII protein level in plasma when the Factor VII protein level in plasma of a saline-administered group was taken as 100.

FIG. 5 shows the Factor VII protein level in plasma at 48 hours after the administration of preparations obtained in Example 51 (preparations using Compounds A-9 to A-12, B-1, B-8, and C-1, respectively) to mice, respectively, at a dose corresponding to 0.3 mg/kg of siRNA. The ordinate represents the relative value of the Factor VII protein level in plasma when the Factor VII protein level in plasma of a saline-administered group was taken as 100.

FIG. 6 shows the Factor VII protein level in plasma at 48 hours after the administration of preparations obtained in Example 51 (preparations using Compounds A-5, and A-13 to A-21, respectively) to mice, respectively, at a dose corresponding to 0.3 mg/kg of siRNA. The ordinate represents the relative value of the Factor VII protein level in plasma when the Factor VII protein level in plasma of saline-administered group was taken as 100.

FIG. 7 shows the Factor VII protein level in plasma at 48 hours after the administration of preparations obtained in Example 51 (preparations using Compounds A-28 to A-36, respectively) to mice, respectively, at a dose corresponding to 0.3 mg/kg of siRNA. The ordinate represents the relative value of the Factor VII protein level in plasma when the Factor VII protein level in plasma of a saline-administered group was taken as 100.

FIG. 8 shows the Factor VII protein level in plasma at 48 hours after the administration of preparations obtained in Example 51 (preparations using Compounds C-2 to C-5, respectively) to mice, respectively, at a dose corresponding to 0.3 mg/kg of siRNA. The ordinate represents the relative value of the Factor VII protein level in plasma when the Factor VII protein level in plasma of a saline-administered group was taken as 100.

FIG. 9 shows the Factor VII protein level in plasma at 48 hours after the administration of preparations obtained in Comparative Example 2 (preparations using Compounds XI-4 to XI-8, respectively) to mice, respectively, at a dose corresponding to 0.3 mg/kg of siRNA. The ordinate represents the relative value of the Factor VII protein level in plasma when the Factor VII protein level in plasma of a saline-administered group was taken as 100.

FIG. 10 shows the Factor VII protein level in plasma at 18 hours after the administration of preparations obtained in Example 52 or 53 (preparations using Compounds A-1, A-6, A-7, A-10, A-12, B-8, and C-1, respectively) to mice, respectively, at a dose corresponding to 0.3 or 0.1 mg/kg of siRNA. The ordinate represents the relative value of the Factor VII protein level in plasma when the Factor VII protein level in plasma of a saline-administered group was taken as 100. ■ represents a 0.3 mg/kg-administered group, and □ represents a 0.1 mg/kg-administered group.

FIG. 11 shows the Factor VII protein level in plasma at 48 hours after the administration of preparations obtained in Example 53 (preparations using Compounds A-5, and A-13 to A-21, respectively) to mice, respectively, at a dose corresponding to 0.3 or 0.03 mg/kg of siRNA. The ordinate represents the relative value of the Factor VII protein level in plasma when the Factor VII protein level in plasma of a saline-administered group was taken as 100. ■ represents a 0.3 mg/kg-administered group, and □ represents a 0.03 mg/kg-administered group.

FIG. 12 shows the Factor VII protein level in plasma at 48 hours after the administration of preparations obtained in Example 53 (preparations using Compounds A-28 to A-36, respectively) to mice, respectively, at a dose corresponding to 0.3 or 0.03 mg/kg of siRNA. The ordinate represents the relative value of the Factor VII protein level in plasma when the Factor VII protein level in plasma of a saline-administered group was taken as 100. ■ represents a 0.3 mg/kg-administered group, and □ represents a 0.03 mg/kg-administered group.

FIG. 13 shows the Factor VII protein level in plasma at 48 hours after the administration of preparations obtained in Example 53 or preparations obtained in the same manner as in Example 52 or 53 (preparations using Compounds A-1, A-6, A-10, and C-1 to C-5, respectively), and a preparation obtained in Comparative Example 3 (a preparation using Compound XI-9) to mice, respectively, at a dose corresponding to 0.3 or 0.03 mg/kg of siRNA. The ordinate represents the relative value of the Factor VII protein level in plasma when the Factor VII protein level in plasma of a saline-administered group was taken as 100. ■ represents a 0.3 mg/kg-administered group, and □ represents a 0.03 mg/kg-administered group.

FIG. 14 shows the Factor VII protein level in plasma at 48 hours after the administration of preparations obtained in Example 54 (preparations using Compounds A-1, A-7, and A-10, respectively) to mice, respectively, at a dose corresponding to 0.3 or 0.1 mg/kg of siRNA. The ordinate represents the relative value of the Factor VII protein level in plasma when the Factor VII protein level in plasma of a saline-administered group was taken as 100. ■ represents a 0.3 mg/kg-administered group, and □ represents a 0.1 mg/kg-administered group.

MODES FOR CARRYING OUT THE INVENTION

The cationic lipid of the present invention is a cationic lipid represented by formula (A):

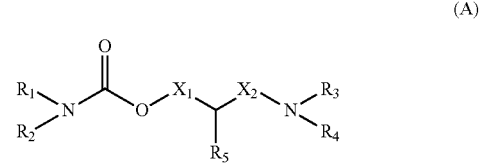

(A)

(wherein $R^1$ is linear or branched alkyl, alkenyl, or alkynyl, each having 8 to 24 carbon atoms, $R^2$ is linear or branched alkyl, alkenyl, or alkynyl, each having 8 to 24 carbon atoms, alkoxyethyl, alkoxypropyl, alkenyloxyethyl, alkenyloxypropyl, alkynyloxyethyl, or alkynyloxypropyl, $R^3$ and $R^4$ may be the same or different, and are each alkyl having 1 to 3 carbon atoms or are combined together to form alkylene having 2 to 8 carbon atoms, or $R^3$ and $R^5$ are combined together to form alkylene having 2 to 6 carbon atoms, $R^5$ is a hydrogen atom, alkyl having 1 to 6 carbon atoms, alkenyl having 3 to 6 carbon atoms, amino, monoalkylamino, hydroxy, alkoxy, carbamoyl, monoalkylcarbamoyl, dialkylcarbamoyl, or alkyl having 1 to 6 carbon atoms or alkenyl having 3 to 6 carbon atoms, each substituted with one to three of the same or different substituents selected from amino, monoalkylamino, hydroxy, alkoxy, carbamoyl, monoalkylcarbamoyl, and dialkylcarbamoyl, or is combined together with $R^3$ to form alkylene having 2 to 8 carbon atoms, $X^1$ is alkylene having 1 to 6 carbon atoms, and $X^2$ is a single bond or alkylene having 1 to 6 carbon atoms, provided that the sum of the number of carbon atoms in $X^1$ and $X^2$ is 7 or less, and when $R^5$ is a hydrogen atom, $X^2$ is a single bond, and when $R^5$ and $R^3$ are combined together to form alkylene having 2 to 6 carbon atoms, $X^2$ is a single bond, or methylene or ethylene), formula (B):

(B)

(wherein $R^6$ is linear or branched alkyl, alkenyl, or alkynyl, each having 8 to 24 carbon atoms, and $R^7$ is linear or branched alkyl, alkenyl, or alkynyl, each having 8 to 24 carbon atoms, alkoxyethyl, alkoxypropyl, alkenyloxyethyl, alkenyloxypropyl, alkynyloxyethyl, or alkynyloxypropyl), or formula (C):

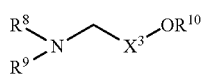

(C)

(wherein $R^8$ is linear or branched alkyl, alkenyl, or alkynyl, each having 8 to 24 carbon atoms, $R^9$ is linear or branched alkyl, alkenyl, or alkynyl, each having 8 to 24 carbon atoms, alkoxyethyl, alkoxypropyl, alkenyloxyethyl, alkenyloxypropyl, alkynyloxyethyl, or alkynyloxypropyl, $X^3$ is alkylene having 1 to 3 carbon atoms, and $R^{10}$ is a hydrogen atom or alkyl having 1 to 3 carbon atoms).

Hereinbelow, the compound represented by the formula (A) is sometimes referred to as Compound (A). The same is applied to the compounds of other formula number.

Examples of the linear or branched alkyl having 8 to 24 carbon atoms include octyl, decyl, dodecyl, tridecyl, tetradecyl, 2,6,10-trimethyldecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl, tetracosyl, and the like.

The linear or branched alkenyl having 8 to 24 carbon atoms may be linear or branched alkenyl having 8 to 24 carbon atoms and having 1 or more double bonds. Examples thereof include (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl, (Z) docos-13-enyl, and the like, and preferred examples thereof include (Z)-hexadec-9-enyl, (Z)-octadec-6-enyl, (Z)-octadec-9-enyl, (9Z,12Z)-octadeca-9,12-dienyl, (Z)-icos-11-enyl, (11Z,14Z)-icosa-11,14-dienyl, (Z)-docos-13-enyl, and the like.

The linear or branched alkynyl having 8 to 24 carbon atoms is linear or branched alkynyl having 8 to 24 carbon atoms and having 1 or more triple bonds. Examples thereof include dodec-11-ynyl, tetradec-6-ynyl, hexadec-7-ynyl, hexadeca-5,7-diynyl, octadec-9-ynyl, and the like.

Examples of the alkyl moiety in the alkoxyethyl and the alkoxypropyl include the groups exemplified for the linear or branched alkyl having 8 to 24 carbon atoms described above, and the like.

Examples of the alkenyl moiety in the alkenyloxyethyl and the alkenyloxypropyl include the groups exemplified for the linear or branched alkenyl having 8 to 24 carbon atoms described above, and the like.

Examples of the alkynyl moiety in the alkynyloxyethyl and the alkynyloxypropyl include the groups exemplified for the linear or branched alkynyl having 8 to 24 carbon atoms described above, and the like.

Incidentally, it is more preferred that $R^1$ and $R^2$ are the same or different and are each linear or branched alkyl or alkenyl, each having 8 to 24 carbon atoms, it is still more preferred that $R^1$ and $R^2$ are the same or different and are each linear or branched alkenyl having 8 to 24 carbon atoms, and it is yet still more preferred that $R^1$ and $R^2$ are the same or different and are each linear alkenyl having 8 to 24 carbon atoms. In addition, it is more preferred that $R^1$ and $R^2$ are the same. In that case, $R^1$ and $R^2$ are each more preferably linear or branched alkyl, alkenyl, or alkynyl, each having 12 to 24 carbon atoms, and still more preferably linear alkenyl having 12 to 24 carbon atoms.

In the case where $R^1$ and $R^2$ are different, it is also one of the preferred embodiments of the present invention that $R^1$ is linear or branched alkyl, alkenyl, or alkynyl, each having 36 to 24 carbon atoms, and $R^2$ is linear or branched alkyl, alkenyl, or alkynyl, each having 8 to 12 carbon atoms. In this case, it is more preferred that $R^1$ is linear alkenyl having 16 to 24 carbon atoms, and $R^2$ is linear alkyl having 8 to 12 carbon atoms, and it is most preferred that $R^1$ is (Z)-octadec-9-enyl or (9Z,12Z)-octadeca-9,12-dienyl, and $R^2$ is octyl, decyl, or dodecyl. In addition, in the case where $R^1$ and $R^2$ are different, it is also one of the preferred embodiments of the present invention that $R^1$ is linear or branched alkyl, alkenyl, or alkynyl, each having 12 to 24 carbon atoms, and $R^2$ is alkoxyethyl, alkoxypropyl, alkenyloxyethyl, alkenyloxypropyl, alkynyloxyethyl, or alkynyloxypropyl. In this case, it is more preferred that $R^1$ is linear alkenyl having 16 to 24 carbon atoms, and $R^1$ is alkenyloxyethyl, it is still more preferred that $R^1$ is (Z)-octadec-9-enyl, (9Z,12Z)-octadeca-9,12-dienyl, or (11Z,14Z)-icosa-11,14-dienyl, and $R^1$ is (Z)-octadec-9-enyloxyethyl, (9Z,12Z)-octadeca-9,12-dienyloxyethyl, or (11Z,14Z)-icosa-11,14-dienyloxyethyl, and it is most preferred that $R^1$ is (9Z,12Z)-octadeca-9,12-dienyl, and R is (9Z,12Z)-octadeca-9,12-dienyloxyethyl.

In the case where $R^1$ and/or $R^2$ is the same or different and is linear or branched alkyl or alkenyl, each having 8 to 24 carbon atoms, it is preferred that $R^1$ and $R^2$ are the same or different and are each tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, or (Z)-docos-13-enyl, it is more preferred that $R^1$ and $R^2$ are the same or different and are each hexadecyl, (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl, it is still more preferred that $R^1$ and $R^2$ are the same or different and are each (Z)-octadec-9-enyl, (9Z,12Z)-octadeca-9,12-dienyl, or (11Z,14Z)-icosa-11,14-dienyl, and it is most preferred that $R^1$ and $R^2$ are the same and are each (9Z,12Z)-octadeca-9,12-dienyl.

$R^6$ and $R^7$ are synonymous with $R^1$ and $R^2$, respectively. However, in the case where $R^7$ is linear or branched alkyl, alkenyl, or alkynyl, each having 16 to 24 carbon atoms, it is preferred that $R^6$ and $R^7$ are the same and are each (9Z,12Z)-octadeca-9,12-dienyl.

$R^8$ and $R^9$ are synonymous with $R^1$ and $R^2$, respectively. However, it is preferred that $R^8$ and $R^9$ are the same and are each linear or branched alkyl, alkenyl, or alkynyl, each having 16 to 24 carbon atoms, and it is more preferred that $R^8$ and $R^9$ are the same and are each (9Z,12Z)-octadeca-9,12-dienyl.

Examples of the alkyl having 1 to 3 carbon atoms represented by $R^3$ and $R^4$ include methyl, ethyl, propyl, isopropyl, and cyclopropyl, preferred examples thereof include methyl and ethyl, and more preferred examples thereof include methyl.

Examples of the alkylene having 2 to 8 carbon atoms, which is formed by $R^3$ and $R^4$ together, include ethylene, n-propylene, n-butylene, n-pentylene, n-hexylene, n-heptylene, n-octylene, and the like, preferred examples thereof include n-pentylene, n-hexylene, n-heptylene, and the like, more preferred examples thereof include n-pentylene, n-hexylene, and the like, and still more preferred examples thereof include n-hexylene.

Incidentally, it is preferred that $R^3$ is methyl or ethyl, or is combined together with $R^4$ to form alkylene having 5 to 7 carbon atoms, or is combined together with $R^5$ to form alkylene having 3 to 5 carbon atoms. However, in the case where R and $R^4$ are not combined together to form alkylene having 5 to 7 carbon atoms, $R^4$ is preferably methyl or ethyl, and more preferably methyl. Furthermore, it is preferred that $R^3$ is methyl, or is combined together with $R^4$ to form n-pentylene or n-hexylene, or $R^3$ and $R^5$ are combined together to form ethylene or n-propylene. However, in the case where $R^3$ and $R^5$ are not combined together to form n-pentylene or n-hexylene, $R^4$ is more preferably methyl.

Examples of the alkyl having 1 to 6 carbon atoms represented by $R^5$ include methyl, ethyl, propyl, isopropyl, cyclopropyl, butyl, isobutyl, sec-butyl, tert-butyl, cyclobutyl, cyclopropylmethyl, pentyl, isopentyl, sec-pentyl, neopentyl, tert-pentyl, cyclopentyl, hexyl, cyclohexyl, and the like, preferred examples thereof include methyl, ethyl, propyl, isopropyl, butyl, isobutyl, sec-butyl, tert-butyl, pentyl, isopentyl, sec-pentyl, tert-pentyl, neopentyl, hexyl, and the like, and more preferred examples thereof include methyl, ethyl, propyl, and the like.

Examples of the alkenyl having 3 to 6 carbon atoms represented by $R^5$ include allyl, 1-propenyl, butenyl, pentenyl, hexenyl, and the like, and preferred examples thereof include allyl and the like.

The monoalkylamino represented by $R^3$ may be amino substituted with one substituent, for example, alkyl having 1 to 6 carbon atoms (having the same definition as described above), and examples thereof include methylamino, ethylamino, propylamino, butyl amino, pentylamino, hexylamino, and the like, and preferred examples thereof include methylamino, ethylamino, and the like.

The amino and the monoalkylamino represented by $R^5$ may form ammonio and monoalkylammonio, respectively, through coordination of a hydrogen ion with a lone pair on the nitrogen atom. The amino and the monoalkylamino include ammonio and monoalkylammonio, respectively.

In the present invention, the ammonio and the monoalkylammonio, in each of which a hydrogen ion is coordinated with a lone pair on the nitrogen atom of each of the amino and the monoalkylamino, may form a salt together with a pharmaceutically acceptable anion.

The alkoxy represented by $R^5$ may be hydroxy substituted with, for example, alkyl having 1 to 6 carbon atoms (having the same definition as described above), and examples thereof include methoxy, ethoxy, propyloxy, butyloxy, pentyloxy, hexyloxy, and the like, and preferred examples thereof include methoxy, ethoxy, and the like.

Examples of the monoalkylcarbamoyl and the dialkylcarbamoyl represented by $R^5$ include carbamoyls substituted with one substituent and the same or different two substituents, respectively, for example, alkyl having 1 to 6 carbon atoms (having the same definition as described above), and more specifically, examples thereof include methylcarbamoyl, ethylcarbamoyl, propylcarbamoyl, butylcarbamoyl, pentylcarbamoyl, hexylcarbamoyl, dimethylcarbamoyl, diethylcarbamoyl, ethylmethylcarbamoyl, methylpropylcarbamoyl, butylmethylcarbamoyl, methylpentylcarbamoyl, hexylmethylcarbamoyl, and the like, and preferred examples thereof include methylcarbamoyl, ethylcarbamoyl, dimethylcarbamoyl, and the like.

Examples of the alkylene having 2 to 6 carbon atoms, which is formed by $R^5$ and $R^3$ together, include ethylene, n-propylene, n-butylene, n-pentylene, n-hexylene, and the like, preferred examples thereof include n-propylene, n-butylene, n-pentylene, and the like, more prefer red examples thereof include n-propylene, n-butylene, and the like, and still more preferred examples thereof include n-propylene.

Incidentally, it is preferred that $R^5$ is a hydrogen atom, alkyl having 1 to 6 carbon atoms, monoalkylamino, hydroxy, alkoxy, or alkyl having 1 to 6 carbons and substituted with one to three of the same or different substituents selected from amino, monoalkylamino, hydroxy, and alkoxy, or is combined together with $R^3$ to form alkylene having 2 o 6 carbon atoms, it is more preferred that $R^5$ is a hydrogen atom, methyl, amino, methylamino, hydroxy, methoxy, or methyl substituted with one to three of the same or different substituents selected from amino and hydroxy, or is combined together with $R^5$ to form alkylene having 3 to 5 carbon atoms, it is still more preferred that $R^5$ is a hydrogen atom, alkyl having 1 to 3 carbon atoms, or hydroxy, or is combined together with $R^3$ to form n-propylene or n-butylene, and it is most preferred that $R^5$ is a hydrogen atom, or is combined together with $R^3$ to form n-propylene.

Examples of the alkyl having 1 to 3 carbon atoms represented by $R^{10}$ include methyl, ethyl, propyl, isopropyl, cyclopropyl, and the like, preferred examples thereof include methyl, ethyl, isopropyl, and the like, and more preferred examples thereof include methyl, ethyl, and the like. Incidentally, $R^{10}$ is more preferably a hydrogen atom or methyl, and most preferably a hydrogen atom.

Examples of the alkylene having 1 to 6 carbon atoms represented by $X^1$ and $X^2$ include methylene, ethylene, n-propylene, n-butylene, n-pentylene, n-hexylene, and the like.

In addition, $X^1$ is preferably alkylene having 1 to 3 carbon atoms, and most preferably methylene or ethylene. $X^2$ is preferably a single bond, methylene, or ethylene, and more preferably a single bond or methylene. The sum of the number of carbon atoms in $X^1$ and $X^2$ is preferably 1 to 3, and most preferably 2. In any case, it is preferred that $R^3$ and $R^4$ are the same or different and are each methyl or ethyl, and $R^5$ is a hydrogen atom, methyl, amino, methylamino, hydroxy, methoxy, or methyl substituted with one to three of the same or different substituents selected from amino and hydroxy; $R^3$ and $R^4$ are combined together to form alkylene having 5 to 7 carbon atoms, and $R^5$ is a hydrogen atom, methyl, amino, methylamino, hydroxy, methoxy, or methyl substituted with one to three of the same or different substituents selected from amino and hydroxy; or $R^3$ and $R^5$ are combined together to form alkylene having 3 to 5 carbon atoms, and $R^4$ is methyl or ethyl. It is more preferred that $R^3$ and $R^4$ are each methyl, and $R^5$ is a hydrogen atom; $R^3$ and $R^4$ are combined together to form n-pentylene or n-hexylene, and $R^5$ is a hydrogen atom; or $R^3$ and $R^5$ are combined together to form n-propylene, and $R^4$ is methyl.

Examples of the alkylene having 1 to 3 carbon atoms represented by $X^3$ include methylene, ethylene, n-propylene, and the like, and preferred examples thereof include methylene, ethylene, and the like.

Each of the oxygen atoms in formula (A) may be replaced with a sulfur atom.

Compound (Aa) represented by formula (Aa) in which one of the oxygen atoms in formula (A) is replaced with a sulfur atom:

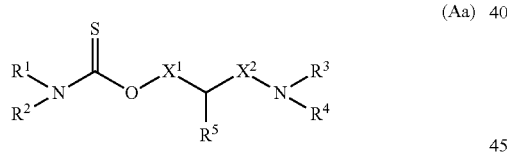

(Aa)

(wherein $R^1$, $R^2$, $R^3$, $R^4$, $R^5$, $X^1$, and $X^2$ have the same definitions as described above, respectively) can be obtained by allowing a 1,3,2,4-dithiadiphosphetane 2,4-disulfide derivative such as Lawesson's reagent, (2,4-bis(4-methoxyphenyl)-1,3,2,4-dithiadiphosphetane-2,4-disulfide) to act on corresponding Compound (A).

The cationic lipid of the present invention may form a salt with a pharmaceutically acceptable anion in the case where a hydrogen ion is coordinated with a lone pair on any nitrogen atom.

In the present invention, examples of the pharmaceutically acceptable anion include inorganic ions such as a chloride ion, a bromide ion, a nitrate ion, a sulfate ion, or a phosphate ion, organic acid ions such as an acetate ion, an oxalate ion, a maleate ion, a fumarate ion, a citrate ion, a benzoate ion, or a methanesulfonate ion, and the like.

Next, a production method of the cationic lipid of the present invention will be described. Incidentally, in the following production method, in the case where a defined group changes under the conditions for the production method or is not suitable for carrying out the production method, the target compound can be produced by adopting the introduction and removal method of a protective group commonly used in synthetic organic chemistry [for example, the method described in *Protective Groups in Organic Synthesis, Third Edition*, written by T. W. Greene, John Wiley & Sons, Inc. (1999), or the like] or the like. In addition, if desired, the order of reaction steps such as introduction of a substituent can be altered.

Production Method

Compound (Ia) in which in Compound (A), $R^2$ is linear or branched alkyl, alkenyl, or alkynyl, each having 8 to 24 carbon atoms, can be produced by the following method.

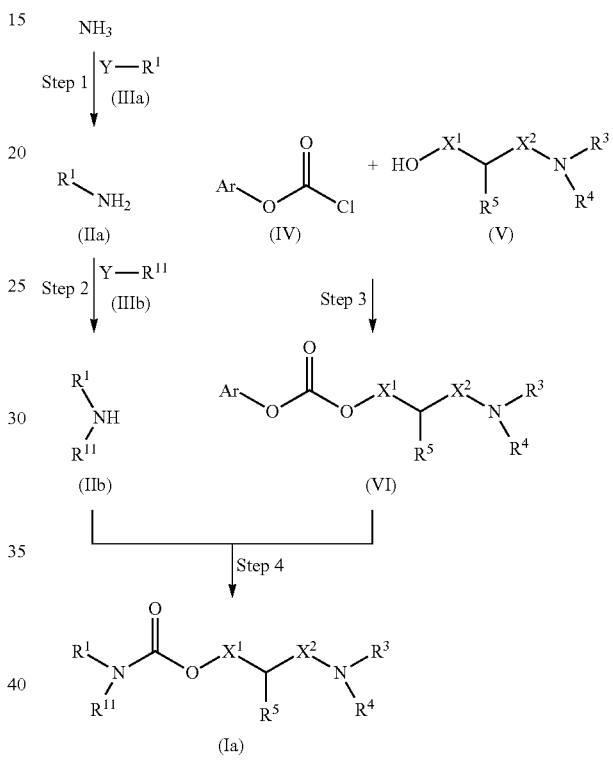

(Wherein $R^1$, $R^3$, $R^4$, $R^5$, $X^1$, and $X^2$ have the same definitions as described above, respectively, $R^{11}$ is linear or branched alkyl, alkenyl, or alkynyl, each having 8 to 24 carbon atoms, Y represents a leaving group such as a chlorine atom, a bromine atom, an iodine atom, trifluoromethanesulfonyloxy, methanesulfonyloxy, benzenesulfonyloxy, or p-toluenesulfonyloxy, and Ar represents a substituted phenyl group such as p-nitrophenyl, o-nitrophenyl, or p-chlorophenyl, or an unsubstituted phenyl group.)

Steps 1 and 2

Compound (IIa) can be produced by allowing ammonia and Compound (IIIa) to react with each other without a solvent or in a solvent, if necessary, preferably in the presence of 1 to 10 equivalents of a base at a temperature between room temperature and 200° C. for 5 minutes to 100 hours. Furthermore, Compound (IIb) can be produced by allowing Compound (IIa) and Compound (IIIb) to react with each other without a solvent or in a solvent, if necessary, preferably in the presence of 1 to 10 equivalents of a base at a temperature between room temperature and 200° C. for 5 minutes to 100 hours.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, water, and the like. These are used alone or as a mixture.

Examples of the base include potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), and the like.

Compound (IIIa) and Compound (IIIb) can be obtained as commercially available products or by known methods (for example, "Dai 5-han Jikken Kagaku Kouza 1.3, Synthesis of Organic Compounds I", 5th Ed., p. 374, Maruzen (2005)) or modified methods thereof.

Compound (IIb) in the case where $R^1$ and $R^{11}$ are the same can be obtained by using 2 equivalents or more of Compound (IIIa) in Step 1.

Step 3

Compound (VI) can be produced by allowing Compound (IV) to react with Compound (V) without a solvent or in a solvent, it necessary, preferably in the presence of 1 to 10 equivalents of an additive, and/or ii necessary, preferably in the presence of 1 to 10 equivalents of a base at a temperature between −20° C. and 150° C. for 5 minutes to 72 hours.

Examples of the solvent include dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, dimethyl sulfoxide, and the like. These can be used alone or as a mixture.

Examples of the additive include 1-hydroxybenzotriazole, 4-dimethylaminopyridine, and the like.

Examples of the base include those exemplified with respect to Steps 1 and 2.

Compound (IV) can be obtained as a commercially available product.

Compound (V) can be obtained as a commercially available product or by known methods (for example, "Dai 5-han, Jikken Kagaku Kouza 14, Synthesis of Organic Compounds II", 5th Ed., p. 1, Maruzen (2005)) or modified methods thereof.

Step 4

Compound (Ia) can be produced by allowing Compound (IIb) to react with Compound (VI) without a solvent or in a solvent, if necessary, preferably in the presence of 1 to 10 equivalents of an additive, and/or if necessary, preferably in the presence of 1 to 10 equivalents of a base at a temperature between −20° C. and 150° C. for 5 minutes to 72 hours.

Examples of the solvent and the additive include those exemplified, respectively with respect to Step 3.

Examples of the base include those exemplified with respect to Steps 1 and 2.

Compound (IIb) can also be produced by the following method.

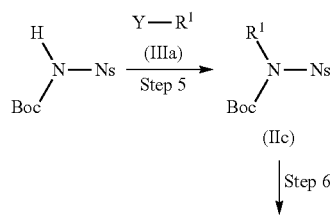

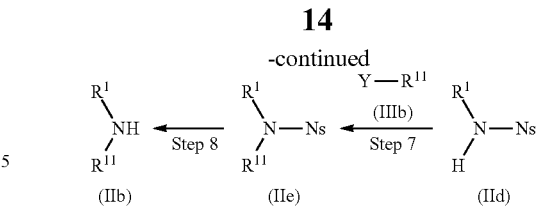

(Wherein $R^1$, $R^{11}$, and Y have the same definitions as described above, respectively, Boc represents a tert-butoxycarbonyl group, and Ns represents a 2-nitrobenzenesulfonyl group.)

Step 5

Compound (IIc) can be produced by allowing N-(tert-butoxycarbonyl)-2-nitrobenznesulfonamide and Compound (IIIa) to react with each other without a solvent or in a solvent, if necessary, preferably in the presence of 1 to 10 equivalents of an additive, and/or if necessary, preferably in the presence of 1 to 10 equivalents of a base at a temperature between room temperature and 200° C. for 5 minutes to 100 hours.

Examples of the solvent include those exemplified with respect to Steps 1 and 2.

Examples of the additive include n-tetrabutylammonium iodide, sodium iodide, and the like.

Examples of the base include cesium carbonate, potassium carbonate, potassium hydroxide, sodium hydroxide, sodium methoxide, potassium tert-butoxide, triethylamine, diisopropylethylamine, N-methylmorpholine, pyridine, DBU, and the like.

Step 6

Compound (IId) can be produced by treating Compound (IIc) with 1 equivalent to a large excess amount of an acid without a solvent or in a solvent, if necessary, preferably in the presence of 1 to 10 equivalents of an additive at a temperature between −20° C. and 150° C. for 5 minutes to 72 hours.

Examples of the solvent include those exemplified with respect to Steps 1 and 2.

Examples of the acid include hydrochloric acid, sulfuric acid, phosphoric acid, trifluoroacetic acid, and the like.

Examples of the additive include thioanisole, dimethyl sulfide, triisopropylsilane, and the like.

Step 7

Compound (IIe) can be produced by allowing Compound (IIIb) and Compound (IId) to react with each other without a solvent or in a solvent, if necessary, preferably in the presence of 1 to 10 equivalents of an additive, and/or if necessary, preferably in the presence of 1 to 10 equivalents of a base at a temperature between room temperature and 200° C. for 5 minutes to 100 hours.

Examples of the solvent include those exemplified with respect to Steps 1 and 2.

Examples of the additive and the base include those exemplified, respectively with respect to Step 5.

Step 8

Compound (IIb) can be produced by allowing Compound (IIe) and a thiol compound to react with each other without a solvent or in a solvent, if necessary, preferably in the presence of 1 to 10 equivalents of a base at a temperature between −20° C. and 200° C. for 5 minutes to 100 hours.

Examples of the solvent include those exemplified with respect to Steps 1 and 2.

Examples of the thiol compound include methanethiol, ethanethiol, dodecanethiol, thiophenol, mercaptoacetic acid, and the like.

Examples of the base include those exemplified with respect to Step 5.

Compound (Ib) in which in Compound (A), $R^2$ is alkoxyethyl, alkoxypropyl, alkenyloxyethyl, alkenyloxypropyl, alkynyloxyethyl, or alkynyloxypropyl can be produced by the following method.

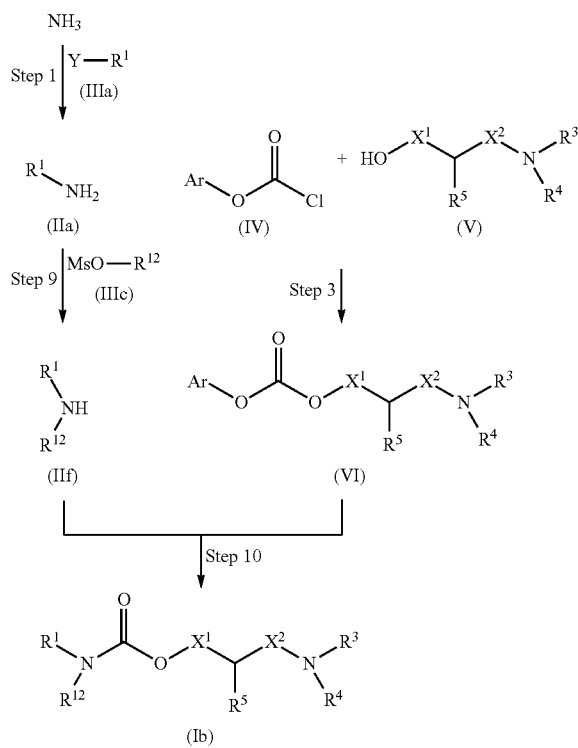

(Wherein $R^1$, $R^3$, $R^4$, $R^5$, $X^1$, $X^2$, Y, and Ar have the same definitions as described above, respectively, $R^{12}$ is alkoxyethyl, alkoxypropyl, alkenyloxyethyl, alkenyloxypropyl, alkynyloxyethyl, or alkynyloxypropyl, and Ms represents a methanesulfonyl group.)

Step 9

Compound (IIf) can be produced by allowing Compound (IIa) and Compound (IIIc) to react with each other without a solvent or in a solvent, if necessary, preferably in the presence of 1 to 10 equivalents of a base at a temperature between room temperature and 200° C. for 5 minutes to 100 hours.

Examples of the solvent include those exemplified with respect to Steps 1 and 2.

Examples of the base include those exemplified with respect to Steps 1 and 2.

Step 10

Compound (Ib) can be produced by allowing Compound (IIf) to react with Compound (VI) without a solvent or in a solvent, if necessary, preferably in the presence of 1 to 10 equivalents of an additive, and/or if necessary, preferably in the presence of 1 to 10 equivalents of a base at a temperature between −20° C. and 150° C. for 5 minutes to 72 hours.

Examples of the solvent and the additive include those exemplified, respectively with respect to Step 3.

Examples of the base include those exemplified with respect to Steps 1 and 2.

Compound (IIIc) can be produced by the following method.

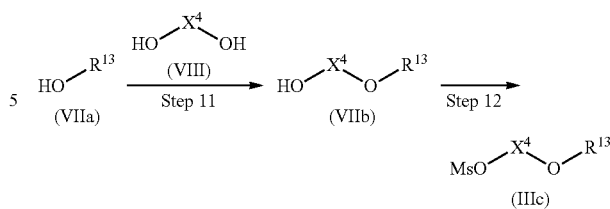

(Wherein $R^{13}$ is linear or branched alkyl, alkenyl, or alkynyl, each having 8 to 24 carbon atoms, $X^4$ represents ethylene or n-propylene, and Ms represents a methanesulfonyl group.)

Step 11

Compound (VIIb) can be produced by allowing Compound (VIIa) to react with Compound (VIII) without a solvent or in a solvent, if necessary, preferably in the presence of 1 to 10 equivalents of a base at a temperature between room temperature and 200° C. for 5 minutes to 100 hours.

Examples of the solvent include those exemplified with respect to Step 3.

Examples of the base include those exemplified with respect to Steps 1 and 2.

Compound (VIIa) can be obtained as a commercially available product or by known methods (for example, "Dai 5-han, Jikken Kagaku Kouza 14, Synthesis of Organic Compounds II", 5th Ed., p. 1, Maruzen (2005)) or modified methods thereof.

Compound (VIII) can be obtained as a commercially available product.

Step 12

Compound (IIIc) can be produced by allowing Compound (VIIb) to react with a mesylating reagent without a solvent or in a solvent, if necessary, preferably in the presence of 1 to 10 equivalents of a base at a temperature between −20° C. and 150° C. for 5 minutes to 72 hours.

Examples of the solvent include those exemplified with respect to Step 3.

Examples of the base include those exemplified with respect to Steps 1 and 2.

Examples of the mesylating agent include mesylic anhydride, mesylic acid chloride, and the like.

Compound (IIf) can also be produced by the following method.

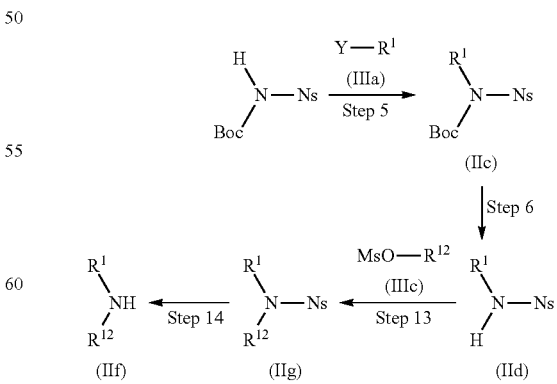

(Wherein $R^1$, $R^{12}$, Y, Ns, and Ms have the same definitions as described above, respectively.)

Step 13

Compound (IIg) can be produced by allowing Compound (IIIc) and Compound (IId) to react with each other without a solvent or in a solvent, if necessary, preferably in the presence of 1 to 10 equivalents of an additive, and/or if necessary, preferably in the presence of 1 to 10 equivalents of a base at a temperature between room temperature and 200° C. for 5 minutes to 100 hours.

Examples of the solvent include those exemplified with respect to Steps 1 and 2.

Examples of the additive and the base include those exemplified, respectively with respect to Step 5.

Step 14

Compound (IIf) can be produced by allowing Compound (IIg) and a thiol compound to react with each other without a solvent or in a solvent, if necessary, preferably in the presence of 1 to 10 equivalents of a base at a temperature between room temperature and 200° C. for 5 minutes to 100 hours.

Examples of the solvent include those exemplified with respect to Steps 1 and 2.

Examples of the thiol compound include those exemplified with respect to Step 8. Examples of the base include those exemplified with respect to Step 5.

Compounds (Aa) to (Ac) represented by formulae (Aa) to (Ac) in which an oxygen atom in formula (A) is replaced with a sulfur atom:

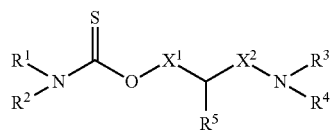

(Aa)

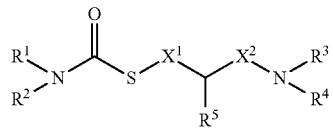

(Ab)

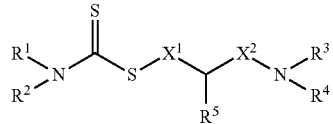

(Ac)

(wherein $R^1$, $R^2$, $R^3$, $R^4$, $R^5$, $X^1$, and $X^2$ have the same definitions as described above, respectively) can be obtained by using Compounds (VIa) to (VIc) represented by formulae (VIa) to (VIc) in which an oxygen atom in formula (VI) is replaced with a sulfur atom:

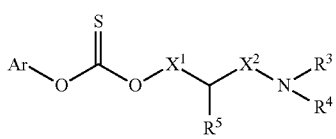

(VIa)

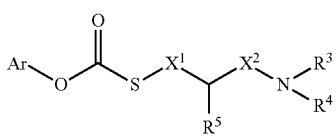

(VIb)

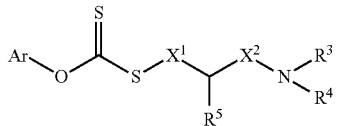

(VIc)

(wherein $R^3$, $R^4$, $R^5$, $X^1$, $X^2$, and Ar have the same definitions as described above, respectively) in Steps 4 and 10, respectively.

Compound (Ba) in which in Compound (B), $R^7$ is linear or branched alkyl, alkenyl, or alkynyl, each having 8 to 24 carbon atoms, can be obtained by the production method of Compound (IIb).

Compound (Bc) in which in Compound (B), $R^7$ is alkoxyethyl, alkoxypropyl, alkenyloxyethyl, alkenyloxypropyl, alkynyloxyethyl, or alkynyloxypropyl can be obtained by the production method of Compound (IIf).

Compound (C) can be produced by the following method.

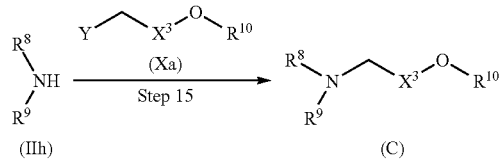

(Wherein $R^8$, $R^9$, $R^{10}$, $X^3$, and Y have the same definitions as described above, respectively.)

Step 15

Compound (C) can be produced by allowing Compound (IIh) and Compound (Xa) to react with each other without a solvent or in a solvent, if necessary, preferably in the presence of 1 to 10 equivalents of an additive, and/or if necessary, preferably in the presence of 1 to 10 equivalents of a base at a temperature between room temperature and 200° C. for 5 minutes to 100 hours.

Examples of the solvent and the base include those exemplified, respectively with respect to Steps 1 and 2.

Examples of the additive include those exemplified with respect to Step 5.

Compound (IIh) can be obtained by the production method of Compound (B).

Compound (Xa) can be obtained as a commercially available product or by known methods (for example, "Dai 5-han, Jikken Kagaku Kouza 13, Synthesis of Organic Compounds I", 5th Ed., p. 374, Maruzen (2005)) or modified methods thereof.

Compound (Ca) in which in Compound (C), $R^{10}$ is a hydrogen atom can be produced by the following method.

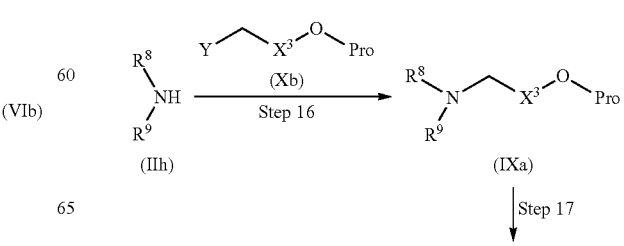

Step 17

-continued

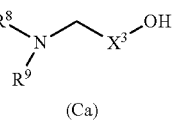

(Ca)

(Wherein $R^8$, $R^9$, $X^3$, and Y have the same definitions as described above, respectively, and Pro represents a silyl-type protective group such as trimethylsilyl, triethylsilyl, tri-tert-butylsilyl, tert-butyldimethylsilyl, tert-butyldiphenylsilyl, or triphenylsilyl.)

Step 16

Compound (IXa) can be produced by allowing Compound (IIh) and Compound (Xb) to react with each other without a solvent or in a solvent, if necessary, preferably in the presence of 1 to 10 equivalents of an additive, and/or if necessary, preferably in the presence of 1 to 10 equivalents of a base at a temperature between room temperature and 200° C. for 5 minutes to 100 hours.

Examples of the solvent and the base include those exemplified, respectively with respect to Steps 1 and 2.

Examples of the additive include those exemplified with respect to Step 5.

Compound (IIh) can be obtained by the production method of Compound (B).

Compound (Xb) can be obtained a: a commercially available product or by known methods (for example, "Dai 5-han, Jikken Kagaku Kouza 18, Synthesis of Organic Compounds VI", 5th Ed., pp. 171-172, Maruzen (2005)) or modified methods thereof.

Step 17

Compound (Ca) can be produced by allowing Compound (IXa) and a deprotecting reagent to react with each other without a solvent or in a solvent at a temperature between −20° C. and 150° C. for 5 minutes to 72 hours.

Examples of the solvent include chose exemplified with respect to Steps 1 and 2.

Examples of the deprotecting reagent include fluorine compounds such as tetrabutylammonium fluoride, a hydrogen fluoride-pyridine complex, or hydrofluoric acid, acids such as acetic acid, trifluoroacetic acid, pyridinium p-toluenesulfonate, or hydrochloric acid, and the like. Compound (Cb) in which in Compound (C), $R^{10}$ is a hydrogen atom, and $X^3$ alkylene having 2 carbon atoms can also be produced by the following method.

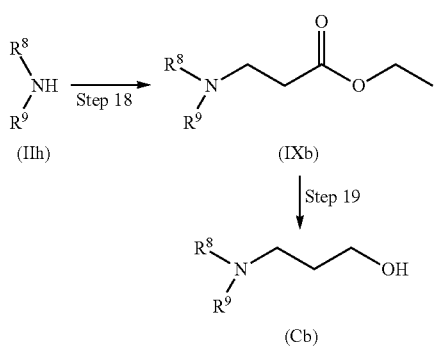

(Wherein $R^8$ and $R^9$ have the same definitions as described above, respectively.)

Step 18

Compound (IXb) can be produced by allowing Compound (IIb) to react with preferably 1 to a large excess amount of ethyl acrylate without a solvent or in a solvent, if necessary, preferably in the presence of 1 to 10 equivalents of a base at a temperature between room temperature and 200° C. for 5 minutes to 100 hours.

Examples of the solvent include those exemplified with respect to Step 1.

Examples of the base include potassium carbonate, potassium hydroxide, sodium hydroxide, sodium methoxide, sodium ethoxide, potassium tert-butoxide, triethylamine, diisopropylethylamine, N-methylmorpholine, pyridine, DBU, and the like.

Step 19

Compound (Cb) can be produced by allowing Compound (IXb) to react with preferably 1 to 10 equivalents of a reducing agent in a solvent, if necessary, preferably in the presence of 1 to 10 equivalents of an additive at a temperature between −20° C. and 150° C. for 5 minutes to 72 hours.

Examples of the solvent include tetrahydrofuran, dioxane, diethyl ether, dichloromethane, toluene, and the like. These can be used alone or as a mixture.

Examples of the reducing agent include lithium aluminum hydride, aluminum hydride, diisobutyl aluminum hydride, triacetoxy sodium borohydride, sodium cyanoborohydride, borane, and the like.

Examples of the additive include aluminum chloride, cerium chloride, iron chloride, acetic acid, hydrochloric acid, and the like.

The intermediates and the target compounds in the above-described respective production methods can be isolated and purified by separation and purification methods commonly used in synthetic organic chemistry, for example, filtration, extraction, washing, drying, concentration, recrystallization, various chromatographies, and the like. In addition, it is also possible to subject the intermediate to the subsequent reaction without particularly purifying it.

In the cationic lipid of the present invention, a hydrogen ion may be coordinated with a lone pair on the nitrogen atom ill the structure, and in that case, it may form a salt together with a pharmaceutically acceptable anion (having the same definition as described above). The cationic lipid of the present invention also includes compounds in which a hydrogen ion is coordinated with a lone pair on the nitrogen atom.

In the cationic lipid of the present invention, there may exist compounds in the form of stereoisomers such as geometric isomers or optical isomers, tautomers, and the like. The cationic lipid of the present invention includes all the possible isomers and mixtures thereof inclusive of these stereoisomers and tautomers.

A part or all of the respective atoms in the cationic lipid of the present invention may be replaced with a corresponding isotope atom. Compound (A), Compound (B), or Compound (C) also includes such compounds in which a part or all of the respective atoms are replaced with a corresponding isotope atom. For example, a part or all of the hydrogen atoms in Compound (A), Compound (B), or Compound (C) may be a hydrogen atom having an atomic weight of 2 (deuterium atom).

The compounds in which a part or all of the respective atoms in the cationic lipid of the present invention are replaced with a corresponding isotope atom can be produced by the same methods as the above-described respective production methods using a commercially available building block. In addition, the compounds in which a part or all of the hydrogen atoms in Compound (A), Compound (B), or Compound (C) are replaced with a deuterium atom can also be synthesized by using, for example, a method in which an alcohol, a carboxylic acid, or the like is deuterated by using an iridium complex as a catalyst and using heavy water as a deuterium source [see *Journal of American Chemical Society* (*J. Am. Chem. Soc.*), Vol. 124, No. 10, 2092 (2002,), or the like.

Specific examples of the cationic lipid of the present invention obtained according to the present invention are shown in Tables 1 to 7. It should be noted, however, that the cationic lipid of the present invention is not limited to these.

TABLE 1

| Compound No. | Structural formula |
|---|---|
| A-1 | |
| A-2 | |
| A-3 | |
| A-4 | |
| A-5 | |
| A-6 | |
| A-7 | |
| A-8 | |

TABLE 2

| Compound No. | Structural formula |
|---|---|
| A-9 | |

TABLE 2-continued

| Compound No. | Structural formula |
| --- | --- |
| A-10 | |
| A-11 | |
| A-12 | |
| A-13 | |
| A-14 | |
| A-15 | |
| A-16 | |

TABLE 3

| Compound No. | Structural formula |
| --- | --- |
| A-17 | |
| A-18 | |

TABLE 3-continued
| Compound No. | Structural formula |
|---|---|
| A-19 | 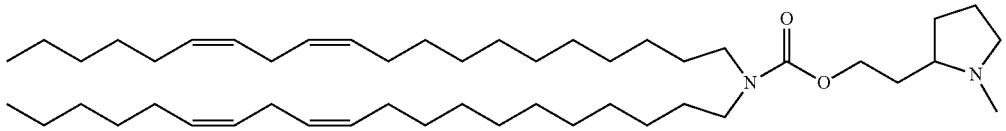 |
| A-20 | 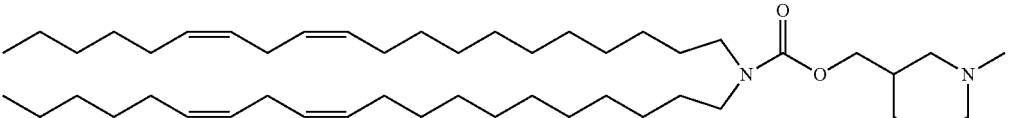 [SMILES: CCCCC/C=C\C/C=C\CCCCCCCCCCN(CCCCCCCCCC/C=C\C/C=C\CCCCC)C(=O)OCCCN(C)C] |
| A-21 | 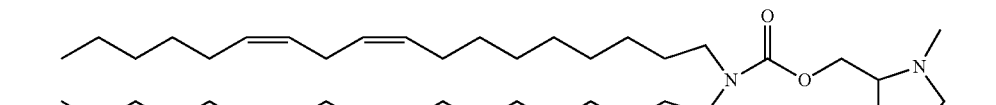 |
| A-22 | 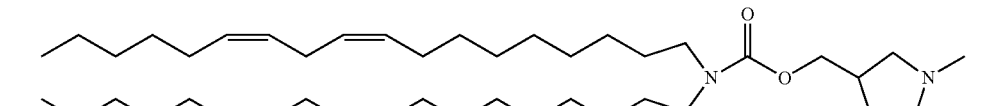 |
| A-23 | 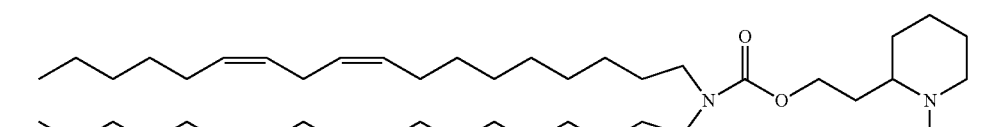 |
| A-_24 | 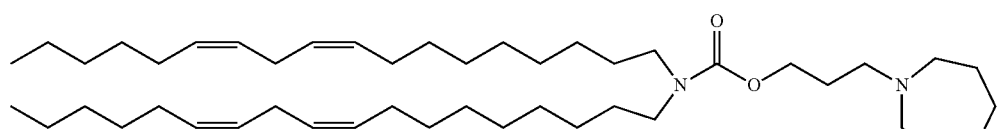 |
TABLE 4
| Compound No. | Structural formula |
|---|---|
| A-25 | 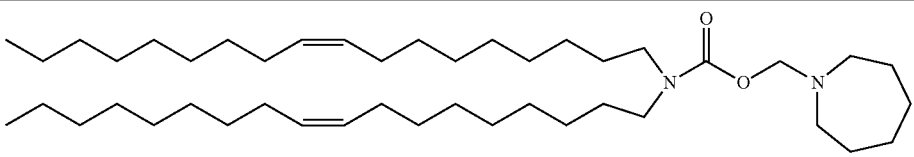 [SMILES: CCCCCCCC/C=C\CCCCCCCCN(CCCCCCCC/C=C\CCCCCCCC)C(=O)OCN1CCCCCC1] |
| A-26 | 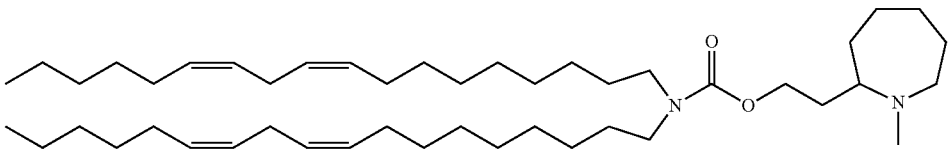 [SMILES: CCCCC/C=C\C/C=C\CCCCCCCCN(CCCCCCCC/C=C\C/C=C\CCCCC)C(=O)OCCC1CCCCCN1C] |
| A-27 | 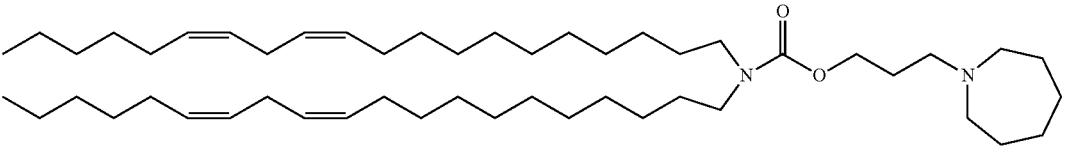 [SMILES: CCCCC/C=C\C/C=C\CCCCCCCCCCN(CCCCCCCCCC/C=C\C/C=C\CCCCC)C(=O)OCCCN1CCCCCC1] |

TABLE 4-continued
| Compound No. | Structural formula |
|---|---|
| A-28 | 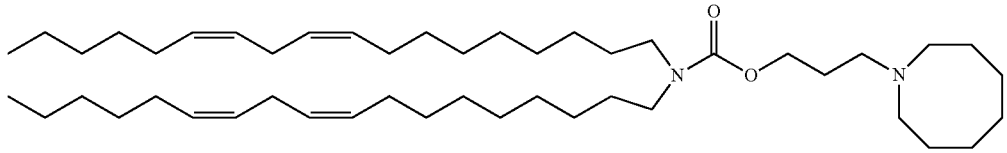 [SMILES: CCCCC/C=C\C/C=C\CCCCCCCCN(CCCCCCCC/C=C\C/C=C\CCCCC)C(=O)OCCCN1CCCCCCC1] |
| A-29 | 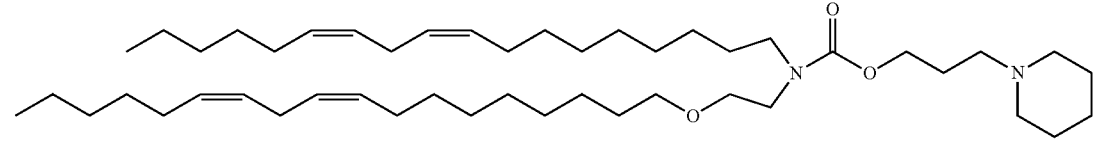 [SMILES: CCCCC/C=C\C/C=C\CCCCCCCCOCCN(CCCCCCCC/C=C\C/C=C\CCCCC)C(=O)OCCCN1CCCCC1] |
| A-30 | 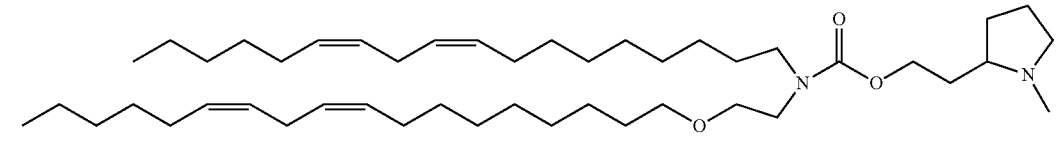 [SMILES: CCCCC/C=C\C/C=C\CCCCCCCCOCCN(CCCCCCCC/C=C\C/C=C\CCCCC)C(=O)OCCC1CCCN1C] |
| A-31 | 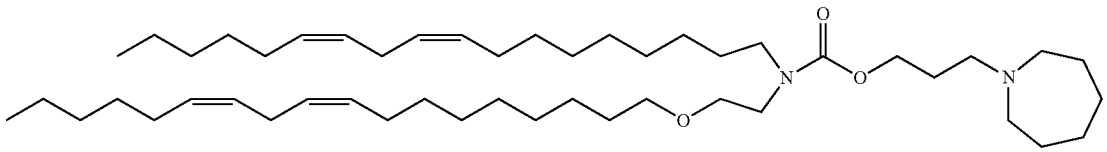 [SMILES: CCCCC/C=C\C/C=C\CCCCCCCCOCCN(CCCCCCCC/C=C\C/C=C\CCCCC)C(=O)OCCCN1CCCCCC1] |
TABLE 5
| Compound No. | Structural formula |
|---|---|
| A-32 | 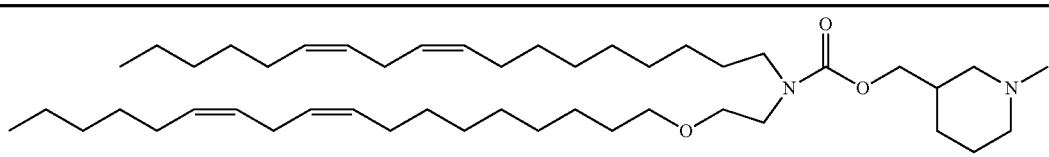 |
| A-33 | 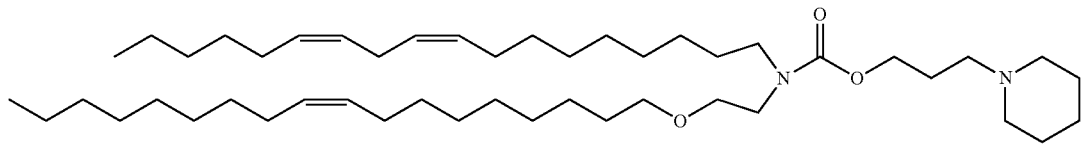 [SMILES: CCCCC/C=C\C/C=C\CCCCCCCCN(CCOCCCCCCCC/C=C\CCCCCCCC)C(=O)OCCCN1CCCCC1] |
| A-34 | 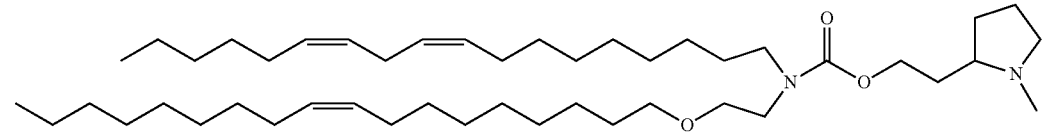 [SMILES: CCCCC/C=C\C/C=C\CCCCCCCCN(CCOCCCCCCCC/C=C\CCCCCCCC)C(=O)OCCC1CCCN1C] |
| A-35 | 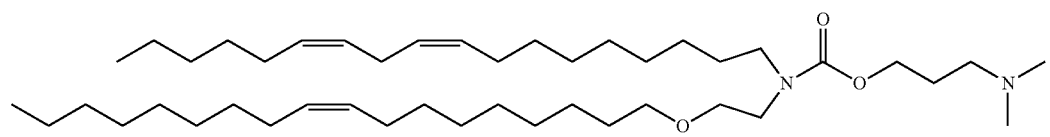 [SMILES: CCCCC/C=C\C/C=C\CCCCCCCCN(CCOCCCCCCCC/C=C\CCCCCCCC)C(=O)OCCCN(C)C] |
| A-36 | 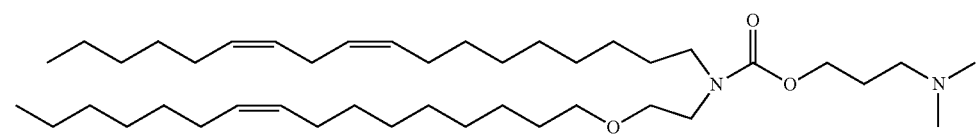 [SMILES: CCCCC/C=C\C/C=C\CCCCCCCCN(CCOCCCCCCCC/C=C\CCCCCC)C(=O)OCCCN(C)C] |

TABLE 5-continued
| Compound No. | Structural formula |
|---|---|
| A-37 | 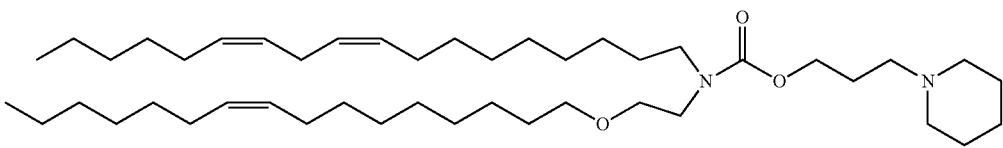 [SMILES: CCCCC/C=C\C/C=C\CCCCCCCCN(CCOCCCCCCCC/C=C\CCCCCC)C(=O)OCCCN1CCCCC1] |
| A-38 | 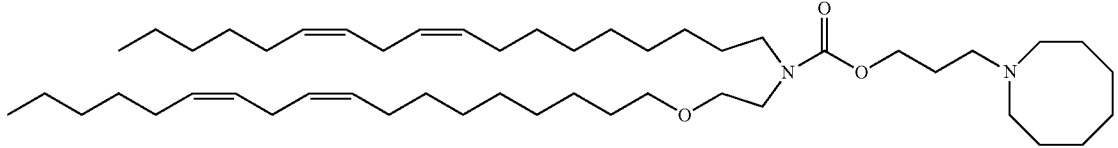 [SMILES: CCCCC/C=C\C/C=C\CCCCCCCCOCCN(CCCCCCCC/C=C\C/C=C\CCCCC)C(=O)OCCCN1CCCCCCC1] |
TABLE 6
| Compound No. | Structural formula |
|---|---|
| B-1 | 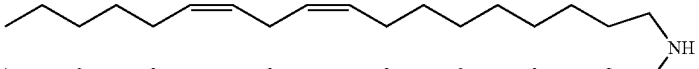 |
| B-2 | 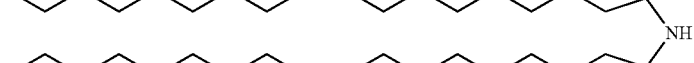 |
| B-3 |  |
| B-4 | 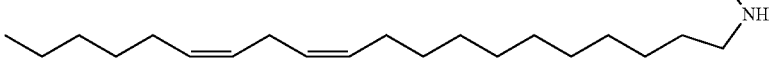 |
| B-5 | 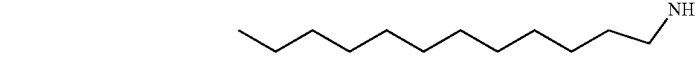 |
| B-6 | 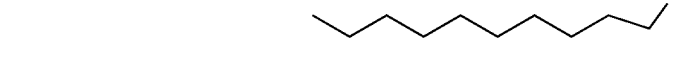 |
| B-7 |  |
| B-8 | 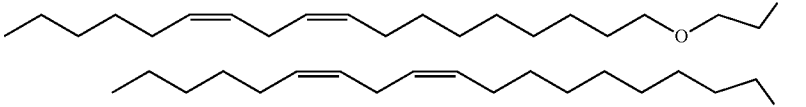 |
| B-9 | 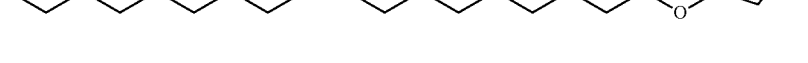 |

TABLE 6-continued

| Compound No. | Structural formula |
|---|---|
| B-10 | (long-chain structure with NH and O) |

TABLE 7

| Compound No. | Structural formula |
|---|---|
| C-1 | (long-chain structure with N and OH) |
| C-2 | (long-chain structure with N and OH) |
| C-3 | (long-chain structure with N and OH) |
| C-4 | (long-chain structure with N and OH) |
| C-5 | (long-chain structure with N and OH) |

In addition, the nucleic acid to be used in the present invention may be any molecule as long as it is a molecule obtained by polymerization of, for example, a nucleotide and/or a molecule having a function equivalent to that of the nucleotide. Examples thereof include ribonucleic acid (RNA) which is a polymer of a ribonucleotide, deoxyribonucleic acid (DNA) which is a polymer of a deoxyribonucleotide, a chimera nucleic acid composed of RNA and DNA, a nucleotide polymer in which at least one nucleotide of these nucleic acids is substituted with a molecule having a function equivalent to that of the nucleotide, and the like. In addition, a derivative containing a structure of a molecule obtained by polymerization of a nucleotide and/or a molecule having a function equivalent to that of the nucleotide in at least a part thereof is also included in the nucleic acid of the present invention. Incidentally, in the present invention, uracil U in RNA and thymine T can be replaced with each other.

Examples of the molecule having a function equivalent to that of a nucleotide include nucleotide derivatives and the like.

The nucleotide derivative may be any molecule as long as it is a molecule obtained by, for example, modifying a nucleotide. For example, for the purpose of enhancing the nuclease resistance or achieving stabilization against other decomposing factors as compared with RNA or DNA, increasing the affinity for a complementary strand nucleic acid, increasing the cellular permeability, or achieving the visualization, a molecule obtained by modifying a ribonucleotide or a deoxyribonucleotide, or the like is preferably used.

Examples of the nucleotide derivative include a sugar moiety-modified nucleotide, a phosphodiester bond-modified nucleotide, a base-modified nucleotide, and the like.

The sugar moiety-modified nucleotide may be any as long as it is a nucleotide in which, for example, a part or all of the chemical structure of the sugar moiety of the nucleotide is modified or substituted with an arbitrary substituent or substituted with an arbitrary atom, however, a 2'-modified nucleotide is preferably used.

Examples of the modifying group in the sugar moiety-modified nucleotide include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'-SiH$_2$-substituted alkyl, 2'-ONO$_2$, 2'-NO$_2$, 2'-N$_3$, a 2'-amino acid residue (a residue obtained by removing the hydroxyl group from the carboxylic acid of an amino acid), a 2'-O-amino acid residue (having the same definition as the above-described amino acid residue), and the like.

In addition, additional examples of the sugar moiety-modified nucleotide include bridged nucleic acids (BNAs)

having a structure in which the modifying group at the 2' position is bridged to the carbon atom at the 4' position, more specifically, locked nucleic acids (LNAs) in which the oxygen atom at the 2' position is bridged to the carbon atom at the 4' position via methylene, ethylene bridged nucleic acids (ENAs) [*Nucleic Acid Research*, 32, e175 (2004)], and the like. These are included in the 2'-modified nucleotide.

Furthermore, additional examples of the sugar moiety-modified nucleotide include a peptide nucleic acid (PNA) [*Acc. Chem. Res.*, 32, 624 (1999)], an oxy-peptide nucleic acid (OPNA) [*J. Am. Chem. Soc.*, 123, 4653 (2001)], a peptide ribonucleic acid (PRNA) [*J. Am. Chem. Soc.*, 122, 6900 (2000)], and the like.

As the modifying group in the sugar moiety-modified nucleotide, 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, and the like are preferred, 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethylaminooxy)ethyl], 2'-O-[3-(N,N-dimethylamino) propyl], 2'-O-{2-[2-(N,N-dimethylamino)ethoxy]ethyl}, 2'-O-[2-(methylamino)-2-oxoethyl], 2'-Se-methyl, and the like are more preferred, 2'-O-methyl, 2'-O-ethyl, 2'-fluoro, and the like are still more preferred, and 2'-O-methyl and 2'-O-ethyl are most preferred.

In addition, the preferred range of the modifying group in the sugar moiety-modified nucleotide can also be defined based on its size, and a modifying group with a size corresponding to from the size of fluoro to the size of —O-butyl is preferred, and a modifying group with a size corresponding to from the size of —O-methyl to the size of —O-ethyl is more preferred.

The alkyl in the modifying group in the sugar moiety-modified nucleotide has the same definition as the alkyl having 1 to 6 carbon atoms in the cationic lipid of the present invention.

Examples of the alkenyl in the modifying group in the sugar moiety-modified nucleotide include alkenyl having 3 to 6 carbon atoms, for example, allyl, 1-propenyl, butenyl, pentenyl, hexenyl, and the like.

Examples of the halogen in the modifying group in the sugar moiety-modified nucleotide include a fluorine atom, a chlorine atom, a bromine atom, an iodine atom, and the like.

Examples of the amino acid in the amino acid residue include aliphatic amino acids (specifically, glycine, alanine, valine, leucine, isoleucine, and the like), hydroxy amino acids (specifically, serine, threonine, and the like), acidic amino acids (specifically, aspartic acid, glutamic acid, and the like), acidic amino acid amides (specifically, asparagine, glutamine, and the like), basic amino acids (specifically, lysine, hydroxylysine, arginine, ornithine, and the like), sulfur-containing amino acids (specifically, cysteine, cystine, methionine, and the like), imino acids (specifically, proline, 4-hydroxy proline, and the like), and the like.

Examples of the substituent in the substituted alkyl and the substituted alkenyl in the modifying group in the sugar moiety-modified nucleotide include halogen (having the same definition as described above), hydroxy, sulfanyl, amino, oxo, —O-alkyl (the alkyl moiety of the —O-alkyl has the same definition as that of the above-described alkyl), —S-alkyl (the alkyl moiety of the —S-alkyl has the same definition as that of the above-described alkyl), —NH-alkyl (the alkyl moiety of the —NH-alkyl has the same definition as that of the above-described alkyl), dialkylaminooxy (the two alkyl moieties of the dialkylaminooxy may be the same or different, and have the same definition as that of the above-described alkyl), dialkylamino (the two alkyl moieties of the dialkylamino may be the same or different, and have the same definition as that of the above-described alkyl), dialkylaminoalkyloxy (the two alkyl moieties of the dialkylaminoalkyloxy may be the same or different, and have the same definition as that of the above-described alkyl, and the alkylene moiety means a group obtained by removing one hydrogen atom from the above-described alkyl), and the like, and the number of substituents is preferably 1 to 3.

The phosphodiester bond-modified nucleotide may be any as long as it is a nucleotide in which a part or all of the chemical structure of the phosphodiester bond of the nucleotide is modified or substituted with an arbitrary substituent or substituted with an arbitrary atom, and examples thereof include a nucleotide in which the phosphodiester bond is substituted with a phosphorothioate bond, a nucleotide in which the phosphodiester bond is substituted with a phosphorodithioate bond, a nucleotide in which the phosphodiester bond is substituted with an alkylphosphonate bond, a nucleotide in which the phosphodiester bond is substituted with a phosphoroamidate bond, and the like.

The base-modified nucleotide may be any as long as it is a nucleotide in which a part or all of the chemical structure of the base of the nucleotide is modified or substituted with an arbitrary substituent or substituted with an arbitrary atom, and examples thereof include a nucleotide in which an oxygen atom in the base is substituted with a sulfur atom, a nucleotide in which a hydrogen atom is substituted with an alkyl group having 1 to 6 carbon atoms, a nucleotide in which a methyl group is substituted with a hydrogen atom or an alkyl group having 2 to 6 carbon atoms, a nucleotide in which an amino group is protected by a protective group such as an alkyl group having 1 to 6 carbon atoms or an alkanoyl group having 1 to 6 carbon atoms, and the like.

Furthermore, examples of the nucleotide derivative include those in which another chemical substance such as a lipid, a phospholipid, phenazine, folate, phenanthridine, anthraquinone, acridine, fluorescein, rhodamine, coumarin, or a pigment is added to a nucleotide or a nucleotide derivative in which at least one of the sugar moiety, the phosphodiester bond, and the base is modified. Specific examples thereof include 5'-polyamine-added nucleotide derivatives, cholesterol-added nucleotide derivatives, steroid-added nucleotide derivatives, bile acid-added nucleotide derivatives, vitamin-added nucleotide derivatives, green fluorochrome (Cy3)-added nucleotide derivatives, red fluorochrome (Cy5)-added nucleotide derivatives, fluoroscein (6-FAM)-added nucleotide derivatives, biotin-added nucleotide derivatives, and the like.

In addition, in the nucleic acid to be used in the present invention, the nucleotide or the nucleotide derivative may form, together with another nucleotide or nucleotide derivative within the nucleic acid, a crosslinked structure such as an alkylene structure, a peptide structure, a nucleotide structure, an ether structure, an ester structure, or a structure combined with at least one of these structures.

Preferred examples of the nucleic acid to be used in the present invention include nucleic acids which suppress the expression of the target gene, and more preferred examples thereof include nucleic acids having an activity of suppressing the expression of the target gene by utilizing RNA interference (RNAi).

The target gene in the present invention is not particularly limited as long as it is a gene which produces mRNA and is expressed, however, preferred examples thereof include genes associated with tumor or inflammation, for example, genes which encode proteins such as a vascular endothelial growth factor (hereinafter, abbreviated as "VEGF"), a vascular endothelial growth factor receptor (hereinafter, abbreviated as "VEGFR"), a fibroblast growth factor, a fibroblast growth factor receptor, a platelet-derived growth factor, a platelet-derived growth factor receptor, a liver cell growth factor, a liver cell growth factor receptor, a Kruppel-like factor (hereinafter, abbreviated as "KLF"), an expressed sequence tag (Ets) transcription factor, a nuclear factor, a hypoxia-inducible factor, a cell cycle-associated factor, a chromosomal duplication-associated factor, a chromosomal repair-associated factor, a microtubule-associated factor, a growth signaling pathway-associated factor, a growth-associated transcription factor, and an apoptosis-associated factor, and the like, and specific examples thereof include a VEGF gene, VEGFR gene, a fibroblast growth factor gene, a fibroblast growth factor receptor gene, a platelet-derived growth factor gene, a platelet-derived growth factor receptor gene, a liver cell growth factor gene, a liver cell growth factor receptor gene, a KLF gene, an Ets transcription factor gene, a nuclear factor gene, a hypoxia-inducible factor gene, a cell cycle-associated factor gene, a chromosomal duplication-associated factor gene, a chromosomal repair-associated factor gene, a microtubule-associated factor gene (for example, a CKAP5 gene, etc.), a growth signaling pathway-associated factor gene (for example, a KRAS gene, etc.), a growth-associated transcription factor gene, an apoptosis-associated factor gene (for example, a BCL-2 gene, etc.), and the like.

In addition, as the target gene in the present invention, a gene which is expressed in, for example, the liver, lung, kidney, or spleen is preferred, and a gene which is expressed in the liver is more preferred, and examples thereof include the above-described genes associated with tumor or inflammation, a hepatitis B virus genome, a hepatitis C virus genome, and genes which encode proteins such as an apolipoprotein (APO), hydroxymethyl glutaryl (HMG) CoA reductase, kexin type 9 serine protease (PCSK9), factor XII, a glucagon receptor, a glucocorticoid receptor, a leukotriene receptor, a thromboxane A2 receptor, a histamine H1 receptor, a carbonic anhydrase, an angiotensin converting enzyme, renin, p53, tyrosine phosphatase (PTP), a sodium-dependent glucose transport carrier, a tumor necrosis factor, an interleukin, hepcidin, transthyretin, antithrombin, protein C, or a matriptase enzyme (for example, a TMPRSS6 gene, etc.), and the like.

As the nucleic acid which suppresses the expression of the target gene, any nucleic acid, for example, a double-stranded nucleic acid such as siRNA (short interference RNA) oz miRNA (micro RNA), a single-stranded nucleic acid such as shRNA (short hairpin RNA), an antisense nucleic acid, or a ribozyme, or the like may be used as long as it is, for example, a nucleic acid which contains a base sequence complementary to a part of the base sequence of mRNA of a gene which encodes a protein or the like (target gene), and also suppresses the expression of the target gene, however, a double-stranded nucleic acid is preferred.

A nucleic acid which contains a base sequence complementary to a pare of the base sequence of mRNA of the target gene is referred to as an antisense strand nucleic acid, and a nuclei c acid which contains a base sequence complementary to the base sequence of the antisense strand nucleic acid is also referred to as a sense strand nucleic acid. The sense strand nucleic acid refers to a nucleic acid which can form a double-stranded forming region by pairing with the antisense strand nucleic acid such as a nucleic acid itself which is composed of a part of the base sequence of the target gene.

The double-stranded nucleic acid refers to a nucleic acid which has a double-stranded forming region by pairing two single strands. The double-stranded forming region refers to a region where a double strand is formed by the base pairing of nucleotides or derivatives thereof which constitute a double-stranded nucleic acid. The base pairs which constitute the double-stranded forming region are typically 15 to 27 base pairs, preferably 15 to 25 base pairs, more preferably 15 to 23 base pairs, still more preferably 15 to 21 base pairs, and particularly preferably 15 to 19 base pairs.

As the anti sense strand nucleic acid in the double-stranded forming region, for example, a nucleic acid which is composed of a part of the sequence of the target gene mRNA, or a nucleic acid which is obtained by substitution, deletion, or addition of 1 to 3 bases, preferably 1 to 2 bases, more preferably 1 base in the nucleic acid and has an activity of suppressing the expression of the target protein is preferably used. The single-stranded nucleic acid which constituents a double-stranded nucleic acid is composed of a succession of typically 15 to 30 bases (nucleosides), preferably 15 to 29 bases, more preferably 15 to 27 bases, still more preferably 15 to 25 bases, particularly preferably 17 to 23 bases, and most preferably 19 to 21 bases.

The nucleic acid in either or both of the antisense strand and the sense strand which constitute a double-stranded nucleic acid may have an additional nucleic acid which does not form a double strand contiguous with the double-stranded forming region on the 3' side or the 5' side. Such a region which does not form a double strand is also referred to as a protrusion (overhang).

As the double-stranded nucleic acid having a protrusion, for example, a double-stranded nucleic acid having a protrusion composed of 1 to 4 bases, typically 1 to 3 bases at the 3' end or the 5' end of at least one single strand is used, however, a double-stranded nucleic acid having a protrusion composed of 2 bases is preferably used, and a double-stranded nucleic acid having a protrusion composed of dTdT or (U is more preferably used. A protrusion may be present on only the antisense strand, only the sense strand, and both of the antisense strand and the sense strand, however, a double-stranded nucleic acid in which a protrusion is present on both of the antisense strand and the sense strand is preferably used.

In addition, a sequence which is contiguous with the double-stranded forming region and partially or completely matches with the base sequence of the target gene mRNA, or a sequence which is contiguous with the double-stranded forming region and partially or completely matches with the base sequence of the complementary strand of the target gene mRNA may also be used. Furthermore, as the nucleic acid which suppresses the expression of the target gene, for example, a nucleic acid molecule which forms the above-described double-stranded nucleic acid by the activity of a ribonuclease such as Dicer (WO2005/089287), a double-stranded nucleic acid which does not, have a protrusion at the 3' end or the 5' end, or the like can also be used.

In addition, when the above-described double-stranded nucleic acid is siRNA, preferably, at least a sequence of bases (nucleosides) at the positions 1 to 17 from the 5' end side to the 3' end side of the antisense strand is a base sequence complementary to a sequence composed of 17 consecutive bases of the target gene mRNA. More preferably, a sequence of bases at the positions 1 to 19 from the 5' end side to the 3' end side of the antisense strand is a base sequence complementary to a sequence composed of consecutive 19 bases of the target gene mRNA, or a sequence of bases at the positions 1 to 21 is a base sequence complementary to a sequence composed of 21 consecutive bases of the target gene mRNA, or a sequence of bases at the positions 2 to 25 is a base sequence complementary to a sequence composed of 25 consecutive bases of the target gene mRNA.

Furthermore, when the nucleic acid to be used in the present invention is siRNA, preferably 10 to 70%, more preferably 15 to 60%, and still more preferably 20 to 50% of the sugars in the nucleic acid are riboses substituted with a modifying group at the 2' position. In the present invention, the ribose substituted with a modifying group at the 2' position means a ribose in which the hydroxyl group at the 2' position thereof is substituted with a modifying group. The configuration may be the same as or different from the configuration of the hydroxyl group at the 2' position of the ribose, however, it is preferred that the configuration is the same as the configuration of the hydroxyl group at the 2' position of the ribose. Examples of the modifying group in the ribose substituted at the 2' position include those exemplified in the definition of the modifying group in the 2'-modified nucleotide in the sugar moiety-modified nucleotide and a hydrogen atom. Preferred examples thereof 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, and the like, more preferred examples thereof include 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom, and the like, still more preferred examples thereof include 2'-O-methyl, 2'-O-ethyl, 2'-fluoro, a hydrogen atom, and the liked, and most preferred examples thereof include 2'-O-methyl and 2'-O-fluoro.

The nucleic acid to be used in the present invention includes derivatives in which an oxygen atom or the like contained in the phosphate moiety, the ester moiety, or the like in the structure of the nucleic acid is substituted with another atom, for example, a sulfur atom or the like.

In addition, in the sugar which binds to the base at the 5' end of each of the antisense strand and the sense strand, the hydroxyl group at the 5' position may be modified with a phosphate group or the above-described modifying group, or a group which is converted into a phosphate group or the above-described modifying group by an in vivo nuclease or the like.

In addition, in the sugar which binds to the base at the 3' end of each of the antisense strand and the sense strand, the hydroxyl group at the 3' position may be modified with a phosphate group or the above-described modifying group, or a group which is converted into a phosphate group or the above-described modifying group by an in vivo nuclease or the like.

The single-stranded nucleic acid may be any as long as it is a nucleic acid which has a sequence complementary to a sequence composed of, for example, consecutive 15 to 27 bases (nucleosides), preferably consecutive 15 to 25 bases, more preferably consecutive 15 to 23 bases, still more preferably consecutive 15 to 21 bases, and particularly preferably consecutive 15 to 19 bases of the target gene, or a nucleic acid which is obtained by substitution, deletion, or addition of 1 to 3 bases, preferably 1 to 2 bases, more preferably 1 base in the nucleic acid and has an activity of suppressing the expression of the target protein. The single-stranded nucleic acid is composed of a succession of preferably 15 to 30 bases (nucleosides), more preferably 15 to 27 bases, and still more preferably 15 to 25 bases, and in particular, a single-stranded nucleic acid composed of 15 to 23 bases is suitably used.

As the single-stranded nucleic acid, a single-stranded nucleic acid obtained by connecting the antisense strand and the sense strand, which constitute the above-described double-stranded nucleic acid, via a spacer sequence (spacer oligonucleotide) may be used. As the spacer oligonucleotide, a single-stranded nucleic acid molecule composed of 6 to 12 bases is preferred, and the sequence thereof on the 5' end side is preferably a UU sequence. Examples of the spacer oligonucleotide include a nucleic acid composed of a UUCAAGAGA sequence. As for the connection order of the antisense strand and the sense strand connected via the spacer oligonucleotide, either strand may be located on the 5' side. The single-stranded nucleic acid is preferably a single-stranded nucleic acid, for example, shRNA which has a double-stranded forming region with a stem-loop structure, etc. The single-stranded nucleic acid such as shRNA is typically 50 to 70 bases long.

A nucleic acid, which has a length of 70 bases or less, preferably 50 bases or less, more preferably 30 bases or less, and is designed so that it forms the above-described single-stranded nucleic acid or double-stranded nucleic acid by the activity of a ribonuclease or the like, may be used.

Incidentally, the nucleic acid to be used in the present invention can be produced by using a known RNA or DNA synthesis method, and an RNA or DNA modification method.

The composition of the present invention is a composition containing the cationic lipid of the present invention and a nucleic acid, and examples thereof include a composition containing a complex between the cationic lipid of the present invention and a nucleic acid or a complex between a combination of a neutral lipid and/or a polymer with the cationic lipid of the present invention and a nucleic acid, a composition containing the complex and a lipid membrane which encapsulates the complex, and the like. The lipid membrane may be a lipid monolayer membrane (lipid monomolecular membrane) or a lipid bilayer membrane (lipid bimolecular membrane). Incidentally, in the lipid membrane, the cationic lipid of the present invention, a neutral lipid and/or a polymer may be incorporated. In addition, in the complex and/or the lipid membrane, a cationic lipid other than the cationic lipid of the present invention may be incorporated.

In addition, additional examples of the composition of the present invention include a composition containing a complex between a cationic lipid other than the cationic lipid of the present invention and a nucleic acid or a complex between a combination of a neutral lipid and/or a polymer with a cationic lipid other than the cationic lipid of the present invention and a nucleic acid, and a lipid membrane which encapsulates the complex, wherein the cationic lipid of the present invention is incorporated in the lipid membrane, and the like. The lipid membrane in this case may also be a lipid monolayer membrane (lipid monomolecular membrane) or a lipid bilayer membrane (lipid bimolecular membrane). Further, in the lipid membrane, a cationic lipid other than the cationic lipid of the present invention, a neutral lipid, and/or a polymer may be incorporated.

In the composition of the present invention, a composition containing a complex between the cationic lipid of the present invention and a nucleic acid; a composition containing a complex between the cationic lipid of the present invention and a nucleic acid, and a lipid membrane which encapsulates the complex, wherein the cationic lipid of the present invention is incorporated in the lipid membrane; and a composition containing a complex between a cationic lipid other than the cationic lipid of the present invention and a nucleic acid, and a lipid membrane which encapsulates the complex, wherein the cationic lipid of the present invention is incorporated in the lipid membrane are more preferred, a composition containing a complex between the cationic lipid of the present invention and a nucleic acid; and a composition containing a complex between the cationic lipid of the present invention and a nucleic acid, and a lipid membrane which encapsulates the complex, wherein the cationic lipid of the present invention is incorporated in the lipid membrane are still more preferred, and a composition containing a complex between the cationic lipid of the present invention and a nucleic acid, and a lipid membrane which encapsulates the complex, wherein the cationic lipid of the present invention is incorporated in the lipid membrane is most preferred. Incidentally, in any case, in the lipid membrane, a neutral lipid and/or a polymer may be incorporated. In addition, in the complex and/or the lipid membrane, a cationic lipid other than the cationic lipid of the present invention may be incorporated.

Examples of the form of the complex include a complex between a nucleic acid and a membrane composed of a lipid monolayer (single molecular layer) (reversed micelle); a complex between a nucleic acid and a liposome; a complex between a nucleic acid and a micelle, and the like, and preferred examples thereof include a complex between a nucleic acid and a membrane composed of a lipid monolayer; and a complex between a nucleic acid and a liposome.

Examples of the composition containing a complex and a lipid membrane which encapsulates the complex include a composition containing the complex and a liposome which encapsulates the complex with a lipid bilayer membrane and the like.

Incidentally, in the composition of the present invention, one or more types of the cationic lipid of the present invention may be used, and also, a cationic lipid other than the cationic lipid of the present invention may be mixed with the cationic lipid of the present invention.

Examples of the cationic lipid other than the cationic lipid of the present invention include N-[1-(2,3-dioleyloxy)propyl]-N,N,N-trimethylammonium chloride (DOTMA), N-(2,3-di-(9-(Z)-octadecenoyloxy))-prop-1-yl-N,N,N-trimethylammonium chloride (DOTAP), and the like disclosed in Japanese Published Unexamined Patent Application No. Shou 61-161246 (U.S. Pat. No. 5,049,386), N-[1-(2,3-dioleyloxypropyl)]-N,N-dimethyl-N-hydroxyethyl ammonium bromide (DORIE), 2,3-dioleoyloxy-N-[2-(sperminecarboxyamido)ethyl]-N,N-dimethyl-1-propanaminium trifluoroacetate (DOSPA), and the like disclosed in WO91/016024 and WO97/019675, DLinDMA and the like disclosed in WO2005/121348, DLin-K-DMA disclosed in WO2009/086558, (3R,4R)-3,4-bis((Z)-hexadec-9-enyloxy)-1-methylpyrrolidine, N-methyl-N,N-bis(2-((Z)-octadec-6-enyloxy)ethyl)amine, and the like disclosed in WO2011/136368, and the like, preferred examples thereof include cationic lipids having a tertiary amine moiety with two unsubstituted alkyl groups or a quaternary ammonium moiety with three unsubstituted alkyl groups, such as DOTMA, DOTAP, DORIE, DOSPA, 1,2-dilinoleyloxy-N,N-dimethylaminopropane (DLinDMA), and 2,2-dilinoleyl-4-dimethylaminomethyl-[1,3]-dioxolane (DLin-K-DMA), and more preferred examples thereof include cationic lipids having the tertiary amine moiety. It is more preferred that the unsubstituted alkyl group of the tertiary amine moiety and the quaternary ammonium moiety is a methyl group.

Incidentally, the composition of the present invention can contain a nucleic acid, however, it can also contain a compound chemically close to a nucleic acid.

The composition of the present invention can be produced by known production methods or modified methods thereof and may be a composition produced by any production method. For example, in the production of a composition containing a liposome as one of the compositions, a known liposome preparation method can be applied. Examples of the known liposome preparation method include a liposome preparation method by Bangham, et al. (see *The Journal of Molecular Biology* (*J. Mol. Biol.*), 1965, Vol. 13, pp. 238-252), an ethanol injection method (see *The Journal of Cell Biology* (*J. Cell. Biol.*)", 1975, vol. 66, pp. 621-634), a French press method (see *The FEBS Letters* (*FEBS Lett.*), 1979, Vol. 99, pp. 210-214), a freeze-thawing method (see *The Archives of Biochemistry and Biophysics* (*Arch. Biochem. Biophys.*), 1981, Vol. 212, pp. 186-194), a reverse phase evaporation method (see *The Proceedings of the National Academy of Sciences of the United States of America* (*Proc. Natl. Acad. Sci. USA*), 1978, Vol. 75, pp. 4194-4198), a pH gradient method (see, for example, Japanese Examined Patent Publications Nos. 2572554 and 2659136, etc.), and the like. As a solution for dispersing a liposome in the production of a liposome, for example, water, an acid, an alkali, any of a variety of buffer solutions, saline, an amino acid infusion, or the like can be used. In addition, in the production of a liposome, it is also possible to add, for example, an antioxidant such as citric acid, ascorbic acid, cysteine, or ethylenediaminetetraacetic acid (EDTA), an isotonic agent such as glycerin, glucose, or sodium chloride, or the like. In addition, a liposome can also be produced by, for example, dissolving the cationic lipid of the present invention, a mixture of the cationic lipid of the present invention and a cationic lipid other than the cationic lipid of the present invention, or the like in an organic solvent such as ethanol, distilling off the solvent, adding saline or the like, followed by stirring the mixture by shaking, thereby forming a liposome.

In addition, the composition of the present invention can be produced by, for example, a method in which the cationic lipid of the present invention or a mixture of the cationic lipid of the present invention and a cationic lipid other than the cationic lipid of the present invention is dissolved in chloroform in advance; subsequently, an aqueous solution of a nucleic acid and methanol are added thereto, followed by mixing, thereby forming a cationic lipid/nucleic acid complex; furthermore, the chloroform layer is taken out; a polyethylene glycolated phospholipid, a neutral lipid, and water are added thereto, thereby forming a water-in-oil (W/O) emulsion; and the formed emulsion is treated by a reverse phase evaporation method (see Japanese Patent Domestic Announcement No. 2002-508765), a method in which a nucleic acid is dissolved in an acidic aqueous electrolyte solution; for example, the cationic lipid of the present invention or a mixture of the cationic lipid of the present invention and a cationic lipid other than the cationic lipid of the present invention (in ethanol) is added thereto; the concentration of ethanol is decreased to 20 v/v %, thereby preparing a liposome encapsulating the nucleic acid, followed by sizing filtration and dialysis to remove an excess amount of ethanol; and thereafter, the sample is further dialyzed while increasing the pH, thereby removing the nucleic acid adhering to the surface of the composition (see Japanese Patent Domestic Announcement No. 2002-501511 and *Biochimica et Biophysics Acta,* 2001, Vol. 1510, pp. 152-166), or the like.

Among the compositions of the present invention, a composition containing a complex between the cationic lipid of the present invention and a nucleic acid, or a complex between a combination of a neutral lipid and/or a polymer with the cationic lipid of the present invention and a nucleic acid and a liposome containing a lipid bilayer membrane which encapsulates the complex can be produced according to the production method described in, for example, WO02/28367, WO2006/080118, or the like.

In addition, among the compositions of the present invention, for example, a composition containing a complex between the cationic lipid of the present invention and a nucleic acid, or a complex between a combination of a neutral lipid and/or a polymer with the cationic lipid of the present invention and a nucleic acid, and a lipid membrane which encapsulates the complex, a composition containing a complex between a cationic lipid other than the cationic lipid of the present invention and a nucleic acid, or a complex between a combination of a neutral lipid and/or a polymer with a cationic lipid other than the cationic lipid of the present invention and a nucleic acid, and a lipid membrane which encapsulates the complex, wherein the cationic lipid of the present invention is incorporated in the lipid membrane, or the like can be obtained by producing each complex according to the production method described in WO02/28367, WO2006/080118, or the like, dispersing the complex in water or an aqueous solution of 0 to 20% ethanol without dissolving the complex (A solution), and separately dissolving each lipid membrane component in, for example, an aqueous solution of ethanol (B solution), mixing A solution and B solution in equal amounts, and further adding water thereto appropriately. Incidentally, as the cationic lipid in A solution or B solution, one or more types of the cationic lipid of the present invention or cationic lipids other than the cationic lipid of the present invention may be used, and also, the cationic lipid of the present invention and a cationic lipid other than the cationic lipid of the present invention may be mixed with each other and used in combination.

Incidentally, in the present invention, compositions in which during the production and after the production of the composition containing a complex between the cationic lipid of the present invention and a nucleic acid, or a complex between a combination of a neutral lipid and/or a polymer with the cationic lipid of the present invention and a nucleic acid, and a lipid membrane which encapsulates the complex, the composition containing a complex between a cationic lipid other than the cationic lipid of the present invention and a nucleic acid, or a complex between a combination of a neutral lipid and/or a polymer with a cationic lipid other than the cationic lipid of the present invention and a nucleic acid, and a lipid membrane which encapsulates the complex, wherein the cationic lipid of the present invention is incorporated in the lipid membrane, and the like, the structures of the complex and the membrane are displaced due to an electrostatic interaction between the nucleic acid in the complex and the cationic lipid in the lipid membrane or fusion between the cationic lipid in the complex and the cationic lipid in the lipid membrane are also included in the composition containing a complex between the cationic lipid of the present invention and a nucleic acid, or a complex between a combination of a neutral lipid and/or a polymer with the cationic lipid of the present invention and a nucleic acid, and a lipid membrane which encapsulates the complex, the composition containing a complex between a cationic lipid other than the cationic lipid of the present invention and a nucleic acid, or a complex between a combination of a neutral lipid and/or a polymer with a cationic lipid other than the cationic lipid of the present invention and a nucleic acid, and a lipid membrane which encapsulates the complex, wherein the cationic lipid of the present invention is incorporated in the lipid membrane, and the like, respectively.

By producing a complex between a nucleic acid (having the same definition as described above), preferably a double-stranded nucleic acid, and a liposome containing the cationic lipid of the present invention and/or a cationic lipid other than the cationic lipid of the present invention according to the production method described in WO02/28367, WO2006/080118, or the like, dispersing the complex in water or an aqueous solution of 0 to 20% ethanol without dissolving the complex (A solution), and separately dissolving the cationic lipid of the present invention and/or a cationic lipid other than the cationic lipid of the present invention in an aqueous solution of ethanol (B solution), mixing A solution and B solution in equal amounts or a volume ratio of 1/1, or further adding water thereto appropriately, a composition containing the nucleic acid and the cationic lipid can be obtained. The composition is preferably a composition containing a complex between a cationic lipid and a nucleic acid and a lipid membrane which encapsulates the complex, and more preferably a composition containing a complex between the nucleic acid and a membrane composed of a lipid monolayer containing the cationic lipid (reversed micelle) and a lipid membrane which encapsulates the complex. In these cases, the lipid membrane may be a lipid monolayer membrane (lipid monomolecular membrane) or a lipid bilayer membrane (lipid bimolecular membrane).

In addition, the liposome in the complex between the nucleic acid and the liposome as disclosed herein is preferably a liposome whose size is adjusted in advance at 10 nm to 400 nm, more preferably 30 nm to 110 nm, and still more preferably 40 nm to 80 nm in terms of an average particle diameter. In addition, in the complex and/or the lipid membrane, a neutral lipid and/or a polymer may be incorporated. In addition, in A solution, the concentration of ethanol may be 20 to 40% as long as the complex between the liposome and the nucleic acid can be formed.

In addition, in place of mixing A solution and B solution in equal amounts, A solution and B solution may be mixed with each other in a ratio so as to attain a concentration of ethanol at which after mixing A solution and B solution, the complex is not dissolved, and the cationic lipid in B solution is not dissolved, and preferably in a ratio at which the complex is not dissolved, the cationic lipid in B solution is not dissolved, and an aqueous solution of ethanol having a concentration of ethanol of 30 to 60% is attained. Alternatively, A solution and B solution may also be mixed with each other in a ratio so as to attain a concentration of ethanol at which after mixing A solution and B solution, the complex is not dissolved, and by further adding water, a concentration of ethanol at which the cationic lipid in B solution is not dissolved is attained.

In the complex between the nucleic acid and the liposome in A solution as disclosed herein, after mixing A solution and B solution and further adding water thereto appropriately, the form is altered to a complex between the membrane composed of the lipid monolayer containing the cationic lipid (reversed micelle) and the nucleic acid. The composition containing the nucleic acid and the cationic lipid obtained by the production method as disclosed herein is preferably a composition containing a complex between a cationic lipid and a nucleic acid and a lipid membrane which encapsulates the complex, and more preferably a composition containing a complex between a membrane composed of a lipid monolayer containing a cationic lipid (reversed micelle) and a nucleic acid and a lipid membrane which encapsulates the complex, the lipid membrane containing the cationic lipid, and its productivity (yield and/or uniformity) is excellent.

In the composition of the present invention, the total number of molecules of the cationic lipid of the present invention in the complex is preferably 0.5 to 4 times, more preferably 1.5 to 3.5 times, and still more preferably 2 to 3 times the number of phosphorus atoms in the nucleic acid. In addition, the total number of molecules of the cationic lipid of the present invention and the cationic lipid other than the cationic lipid of the present invention in the complex is preferably 0.5 to 4 times, more preferably 1.5 to 3.5 times, and still more preferably 2 to 3 times the number of phosphorus atoms in the nucleic acid.

In the composition of the present invention, the total number of molecules of the cationic lipid of the present invention in the composition containing a complex and a lipid membrane which encapsulates the complex is preferably 1 to 10 times, more preferably 2.5 to 9 times, and still more preferably 3.5 to 8 times the number of phosphorus atoms in the nucleic acid. In addition, the total number of molecules of the cationic lipid of the present invention and the cationic lipid other than the cationic lipid of the present invention in the composition is preferably 1 to 10 times, more preferably 2.5 to 9 times, and still more preferably 3.5 to 8 times the number of phosphorus atoms in the nucleic acid.

The neutral lipid may be any lipid selected from a simple lipid, a complex lipid, and a derived lipid, and examples thereof include a phospholipid, a glyceroglycolipid, a sphingoglycolipid, a sphingoid, a sterol, and the like. However, the neutral lipid is not limited thereto.

When the composition of the present invention contains a neutral lipid, the total number of molecules of the neutral lipid is preferably 0.1 to 1.8 times, more preferably 0.3 to 1.2 times, and still more preferably 0.4 to 1.0 time the total number of molecules of the cationic lipid of the present invention and the cationic lipid other than the cationic lipid of the present invention. In any case, in the composition or the present invention, a neutral lipid may be contained in the complex, and al so may be contained in the lipid membrane which encapsulates the complex, and it is more preferred that a neutral lipid is contained in at least the lipid membrane which encapsulates the complex, and it is still more preferred that a neutral lipid is contained in both of the complex and the lipid membrane which encapsulates the complex.

Examples of the phospholipid as the neutral lipid include natural and synthetic phospholipids such as phosphatidylcholines (specifically, soybean phosphatidylcholine, egg yolk phosphatidylcholine (EPC), di stearoyl phosphatidylcholine (DSPC), dipalmitoyl phosphatidylcholine (DPPC), palmitoyloleoyl phosphatidylcholine (POPC), dimyristoyl phosphatidylcholine (DMPC), dioleoyl phosphatidylcholine (DOPC), and the like), phosphatidylethanolamines (specifically, distearoyl phosphatidylethanolamine (DSPE), dipalmitoyl phosphatidylethanolamine (DPPE), dioleoyl phosphatidylethanolamine (DOPE), dimyristoyl phosphoethanolamine (DMPE), 16-0-monomethyl PE, 16-0-dimethyl PE, 18-1-trans PE, palmitoyloleoyl-phosphatidylethanolamine (POPE), 1-stearoyl-2-oleoyl-phosphatidylethanolamine (SOPE), and the like), glycerophospholipids (specifically, phosphatidylserine, phosphatidic acid, phosphatidylglycerol, phosphatidylinositol, palmitoyloleoyl phosphatidylglycerol (POPG), lysophosphatidylcholine, and the like), sphingophospholipids (specifically, sphingomyelin, ceramide phosphoethanolamine, ceramide phosphoglycerol, ceramide phosphoglycerophosphate, and the like), glycerophosphonolipids, sphingophosphonolipids, natural lecithins (specifically, egg yolk lecithin, soybean lecithin, and the like), and hydrogenated phospholipids (specifically, hydrogenated soybean phosphatidylcholine, and the like), and the like.

Examples of the glyceroglycolipid as the neutral lipid include sulfoxyribosyl glyceride, diglycosyl diglyceride, digalactosyl diglyceride, galactosyl diglyceride, glycosyl diglyceride, and the like.

Examples of the sphingoglycolipid as the neutral lipid include galactosyl cerebroside, lactosyl cerebroside, ganglioside, and the like.

Examples of the sphingoid as the neutral lipid include sphingan, icosasphingan, sphingosine, a derivative thereof, and the like. Examples of the derivative include those in which —$NH_2$ of sphingan, icosasphingan, sphingosine, or the like is replaced with —$NHCO(CH_2)xCH_3$ (in the formula, x is an integer of 0 to 18, and preferably 6, 12 or 18), and the like.

Examples of the sterol as the neutral lipid include cholesterol, dihydrocholesterol, lanosterol, β-sitosterol, campesterol, stigmasterol, brassicasterol, ergocasterol, fucosterol, 3β-[N—(N',N'-dimethylaminoethyl)carbamoyl] cholesterol (DC-Chol), and the like.

Examples of the polymer include micelles composed of one or more members selected from a protein, albumin, dextran, polyfect, chitosan, dextran sulfate, a polymer such as poly-L-lysine, polyethyleneimine, polyaspartic acid, a styrene-maleic acid copolymer, an isopropylacrylamide-acrylpyrrolidone copolymer, a polyethylene glycol-modified dendrimer, polylactic acid, polylactic acid polyglycolic acid, or polyethylene glycolated polylactic acid, and a salt thereof, and the like.

Here, the salt of the polymer includes, for example, a metal salt, an ammonium salt, an acid addition salt, an organic amine addition salt, an amino acid addition salt, and the like. Examples of the metal salt include alkali metal salts such as a lithium salt, a sodium salt, and a potassium salt, alkaline earth metal salts such as a magnesium salt and a calcium salt, an aluminum salt, a zinc salt, and the like. Examples of the ammonium salt include salts of ammonium, tetramethylammonium, and the like. Examples of the acid addition salt include inorganic acid salts such as a hydrochloride, a sulfate, a nitrate, and a phosphate, and organic acid salts such as an acetate, a maleate, a fumarate, and a citrate. Examples of the organic amine addition salt include addition salts of morpholine, piperidine, and the like. Examples of the amino acid addition salt include addition salts of glycine, phenylalanine, aspartic acid, glutamic acid, lysine, and the like.

In addition, in any case, the composition of the present invention preferably contains, for example, a lipid derivative or a fatty acid derivative of at least one substance selected from a sugar, a peptide, a nucleic acid, and a water-soluble polymer, or a surfactant or the like. Such a member may be contained in the complex or in the lipid membrane which encapsulates the complex, and it is more preferred that such a member is contained in both of the complex and the lipid membrane which encapsulates the complex.

When the composition of the present invention contains a lipid derivative or a fatty acid derivative of at least one substance selected from a sugar, a peptide, a nucleic acid, and a water-soluble polymer, the total number of molecules of the lipid derivative and the fatty acid derivative of at least one substance selected from a sugar, a peptide, a nucleic acid, and a water-soluble polymer is preferably 0.05 to 0.3 times, more preferably 0.07 to 0.25 times, further more preferably 0.1 to 0.2 times the total number of molecules of the cationic lipid of the present invention and the cationic lipid other than the cationic lipid of the present invention.

As the lipid derivative or the fatty acid derivative of at least one substance selected from a sugar, a peptide, a nucleic acid, and a water-soluble polymer, or the surfactant, preferred is a lipid derivative or a fatty acid derivative of a glycolipid or a water-soluble polymer, and more preferred is a lipid derivative or a fatty acid derivative of a water-soluble polymer. The lipid derivative or the fatty acid derivative of at least one substance selected from a sugar, a peptide, a nucleic acid, and a water-soluble polymer, or the surfactant is preferably a substance having dual properties as follows: a part of the molecule has a property of binding to another constituent component of the composition through, for example, hydrophobic affinity, electrostatic interaction, or the like, and another part of the molecule has a property of binding to a solvent when producing the composition through, for example, hydrophilic affinity, electrostatic interaction, or the like.

Examples of the lipid derivative or the fatty acid derivative of a sugar, a peptide, or a nucleic acid include those obtained by binding a sugar such as sucrose, sorbitol, or lactose, a peptide such as a casein-derived peptide, an egg white-derived peptide, a soybean-derived peptide, or glutathione, or a nucleic acid such as DNA, RNA, a plasmid, siRNA, or ODN to the neutral lipid as exemplified above in the definition of the composition or the cationic lipid of the present invention or a fatty acid such as stearic acid, palmitic acid, myristic acid, or lauric acid, and the like.

Further, the lipid derivative or the fatty acid derivative of a sugar also includes, for example, the glyceroglycolipids and the sphingoglycolipids as exemplified above in the definition of the composition, and the like.

Examples of the lipid derivative or the fatty acid derivative of a water-soluble polymer include those obtained by binding polyethylene glycol, polyglycerin, polyethyleneimine, polyvinyl alcohol, polyacrylic acid, polyacrylamide, an oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like or a derivative thereof to the neutral lipid as exemplified above in the definition of the composition, the cationic lipid of the present invention, or a fatty acid such as stearic acid, palmitic acid, myristic acid, or lauric acid, salts thereof, and the like and salts thereof. More preferred examples thereof include lipid derivatives or fatty acid derivatives of polyethylene glycol, polyglycerin, or the like, and salts thereof. Still more preferred examples thereof include lipid derivatives or fatty acid derivatives of polyethylene glycol, and salts thereof.

Examples of the lipid derivatives or the fatty acid derivatives of polyethylene glycol include polyethylene glycolated lipids [specifically, polyethylene glycol-phosphatidylethanolamines (more specifically, 1,2-distearoyl-sn-glycero-3-phosphoethanolamine-N-[methoxy(polyethylene glycol)-2000] (PEG-DSPE), 1,2-dimyristoyl-sn-glycero-3-phosphoethanolamine-N-[methoxy(polyethylene glycol)-2000](PEG-DMPE), and the like)), polyoxyethylene hydrogenated castor oil 60, CREMOPHOR EL, and the like], polyethylene glycol sorbitan fatty acid esters (specifically, polyoxyethylene sorbitan monooleate, and the like), and polyethylene glycol fatty acid esters, and the like, and more preferred examples thereof include polyethylene glycolated lipids.

Examples of the lipid derivatives or the fatty acid derivatives of polyglycerin include polyglycerolated lipids (specifically, polyglycerin-phosphatidylethanolamines and the like), polyglycerin fatty acid esters, and the like, and more preferred examples thereof include polyglycerolated lipids.

Examples of the surfactant include polyoxyethylene sorbitan monooleates (specifically, Polysorbate 80 and the like), polyoxyethylene polyoxypropylene glycols (specifically, Pluronic F68 and the like), sorbitan fatty acid esters (specifically, sorbitan monolaurate, sorbitan monooleate, and the like), polyoxyethylene derivatives (specifically, polyoxyethylene hydrogenated castor oil 60, polyoxyethylene lauryl alcohol, and the like), glycerin fatty acid esters, polyethylene glycol alkyl ethers, and the like, and preferred examples thereof include polyoxyethylene polyoxypropylene glycols, glycerin fatty acid esters, polyethylene glycol alkyl ethers, and the like.

In addition, the complex and the lipid membrane in the composition of the present invention can also be arbitrarily subjected to surface modification with, for example, a water-soluble polymer, a polyoxyethylene derivative, or the like [see *Stealth Liposomes*, edited by D. D. Lasic and F. Martin, CRC Press Inc., US, 1993, pp. 93-102]. Examples of the water-soluble polymer which can be used for the surface modification include polyethylene glycol, polyglycerin, polyethyleneimine, polyvinyl alcohol, polyacrylic acid, polyacrylamide, an oligosaccharide, dextrin, a water-soluble cellulose, dextran, chondroitin sulfate, chitosan, polyvinylpyrrolidone, polyaspartamide, poly-L-lysine, mannan, pullulan, oligoglycerol, and the like, and preferred examples thereof include dextran, pullulan, mannan, amylopectin, hydroxyethyl starch, and the like. In addition, for the surface modification, a lipid derivative or a fatty acid derivative (having the same definition as described above) of at least one substance selected from a sugar, a peptide, a nucleic acid, and a water-soluble polymer, or the like can be used. The surface modification is one of methods for incorporating a lipid derivative or a fatty acid derivative of at least one substance selected from a sugar, a peptide, a nucleic acid, and a water-soluble polymer, or a surfactant in the complex and the lipid membrane in the composition of the present invention.

In addition, by the covalent binding of a targeting ligand to a polar head residue of the lipid component of the composition of the present invention, the targeting ligand can also be arbitrarily bound directly to the surface of the composition of the present invention (see WO2006/116107).

The average particle diameter of the complex or the lipid membrane which encapsulates the complex in the composition of the present invention may be freely selected as desired, but is preferably adjusted to the average particle diameter described below. Examples of a method for adjusting the average particle diameter include an extrusion method, a method in which a large multilamellar liposome (MLV) or the like is mechanically pulverized (specifically, using Manton-gaulin, a microfluidizer, or the like) (see *Emulsion and Nanosuspensions for the Formulation of Poorly Soluble Drugs*, written and edited by R. H. Muller, S. Benita, and B. Bohm, Scientific Publishers, Stuttgart, Germany, 1998, pp. 267-294), and the like.

As for the size of the complex in the composition of the present invention, the average particle diameter thereof is preferably about 5 nm to 200 nm, more preferably about 20 nm to 150 nm, and still more preferably about 30 nm to 100 nm.

As for the size of the composition (the lipid membrane which encapsulates the complex) of the present invention, the average particle diameter thereof is preferably about 10 nm to 300 nm, more preferably about 30 nm to 200 nm, and still more preferably about 50 nm to 150 nm.

The average particle diameter of the complex or the lipid membrane which encapsulates the complex in the composition of the present invention can be measured by, for example, the dynamic light scattering method.

By introducing the composition of the present invention to a mammalian cell, the nucleic acid in the composition of the present invention can be introduced into the cell.

The introduction of the composition of the present invention to a mammalian cell in vivo may be carried out according to a known transfection procedure which can be carried out in vivo. For example, by intravenously administering the composition of the present invention to mammals including humans, the composition is delivered to, for example, an organ or a site affected by tumor or inflammation, and the nucleic acid in the composition of the present invention can be introduced into the cells in this organ or site where the composition has been delivered. The organ or the site affected by tumor or inflammation is not particularly limited, but examples thereof include stomach, large intestine, liver, lung, spleen, pancreas, kidney, bladder, skin, blood vessel, eye ball, and the like. In addition, by intravenously administering the composition of the present invention to mammals including humans, the composition can be delivered to, for example, the liver, lung, spleen, and/or kidney, and the nucleic acid in the composition of the present invention can be introduced into the cells in the organ or the site where the composition has been delivered. The cells in the liver, lung, spleen, and/or kidney may be any of normal cells, cells associated with tumor or inflammation, and cells associated with other diseases.

If the nucleic acid in the composition of the present invention is a nucleic acid having an activity of suppressing the expression of the target gene by utilizing RNA interference (RNAi), the nucleic acid or the like which suppresses the expression of the target gene can be introduced to mammalian cells in vivo, and the expression of the target gene can be suppressed. The administration target is preferably a human.

In addition, if the target gene in the present invention is, for example, a gene which is expressed in the liver, lung, kidney, or spleen, preferably a gene which is expressed in the liver, the composition of the present invention can be used as a therapeutic agent or a preventive agent for a disease associated with the liver, lung, kidney, or spleen, preferably a therapeutic agent or a preventive agent for a disease associated with the liver.

Namely, the present invention also provides a method for treating a disease associated with the liver, lung, kidney, or spleen, including administering the composition of the present invention described above to a mammal. The administration target is preferably a human, and more preferably a human suffering from a disease associated with the liver, lung, kidney, or spleen.

In addition, the composition of the present invention can also be used as a tool for verifying the effectiveness of suppressing the target gene in an in vivo drug efficacy evaluation model with respect to a therapeutic agent or a preventive agent for a disease associated with the liver, lung, kidney, or spleen.

The composition of the present invention can also be used as a preparation for, for example, stabilizing the above-described nucleic acid in biological components such as blood components (for example, blood, gastrointestinal tract, or the like), reducing side effects, increasing the drug accumulation in a tissue or an organ including the expression site of the target gene, and so on.

When the composition of the present invention is used as a therapeutic agent or a preventive agent for a disease or the like associated with the liver, lung, kidney, or spleen, which is a pharmaceutical preparation, it is desirable t, use an administration route which is most effective for the treatment. Examples thereof include parenteral administration and oral administration such as intraoral administration, intratracheal administration, intrarectal administration, subcutaneous administration, intramuscular administration, or intravenous administration, and preferred examples thereof include intravenous administration and intramuscular administration, and more preferred examples thereof include intravenous administration.

The dose varies depending on the disease conditions or age of the administration target, the administration route, or the like, however, for example, the composition may be administered at a daily dose of about 0.1 μg to 1,000 mg in terms of the nucleic acid.

Examples of a preparation suitable for the intravenous administration or intramuscular administration include an injection, and it is also possible to use a dispersion liquid of the composition prepared by the above-described method as it is in the form of, for example, an injection or the like. However, it can also be used after removing the solvent from the dispersion liquid by, for example, filtration, centrifugation, or the like, or after lyophilizing the dispersion liquid and/or after lyophilizing the dispersion liquid supplemented with an excipient such as mannitol, lactose, trehalose, maltose, or glycine.

In the case of an injection, it is preferred to prepare the injection by mixing, for example, water, an acid, an alkali, any of a variety of buffer solutions, saline, an amino acid infusion, or the like with the above-described dispersion liquid of the composition or the above-described composition obtained by removing the solvent or lyophilization. In addition, it is also possible to prepare the injection by adding an antioxidant such as citric acid, ascorbic acid, cysteine, or EDTA, an isotonic agent such as glycerin, glucose, or sodium chloride, or the like. Further, the injection can also be cryopreserved by adding a cryopreservative such as glycerin.

Next, the present invention is specifically described with reference to Examples, Reference Examples, and Test Examples. However, the present invention is not limited to these Examples, Reference Examples, and Test Examples.

Incidentally, the proton nuclear magnetic resonance spectra ($^1$H NMR) shown in Examples and Reference Examples are those measured at 270 MHz, 300 MHz, 400 MHz, or 500 MHz, and there may be the case where an exchangeable proton is not clearly observed depending on the compound and the measurement conditions. Incidentally, as the expression for the multiplicity of a signal, a conventionally used expression is employed, however, the symbol "br" indicates that the signal is an apparent broad signal.

EXAMPLE 1

Di((9Z,12Z)-octadeca-9,12-dienyl)amine
(Compound B-1)

To ammonia (manufactured by Tokyo Chemical Industry Co., Ltd., about 2 mol/L methanol solution, 18.0 mL, 36.0 mmol), (9Z,12Z)-octadeca-9,12-dienyl methanesulfonate (manufactured by Nu-Chek Prep, Inc., 1.55 g, 4.50 mmol) was added, followed by stirring at 130° C. for 3 hours using a microwave reactor. To the reaction mixture, a saturated sodium hydrogencarbonate aqueous solution was added, and the mixture was extracted 5 times with chloroform. The organic layers were combined, washed with saturated brine, and dried over anhydrous magnesium sulfate. Thereafter, the resultant was filtered and concentrated under reduced pressure, whereby a crude product of (9Z,12Z)-octadeca-9,12-dienylamine was obtained.

To the obtained crude product, (9Z,12Z)-octadeca-9,12-dienyl methanesulfonate (manufactured by Nu-Chek Prep, Inc., 1.24 g, 3.60 mmol) and a 50% sodium hydroxide aqueous solution (1.44 g, 18.0 mmol) were added, followed by stirring at 110° C. for 60 minutes in an oil bath. After cooling to room temperature, the reaction mixture was diluted with ethyl acetate, washed successively with water and saturated brine, and dried over anhydrous magnesium sulfate. Thereafter, the resultant was filtered and concentrated under reduced pressure. The obtained residue was purified by silica gel column chromatography (chloroform/methanol=100/0 to 95/5), whereby Compound B-1 (0.838 g, yield: 36.2%) was obtained.

ESI-MS m/z: 515 (M+H)$^+$; $^1$H-NMR (CDCl$_3$) δ: 0.89 (t, J=6.9 Hz, 6H), 1.30 (br s, 33H), 1.41-1.54 (m, 4H), 2.01-2.09 (m, 8H), 2.59 (t, J=7.2 Hz, 4H), 2.77 (t, J=5.6 Hz, 4H), 5.28-5.43 (m, 8H)

EXAMPLE 2

Di((Z)-octadec-9-enyl)amine (Compound B-2)

Compound B-2 (0.562 g, yield: 36.2%) was obtained in the same manner as in Example 1 by using ammonia (manufactured by Tokyo Chemical Industry Co., Ltd., about 2 mol/L methanol solution, 12.0 mL, 24.0 mmol) and (Z)-octadec-9-enyl methanesulfonate (manufactured by Nu-Chek Prep, Inc., 1.87 g, 5.40 mmol).

ESI-MS m/z: 519 (M+H)$^+$; $^1$H-NMR (CDCl$_3$) δ: 0.88 (t, J=6.7 Hz, 6H), 3.29 (br, 45H), 1.41-1.52 (m, 4H), 1.97-2.05 (m, 8H), 2.58 (t, J=7.2 Hz, 4H), 5.28-5.40 (m, 4H)

EXAMPLE 3

Di((Z)-hexadec-9-enyl)amine (Compound B-3)

Compound B-3 (0.243 g, yield: 36.0%) was obtained in the same manner as in Example 1 by using ammonia (manufactured by SIGMA-ALDRICH Co., Ltd., about 7 mol/L methanol solution, 1.66 mL, 11.6 mmol) and (Z)-hexadec-9-enyl methanesulfonate (manufactured by Nu-Chek Prep, Inc., 0.488 g, 1.46 mmol).

$^1$H-NMR (CDCl$_3$) δ: 0.89 (t, J=6.9 Hz, 6H), 1.24-1.37 (m, 37H), 1.43-1.52 (m, 4H), 1.98-2.05 (m, 8H), 2.58 (t, J=7.2 Hz, 4H), 5.31-5.38 (m, 4H)

EXAMPLE 4

Di((11Z,14Z)-icosa-11,14-dienyl)amine (Compound B-4)

Compound B-4 (0.292 g, yield: 36.6%) was obtained in the same manner as in Example 1 by using ammonia (manufactured by SIGMA-ALDRICH Co., Ltd., about 7 mol/L methanol solution, 1.60 mL, 11.2 mmol) and (11Z,14Z)-icosa-11,14-dienyl methanesulfonate (manufactured by Nu-Chek Prep, Inc., 0.521 g, 1.40 mmol).

$^1$H-NMR (CDCl$_3$) δ: 0.89 (t, J=6.8 Hz, 6H), 1.24-1.39 (m, 41H), 1.43-1.51 (m, 4H), 2.02-2.08 (m, 8H), 2.58 (t, J=7.3 Hz, 4H), 2.77 (t, J=6.7 Hz, 4H), 5.30-5.41 (m, 8H)

EXAMPLE 5

3-(Dimethylamino) propyl di((9Z,12Z)-octadeca-9,12-dienyl)carbamate (Compound A-1)

Compound B-1 (1.35 g, 2.63 mmol) obtained in Example 1 was dissolved in chloroform (18 mL), and 3-(dimethylamino) propyl 4-nitrophenyl carbonate hydrochloride (Compound VI-1) (1.20 g, 3.94 mmol) synthesized according to the method described in *Journal of American Chemical Society* (*J. Am. Chem. Soc.*), 1981, Vol. 103, pp. 4194-4199 and triethylamine (1.47 mL, 10.5 mmol) were added thereto, followed by stirring at 110° C. for 60 minutes using a microwave reactor. To the reaction mixture, Compound VI-1 (200 mg, 0.658 mmol) was added, followed by stirring at 110° C. for 20 minutes using a microwave reactor. The reaction mixture was diluted with chloroform, washed three times with a 1 mol/L sodium hydroxide aqueous solution and then washed with saturated brine, and thereafter dried over anhydrous magnesium sulfate. Subsequently, the resultant was filtered and concentrated under reduced pressure. The obtained residue was dissolved in a small amount of n-hexane/ethyl acetate (1/4), and the solution was adsorbed on an amino-modified silica gel pad. Then, the target material was eluted with n-hexane/ethyl acetate (1/4), and concentrated under reduced pressure. The resulting residue was purified by silica gel column chromatography (chloroform/methanol=100/0 to 95/5), whereby Compound A-1 (1.39 g, yield: 82.2%) was obtained.

ESI-MS m/z: 644 (M+H)$^+$; $^1$H-NMR (CDCl$_3$) δ: 0.89 (t, J=6.7 Hz, 6H), 1.29 (br s, 32H), 1.45-1.56 (m, 4H), 1.74-1.85 (m, 2H), 2.00-2.09 (m, 8H), 2.23 (s, 6H), 2.35 (t, J=7.4 Hz, 2H), 2.77 (t, J=5.8 Hz, 4H), 3.13-3.23 (m, 4H), 4.10 (t, J=6.4 Hz, 2H), 5.28-5.43 (m, 8H)

EXAMPLE 6

3-(Dimethylamino)propyl di((Z)-octadec-9-enyl) carbamate (Compound A-2)

Compound A-2 (0.267 g, yield: 88.7%) was obtained in the same manner as in Example 5 by using Compound B-2 (0.156 g, 0.301 mmol) obtained in Example 2 in place of Compound B-1.

ESI-MS m/z: 648 (M+H)$^+$; $^1$H-NMR (CDCl$_3$) δ: 0.88 (t, J=6.6 Hz, 6H), 1.28 (br s, 44H), 1.45-1.55 (m, 4H), 1.75-1.85 (m, 2H), 1.97-2.04 (m, 8H), 2.23 (s, 6H), 2.34 (t, J=7.6 Hz, 2H), 3.13-3.24 (m, 4H), 4.10 (t, J=6.4 Hz, 2H), 5.28-5.40 (m, 4H)

EXAMPLE 7

3-(Dimethylamino)propyl di(Z)-hexadec-9-enyl) carbamate (Compound A-3)

Compound A-3 (0.116 g, yield: 55.2%) was obtained in the same manner as in Example 5 by using Compound 3-3 (0.164 g, 0.355 mmol) obtained in Example 3 in place of Compound B-1.

ESI-MS m/z: 592 (M+H)+; $^1$H-NMR (CDCl$_3$) δ: 0.88 (t, J=6.9 Hz, 6H), 1.21-1.38 (m, 38H), 1.47-1.54 (m, 4H), 1.75-1.83 (m, 2H), 2.00-2.04 (m, 8H), 2.22 (s, 6H), 2.34 (t, J=7.4 Hz, 2H), 3.11-3.24 (m, 4H), 4.10 (t, J=6.4 Hz, 2H), 5.30-5.38 (m, 4H)

EXAMPLE 8

3-(Dimethylamino)propyl di((11Z,14Z)-icosa-11,14-dienyl)carbamate (Compound A-4)

Compound A-4 (0.290 g, yield: 82.2%) was obtained in the same manner as in Example 5 by using Compound B-4 (0.288 g, 0.505 mmol) obtained in Example 4 in place of Compound B-1.

ESI-MS m/z: 700 (M+H)$^+$; $^1$H-NMR (CDCl$_3$) δ: 0.89 (L, J=6.8 Hz, 6H), 1.21-1.40 (m, 40H), 1.46-1.54 (m, 4H), 1.76-1.83 (m, 2H), 2.02-2.08 (m, 8H), 2.23 (s, 6H), 2.35 (t, J=7.6 Hz, 2H), 2.77 (t, J=6.7 Hz, 4H), 3.10-3.24 (m, 4H), 4.10 (t, J=6.4 Hz, 2H), 5.30-5.41 (m, 8H)

EXAMPLE 9

2-(Dimethylamino)ethyl di((9Z,12Z)-octadeca-9,12-dienyl)carbamate (Compound A-5)

Compound A-5 (0.184 g, yield: 70.0%) was obtained in the same manner as in Example 5 by using Compound B-1 (0.215 g, 0.418 mmol) obtained in Example 1 and 2-(dimethylamino)ethyl 4-nitrophenyl carbonate hydrochloride (Compound VI-2) (0.162 g, 0.557 mmol) in place of Compound VI-1.

ESI-MS m/z: 630 (M+H)$^+$; $^1$H-NMR (CDCl$_3$) δ: 0.89 (t, J=6.8 Hz, 6H), 1.12-1.39 (m, 32H), 1.45-1.54 (m, 4H), 2.00-2.07 (m, 3H), 2.28 (s, 6H), 2.57 (t, J=7.2 Hz, 2H), 2.77 (t, J=6.7 Hz, 4H), 3.11-3.24 (m, 4H), 4.17 (t, J=6.7 Hz, 2H), 5.28-5.41 (m, 8H)

REFERENCE EXAMPLE 1

5-Amino-N,N-di((9Z,12Z)-octadeca-9,12-dienyl)pentanamide (Compound XI-1)

Compound B-1 (150 mg, 0.292 mmol) obtained in Example 1 was dissolved in chloroform (4 mL), and 5-(tert-butoxycarbonylamino)pentanoic acid (manufactured by Tokyo Chemical Industry Co., Ltd., 95 mg, 0.438 mmol), diisopropylethylamine (0.255 mL, 1.46 mmol), and HATU (O-(7-azabenzotriazol-1-yl)-N,N,N',N'-tetramethyluronium hexafluorophosphate) (manufactured by Aldrich Co., Ltd., 222 mg, 0.584 mmol) were added thereto, followed by stirring at room temperature for 4 hours. To the reaction mixture, a saturated sodium hydrogen carbonate aqueous solution was added, and the aqueous layer was extracted with ethyl acetate. The organic layer was washed successively with water and saturated brine, and dried over anhydrous magnesium sulfate. Thereafter, the resultant was filtered and concentrated under reduced pressure. The obtained residue was purified by silica gel column chromatography (chloroform/methanol=100/0 to 97/3), whereby tert-butyl 5-(di((9Z,12Z)-octadeca-9,12-dienyl)amino)-5-oxopentylcarbamate was obtained.

tert-Butyl 5-(di((9Z,12Z)-octadeca-9,12-dienyl)amino)-5-oxopentylcarbamate was dissolved in dichloromethane (4 ml), and trifluoroacetic acid (0.450 mL, 5.84 mmol) was added thereto, followed by stirring at room temperature for 4 hours. To the reaction mixture, a saturated sodium hydrogen carbonate aqueous solution was added, and the aqueous layer was extracted with chloroform. The organic layer was washed with saturated brine, and dried over anhydrous magnesium sulfate. Thereafter, the resultant was filtered and concentrated under reduced pressure. The obtained residue was purified by silica gel column chromatography (chloroform/methanol=100/0 to 90/10), whereby Compound XI-1 (124 mg, yield: 96.1%) was obtained.

ESI-MS m/z: 614 (M+H)$^+$; $^1$H-NMR (CDCl$_3$) δ: 0.89 (t, J=6.8 Hz, 6H), 1.28-1.38 (m, 32H), 1.43-1.57 (m, 6H), 1.63-1.73 (m, 2H), 2.05 (q, J=7.0 Hz, 8H), 2.30 (t, J=7.2 Hz, 2H), 2.71 (t, J=7.2 Hz, 2H), 2.77 (t, J=6.2 Hz, 4H), 3.19 (t, J=7.7 Hz, 2H), 3.28 (t, J=7.7 Hz, 2H), 5.26-5.43 (m, 8H)

REFERENCE EXAMPLE 2

5-(Dimethylamino)-N,N-di((9Z,12Z)-octadeca-9,12-dienyl)pentanamide (Compound XI-2)

Compound XI-1 (90.0 mg, 0.147 mmol) obtained in Reference Example 1 was dissolved in 1,2-dichloroethane (2 mL) and methanol (2 mL), and formaldehyde (0.219 mL, 2.94 mmol) and sodium triacetoxyborohydride (manufactured by Acros Organics, 311 mg, 1.47 mmol) were added thereto, followed by stirring at room temperature for 5 hours. To the reaction solution, a saturated sodium hydrogen carbonate aqueous solution was added, and the aqueous layer was extracted with ethyl acetate. The organic layer was washed with a saturated sodium chloride aqueous solution, and dried over anhydrous magnesium sulfate. Thereafter, the resultant was filtered and concentrated under reduced pressure. The obtained residue was purified by silica gel column chromatography (chloroform/methanol=100/0 to 75/25), whereby Compound XI-2 (88.2 mg, yield: 93.9%) was obtained.

ESI-MS m/z: 642 (M+H)$^+$; $^1$H-NMR (CDCl$_3$) δ: 0.89 (t, J=7.0 Hz, 6H), 3.26-1.38 (m, 32H), 1.46-1.71 (m, 8H), 2.05 (q, J=7.0 Hz, 8H), 2.22 (s, 6H), 2.29 (q, J=7.0 Hz, 4H), 2.77 (L, J=6.2 Hz, 4H), 3.19 (t, J=7.9 Hz, 2H), 3.28 (t, J=7.7 Hz, 2H), 5.28-5.42 (m, 8H)

REFERENCE EXAMPLE 3

3-Aminopropyl di((9Z,12Z)-octadeca-9,12-dienyl)carbamate (Compound XI-3)

Compound B-1 (146 mg, 0.284 mmol) obtained in Example 1 was dissolved in N,N-dimethylformamide (5 mL), and tert-butyl 3-((4-nitrophenoxy)carbonyloxy)propylcarbamate (145 mg, 0.426 mmol) synthesized according to the method described in *Journal of American Chemical Society* (*J. Am. Chem. Soc.*), 1981, Vol. 103, pp. 4194-4199 and triethylamine (0.158 mL, 1.14 mmol) were added thereto, followed by stirring overnight at room temperature. To the reaction mixture, water was added, and the aqueous layer was extracted with ethyl acetate. The organic layer was washed successively with water and saturated brine, and dried over anhydrous magnesium sulfate. Thereafter, the resultant was filtered and concentrated under reduced pressure. The obtained residue was purified by silica gel column chromatography (chloroform/methanol=100/0 to 98/2), whereby 3-((N-butoxycarbonyl)amino)propyl di((9Z,12Z)-octadeca-9,12-dienyl)carbamate was obtained.

3-((N-Butoxycarbonyl)amino)propyl di((9Z,12Z)-octadeca-9,12-dienyl)carbamate was dissolved in dichloromethane (4 mL), and trifluoroacetic acid (0.242 mL, 3.13 mmol) was added thereto, followed by stirring at room temperature for 8 hours. To the reaction mixture, a saturated sodium hydrogen carbonate aqueous solution was added, and the aqueous layer was extracted with chloroform. The organic layer was washed with saturated brine, and dried over anhydrous magnesium sulfate. Thereafter, the resultant was filtered and concentrated under reduced pressure. The obtained residue was purified by silica gel column chromatography (NH silica gel, chloroform/methanol=100/0 to 90/10), whereby Compound XI-3 (75.6 mg, yield: 43.33) was obtained.

ESI-MS m/z: 616 (M+H)$^+$; $^1$H-NMR (CDCl$_3$) δ: 0.89 (t, J=6.8 Hz, 6H), 1.26-1.38 (m, 32H), 1.46-1.54 (m, 4H), 3.73-1.82 (m, 2H), 2.05 (q, J=6.6 Hz, 8H), 2.76-2.80 (m, 6H), 3.18 (br s, 4H), 4.15 (t, J=6.2 Hz, 2H), 5.29-5.43 (m, 8H)

REFERENCE EXAMPLE 4

2-(1-Methylpyrrolidin-2-yl)ethyl 4-nitrophenyl carbonate hydrochloride (Compound VI-3)

To a solution of 4-nitrophenyl chloroformate (manufactured by Tokyo Chemical Industry Co., Ltd., 1.761 g, 8.56 mmol) in diethyl ether (20 mL), a solution of 2-(1-methylpyrrolidin-2-yl)ethanol (manufactured by Tokyo Chomical industry Co., Ltd., 1.0 mL, 7.13 mmol) in diethyl ether (20 mL) was added, followed by stirring overnight at room temperature. The reaction mixture was concentrated under reduced pressure, and the obtained residue was crystallized from ethanol/diethyl ether (1/1), followed by filtration, whereby Compound VI-3 (1.27 g, yield: 54%) was obtained.

$^1$H-NMR (DMSO-d$_6$) δ: 1.59-1.77 (m, 2H), 1.82-2.09 (m, 3H), 2.15-2.26 (m, 1H), 2.76 (s, 3H), 2.93-3.05 (m, 2H), 3.61-3.20 (m, 3H), 4.80 (br s, 1H), 6.95 (d, J=9.2 Hz, 2H), 8.11 (d, J=9.2 Hz, 2H)

REFERENCE EXAMPLE 5

4-Nitrophenyl 3-(piperidin-1-yl)propyl carbonate hydrochloride (Compound VI-4)

To a solution of 4-nitrophenyl chloroformate (1.58 g, 7.67 mmol) in diethyl ether (32 mL), 3-(piperidin-1-yl) propan-1-ol (manufactured by SIGMA-ALDRICH Co., Ltd., 1.00 mL, 6.39 mmol) was added, followed by stirring overnight at room temperature. The reaction mixture was concentrated under reduced pressure, and the obtained residue was crystallized from ethanol, followed by filtration, whereby Compound VI-4 (1.86 g, yield: 84%) was obtained.

ESI-MS m/z: 309 (M+H)$^+$; $^1$H-NMR (DMSO-d$_6$) δ: 1.28-1.49 (m, 1H), 1.62-1.89 (m, 5H), 2.10-2.26 (m, 9H), 2.76-2.96 (m, 2H), 3.04-3.19 (m, 2H), 3.36-3.49 (m, 2H), 4.33 (t, J=6.1 Hz, 2H), 7.58 (d, J=9.2 Hz, 2H), 8.33 (d, J=9.2 Hz, 2H), 10.37 (br s, 1H)

REFERENCE EXAMPLE 6

4-Nitrophenyl 3-(pyrrolidin-1-yl)propyl carbonate hydrochloride (Compound VI-5)

To a solution of 4-nitrophenyl chloroformate (596 mg, 2.84 mmol) in diethyl ether (10 mmol), a solution of 3-(pyrrolidin-1-yl)propan-1-ol (manufactured by ABCR, Inc., 386 mg, 2.84 mmol) in diethyl ether (10 mL) was added, followed by stirring at room temperature for 2 hours. The reaction mixture was concentrated under reduced pressure, and the obtained residue was crystallized from ethanol, followed by filtration, whereby Compound VI-5 (498 mg, yield: 53%) was obtained.

$^1$H-NMR (DMSO-d$_6$) δ: 1.76-1.84 (m, 2H), 1.85-2.00 (m, 4H), 3.11-3.16 (m, 2H), 3.30-3.44 (m, 4H), 3.47 (t, J=6.0 Hz, 2H), 4.77 (br s, 1H), 6.95 (d, J=9.2 Hz, 2H), 8.11 (d, J=9.2 Hz, 2H)

EXAMPLE 10

2-(1-Methylpyrrolidin-2-yl)ethyl di((9Z,12Z)-octadeca-9,12-dienyl)carbamate (Compound A-6)

Compound B-1 (0.161 g, 0.314 mmol) obtained in Example 1 was dissolved in acetonitrile (3.0 mL), and Compound VI-3 (0.156 g, 0.470 mmol) obtained in Reference Example 4 and triethylamine (0.219 mL, 1.57 mmol) were added thereto, followed by stirring at 80° C. for 2 hours. The reaction mixture was diluted with ethyl acetate, washed with water, and dried over anhydrous magnesium sulfate. Thereafter, the resultant was filtered and concentrated under reduced pressure. The obtained residue was purified by amino-silica gel column chromatography (n-hexane/ethyl acetate=80/20), whereby Compound A-6 (0.172 g, yield: 82%) was obtained.

ESI-MS m/z: 670 (M+H)$^+$; $^1$H-NMR (CDCl$_3$) δ: 0.89 (t, J=6.9 Hz, 6H), 1.20-1.40 (m, 32H), 1.45-1.57 (m, 6H), 1.62-1.83 (m, 2H), 1.94-2.18 (m, 12H), 2.31 (s, 3H), 2.77 (t, J=6.7 Hz, 4H), 3.03-3.26 (m, 5H), 4.06-4.17 (m, 2H), 5.29-5.42 (m, 8H)

EXAMPLE 11

3-(Piperidin-1-yl)propyl di((9Z,12Z)-octadeca-9,12-dienyl)carbamate (Compound A-7)

Compound A-7 (0.387 g, yield: 81%) was obtained in the same manner as in Example 5 by using Compound VI-4 obtained in Reference Example 5 in place of Compound VI-1.

ESI-MS m/z: 684 (M+H)$^+$; $^1$H-NMR (CDCl$_3$) δ: 0.89 (t, J=6.9 Hz, 6H), 1.21-1.62 (m, 42H), 1.79-1.86 (m, 2H), 2.02-2.08 (m, 8H), 2.32-2.42 (m, 6H), 2.77 (t, J=6.7 Hz, 4H), 3.10-3.43 (m, 4H), 4.09 (t, J=6.4 Hz, 2H), 5.29-5.42 (m, 8H)

EXAMPLE 12

3-(Pyrrolidin-1-yl)propyl di((9Z,12Z)-octadeca-9,12-dienyl)carbamate (Compound A-8)

Compound A-8 (0.225 g, yield: 99%) was obtained in the same manner as in Example 10 by using Compound VI-5 (0.168 g, 0.508 mmol) obtained in Reference Example 6 in place of Compound VI-3.

ESI-MS m/z: 670 (M+H)$^+$; $^1$H-NMR (CDCl$_3$) δ: 0.89 (t, J=6.9 Hz, 6H), 1.21-1.40 (m, 32H), 1.46-1.55 (m, 4H), 1.76-1.80 (m, 4H), 1.82-1.89 (m, 2H), 2.01-2.08 (m, 8H), 2.47-2.55 (m, 6H), 2.77 (t, J=6.7 Hz, 4H), 3.11-3.24 (m, 4H), 4.11 (t, J=6.4 Hz, 2H), 5.29-5.42 (in, 8H)

REFERENCE EXAMPLE 7

2-Nitro-N-((9Z,12Z)-octadeca-9,12-dienyl)benzenesulfonamide (Compound IId-1)

To a solution of (9Z,12Z)-octadeca-9,12-diethyl methanesulfonate (manufactured by Nu-Chek Prep, Inc., 2.85 g, 8.27 mmol) in acetonitrile (30 mL), cesium carbonate (6.74 g, 20.67 mmol), tetrabutylammonium iodide (manufactured by Tokyo Chemical Industry Co., Ltd., 3.05 g, 8.27 mmol), and N-(tert-butoxycarbonyl)-2-nitrobenzenesulfonamide (manufactured by Tokyo Chemical Industry Co., Ltd., 2.50 g, 8.27 mmol) were added, and the contents were allowed to react with each other under reflux by heating for 3 hours. The reaction mixture was cooled to room temperature, water was added thereto, and the mixture was extracted with ethyl acetate. The organic layer was dried over anhydrous magnesium sulfate. Thereafter, the resultant was filtered and concentrated under reduced pressure. The residue was purified by column chromatography (n-hexane/ethyl acetate=91/9 to 70/30), whereby tert-butyl(2-nitrophenyl) sulfonyl ((9Z,12Z)-octadeca-9,12-dien-1-yl)carbamate (3.21 g, yield: 70.5%) was obtained.

To a solution of tert-butyl(2-nitrophenyl)sulfonyl ((9Z, 12Z)-octadeca-9,12-dien-1-yl)carbamate (3.21 g, 5.83 mmol) in dichloromethane (22.5 mL), trifluoroacetic acid (9.63 mL, 126 mmol) was added, followed by stirring at room temperature for 0.5 hours. To the reaction mixture, dichloromethane and a sodium hydroxide aqueous solution (1 mol/L, 100 mL), and a saturated sodium hydrogencarbonate aqueous solution was further added thereto, thereby adjusting the aqueous layer at a pH of 8 or more. The obtained mixture was extracted with dichloromethane, washed with saturated brine, and dried over anhydrous magnesium sulfate. Thereafter, the resultant was filtered and concentrated under reduced pressure. The residue was purified by column chromatography (n-hexane/chloroform=50/50 to 0/100), whereby Compound IId-1 (2.48 g, yield: 94%) was obtained.

ESI-MS m/z: 451 (M+H)$^+$; $^1$H-NMR (CDCl$_3$) δ: 0.89 (t, J=7.0 Hz, 3H), 1.22-1.39 (m, 16H), 1.52 (m, 2H), 2.01-2.05 (m, 4H), 2.77 (t, J=6.6 Hz, 2H), 3.09 (q, J=6.7 Hz, 2H), 5.23 (m, 1H), 5.31-5.42 (m, 4H), 7.71-7.76 (m, 2H), 7.18-7.87 (1H), 8.13-8.15 (m, 1H)

EXAMPLE 13

Dodocyl((9Z,12Z)-octadeca-9,12-dien-1-yl)amine (Compound B-5)

To a solution of Compound IId-1 (0.714 g, 1.584 mmol) obtained in Reference Example 7 and 1-bromododecane (manufactured by Tokyo Chemical Industry Co., Ltd., 0.474 g, 1.90 mmol) in acetonitrile (6 mL), tetrabutylammonium iodide (manufactured by Tokyo Chemical Industry Co., Ltd., 0.585 g, 1.58 mmol) and cesium carbonate (1.03 g, 3.17 mmol) were added, followed by stirring at 60° C. for 1 hour. To the reaction mixture, water was added, and the mixture was extracted three times with n-hexane. The extract was purified by column chromatography (n-hexane/ethyl acetate=94/6 to 84/16), whereby N-dodecyl-2-nitro-N-((9Z, 12Z)-octadeca-9,12-dien-1-yl)benzenesulfonamide (0.750 g, yield: 76%) was obtained.

To a solution of N-dodecyl-2-nitro-N-((9Z,12Z)-octadeca-9,12-dien-1-yl)benzenesulfonamide (0.748 g, 1.21 mmol) in acetonitrile (7 mL), 1-dodecanethiol (manufactured by Tokyo Chemical Industry Co., Ltd., 0.611 g, 3.02 mmol) and 1,8-diazabicyclo[5.4.0]-7-undecene (manufactured by Nacalai Tesque, Inc., 0.460 g, 3.02 mmol) were added, followed by stirring at 60° C. for 1 hour. To the reaction mixture, water was added, and the mixture was extracted two times with ethyl acetate. The organic layers were combined, washed with saturated brine, and dried over anhydrous magnesium sulfate. Thereafter, the resultant was filtered and concentrated under reduced pressure. The residue was purified by column chromatography (n-hexane/ ethyl acetate=80/20 and then chloroform/methanol=100/0 to 88/12), whereby Compound B-5 (0.534 g, quantitative yield) was obtained.

ESI-MS m/z: 434 (M+H)$^+$; $^1$H-NMR (CDCl$_3$) δ: 0.88 (t, J=6.9 Hz, 3H), 0.89 (t, J=6.9 Hz, 3H), 1.24-1.38 (m, 35H), 1.49-1.54 (m, 4H), 2.05 (q, J=7.0 Hz, 4H), 2.62 (t, J=0.4 Hz, 4H), 2.77 (t, J=6.8 Hz, 2H), 5.30-5.41 (m, 4H)

EXAMPLE 14

Decyl((9Z,12Z)-octadeca-9,12-dien-1-yl)amine (Compound B-6)

Compound B-6 (0.423 g, yield: 76%) was obtained in the same manner as in Example 13 by using Compound IId-1 (0.619 q, 1.37 mmol) obtained in Reference Example 7 and 1-bromodecane (manufactured by Tokyo Chemical Industry Co., Ltd., 0.365 g, 1.65 mmol) in place of 1-bromododecane.

ESI-MS m/z: 406 (M+H)$^+$; $^1$H-NMR (CDCl$_3$) δ: 0.18 (t, J=7.1 Hz, 3H), 0.89 (t, J=6.9 Hz, 3H), 1.25-1.38 (m, 35H), 1.46-1.50 (m, 4H), 2.05 (q, J=7.0 Hz, 4H), 2.59 (t, J=7.2 Hz, 4H), 2.77 (t, J=6.9 Hz, 2H), 5.31-5.40 (m, 4H)

EXAMPLE 15

(9Z,12Z)-Octadeca-9,12-dien-1-yl) (octyl)amine (Compound B-7

Compound B-7 (0.519 g, yield: 87%) was obtained in the same manner as in Example 13 by using Compound IId-1 (0.714 g, 1.58 mmol) obtained in Reference Example 7 and 1-bromooctane (manufactured by Tokyo Chemical Industry Co., Ltd., 0.367 g, 1.90 mmol) in place of 1-bromododecane.

ESI-MS m/z: 378 (M+H)$^+$; $^1$H-NMR (CDCl$_3$) δ: 0.88 (t, J=7.1 Hz, 3H), 0.89 (t, J=6.9 Hz, 3H), 1.24-1.39 (m, 27H), 1.48-1.54 (m, 4H), 2.05 (q, J=7.0 Hz, 4H), 2.62 (t, J=7.4 Hz, 4H), 2.77 (t, J=6.6 Hz, 2H), 5.30-5.41 (m, 4H)

EXAMPLE 16

3-(Dimethylamino)propyl dodecyl((9Z,12Z)-octadeca-9,12-dienyl) carbamate (Compound A-9)

Compound A-9 (0.309 g, yield: 91%) was obtained in the same manner as in Example 5 by using Compound B-5 (0.260 g, 0.600 mmol) obtained in Example 13 in place of Compound B-1.

ESI-MS m/z: 563 (M+H)$^+$; $^1$H-NMR (CDCl$_3$) δ: 0.88 (t, J=6.9 Hz, 3H), 0.89 (t, J=6.9 Hz, 3H), 1.23-1.38 (m, 34H), 1.48-1.53 (m, 4H), 1.77-1.82 (m, 2H), 2.05 (q, J=7.1 Hz, 4H), 2.23 (s, 6H), 2.34 (t, J=7.6 Hz, 2H), 2.77 (t, J=6.6 Hz, 2H), 3.13-3.22 (m, 4H), 4.10 (t, J=6.5 Hz, 2H), 5.30-5.41 (m, 4H)

EXAMPLE 17

3-(Dimethylamino)propyl decyl((9Z,12Z)-octadeca-9,12-dienyl)carbamate (Compound A-10)

Compound A-10 (0.228 g, yield: 93%) was obtained in the same manner as in Example 5 by using Compound B-6 (0.185 g, 0.456 mmol) obtained in Example 14 in place of Compound B-1.

ESI-MS m/z: 535 (M+H)$^+$; $^1$H-NMR (CDCl$_3$) δ: 0.88 (t, J=6.8 Hz, 3H), 0.89 (t, J=6.7 Hz, 3H), 1.24-1.38 (m, 30H), 1.48-1.53 (m, 4H), 1.77-1.82 (m, 2H), 2.05 (q, J=7.0 Hz,

4H), 2.22 (s, 6H), 2.34 (t, J=7.5 Hz, 2H), 2.77 (t, J=6.8 Hz, 2H), 3.14-3.22 (m, 4H), 4.10 (t, J=6.4 Hz, 2H), 5.31-5.40 (n, 4H)

EXAMPLE 18

3-(Dimethylamino)propyl ((9Z,12Z)-octadeca-9,12-dienyl)(octyl)carbamate (Compound A-11)

Compound A-11 (0.275 g, yield: 90%) was obtained in the same manner as in Example 5 by using Compound B-7 (0.227 g, 0.600 mmol) obtained in Example 15 in place of Compound B-1.

ESI-MS m/z: 507 (M+H)$^+$; $^1$H-NMR (CDCl$_3$) δ: 0.88 (t, J=6.9 Hz, 3H), 0.89 (t, J=6.9 Hz, 3H), 1.22-1.39 (m, 26H), 1.47-1.54 (m, 4H), 1.76-1.82 (m, 2H), 2.05 (q, J=6.0 Hz, 4H), 2.23 (s, 6H), 2.34 (t, J=7.6 Hz, 2H), 2.77 (t, J=6.6 Hz, 2H), 3.12-3.22 (m, 4H), 4.10 (t, J=6.5 Hz, 2H), 5.30-5.41 (m, 4H)

REFERENCE EXAMPLE 8

2-((9Z,12Z-Octadeca-9,12-dietnyloxy)ethyl methanesulfonate (Compound IIIc-1)

To (9Z,12Z)-octadeca-9,12-dien-1-yl methanesulfonate (983 mg, 2.85 mmol), ethylene glycol (3.16 mL, 57.1 mmol) and 1,4-dioxane (5 mL) were added, and the mixture was stirred under reflux by heating for one day. The reaction mixture was cooled to room temperature, a sodium hydroxide aqueous solution (0.5 mol/L) was added thereto, and the mixture was extracted two times with ethyl acetate. The organic layers were combined and washed with saturated brine, followed by drying over anhydrous magnesium sulfate. Thereafter, the resultant was filtered and concentrated under reduced pressure. The residue was purified by column chromatography (100, chloroform), whereby 2-((9Z,12Z)-octadeca-9,12-dienyloxy)ethanol (668 mg, yield: 75%) was obtained.

To a solution of 2-((9Z,12Z)-octadeca-9,12-dienyloxy)ethanol (660 mg, 2.13 mmol) and triethylamine (0.444 mL, 3.19 mmol) in dichloromethane (9 mL), mesylic anhydride (manufactured by SIGMA-ALDRICH Co., Ltd., 0.247 mL, 3.19 mmol) was added at 0° C., followed by stirring at room temperature for 40 minutes. To the reaction mixture, water was added, and the mixture was extracted with chloroform. The organic layer was washed with hydrochloric acid (1 mol/L), a saturated sodium hydrogencarbonate aqueous solution, and saturated brine and dried over anhydrous magnesium sulfated. Thereafter, the resultant was filtered and concentrated under reduced pressure, whereby Compound IIIc-1 was obtained.

EXAMPLE 19

(9Z,12Z)-N-(2-((9Z,12Z)-Octadeca-9,12-dienyloxy)ethyl)octa deca-9,12-dien-1-amine (Compound B-8)

Compound B-8 (0.676 g, yield: 68%) was obtained in the same mannet as in Example 13 by using Compound IId-1 (0.798 g, 1.77 mmol) obtained in Reference Example 7 and Compound IIIc-1 (0.826 g, 2.13 mmol) obtained in Reference Example 8 in place of 1-bromododecane.

ESI-MS m/z: 558 (M+H)$^+$; $^1$H-NMR (CDCl$_3$) δ: 0.89 (t, J=6.9 Hz, 6H), 1.27-1.38 (m, 32H), 1.46-1.52 (m, 2H), 1.54-1.60 (m, 3H), 2.05 (q, J=7.0 Hz, 8H), 2.61 (t, J=7.3 Hz, 2H), 2.77 (t, J=5.5 Hz, 6H), 3.42 (t, J=6.8 Hz, 2H), 3.52 (t, J=5.4 Hz, 2H), 5.30-5.41 (m, 8H).

EXAMPLE 20

3-(Dimethylamino)propyl ((9Z,12Z)-octadeca-9,12-dienyl)(2-((9Z,12Z)-octadeca-9,12-dienyloxy)ethyl)carbamate (Compound A-12)

Compound A-12 (0.208 g, yield: 92%) was obtained in the same manner as in Example 5 by using Compound B-8 (0.184 g, 0.330 mmol) obtained in Example 19 in place of Compound B-1.

ESI-MS m/z: 637 (M+H)$^+$; $^1$H-NMR (CDCl$_3$) δ: 0.89 (t, J=6.9 Hz, 6H), 1.25-1.38 (m, 32H), 1.50-1.57 (m, 4H), 1.77-1.83 (m, 2H), 2.05 (q, J=7.0 Hz, 8H), 2.22 (s, 6H), 2.34 (t, J=7.4 Hz, 2H), 2.77 (t, J=6.6 Hz, 4H), 3.23-3.54 (m, H11), 4.11 (t, J=6.5 Hz, 2H), 5.30-5.41 (m, 8H)

REFERENCE EXAMPLE 9

N, N-Bis(2-((9Z,12Z)-octadeca-9,12-dienyloxy)ethyl)amine (Compound XI-4)

To sodium hydride (oily, 60%, 1.69 g, 42.2 mmol), a solution of N-benzyldiethanolamine (manufactured by Tokyo Chemical Industry Co., Ltd., 1.65 g, 8.44 mmol) in toluene (10 mL) was slowly added while stirring, and thereafter, a solution of (9Z,12Z)-octadeca-9,12-dienyl methanesulfonate (manufactured by Nu-Chek Prep, Inc., 6.69 g, 19.4 mmol) in toluene (10 mL) was added dropwise thereto. The obtained mixture was stirred under reflux by heating for 4 hours. After cooling to room temperature, the reaction was stopped with ethanol. To the obtained mixture, saturated brine was added, and the mixture was extracted two times with ethyl acetate. The organic layers were combined and dried over anhydrous magnesium sulfate. Thereafter, the resultant was concentrated under reduced pressure. The residue was purified by silica gel column chromatography (chloroform/methanol=100/0 to 99/1), whereby N-benzyl-N,N-bis(2-((9Z,12Z)-octadeca-9,12-dienyloxy)ethyl)amine (4.01 g, yield: 69%) was obtained.

N-Benzyl-N,N-bis(2-((9Z,12Z)-octadeca-9,12-dienyloxy)ethyl)amine (4.01 g, 5.89 mmol) was dissolved in 1,2-dichloroethane (29 mL), and 1-chloroethyl chloroformate (manufactured by Tokyo Chemical Industry Co., Ltd., 1.90 mL, 17.4 mmol) was added thereto, followed by stirring at 130° C. for 1 hour. To the reaction solution, methanol (29 mL) was added, and the mixture was further stirred at 130° C. for 1 hour. After cooling to room temperature, a saturated sodium hydrogencarbonate aqueous solution was added to the reaction mixture, and the mixture was extracted two times with chloroform. The organic layers were combined, washed with saturated brine, and dried over anhydrous magnesium sulfate. Thereafter, the resultant was concentrated under reduced pressure. The residue was purified by amino-silica gel column chromatography (n-hexane/ethyl acetate=90/10 to 75/25), whereby Compound XI-4 (5.56 g, yield: 92%) was obtained.

ESI-MS m/z: 621 (M+H)$^+$; $^1$H-NMR (CDCl$_4$) δ: 0.89 (t, J=7.0 Hz, 6H), 1.27-1.30 (m, 33H), 1.53-1.59 (m, 4H), 2.05 (q, J=7.1 Hz, 8H), 2.77 (t, J=6.8 Hz, 4H), 2.80 (t, J=5.4 Hz, 4H), 3.42 (t, J=6.8 Hz, 4H), 3.53 (t, J=5.4 Hz, 4H), 5.30-5.41 (m, 8H)

REFERENCE EXAMPLE 10

3-(Dimethylamino)propyl bis(2-((9Z,12Z)-octadeca-9,12-dienyloxy)ethyl)carbamate (Compound XI-5)

Compound XI-5 (1.32 g, yield: 91%) was obtained in the same manner as in Example 5 by using Compound XI-4 (1.20 g, 1.99 mmol) obtained in Reference Example 9 in place of Compound B-1.

ESI-MS m/n: 732 (M+H)$^+$; $^1$H-NMR (CDCl$_3$) δ: 0.89 (t, J=7.0 Hz, 6H), 1.27-1.30 (m, 30H), 1.51-1.57 (m, 4H), 1.77-1.83 (m, 4H), 2.05 (q, J=7.0 Hz, 8H), 2.23 (s, 6H), 2.34 (t, J=7.5 Hz, 2H), 2.77 (t, J=6.7 Hz, 4H), 3.38-3.54 (m, 12H), 4.12 (t, J=6.5 Hz, 2H), 5.30-5.41 (m, 8H)

REFERENCE EXAMPLE 11

Ethyl 3-(di((9Z,12Z)-octadeca-9,12-dienyl)amino) propionate (Compound XI-6)

Compound B-1 (0.788 g 1.53 mmol) obtained in Example 1 was dissolved in ethanol (8 mL), and ethyl acrylate (manufactured by Tokyo Chemical Industry Co., Ltd., 1.67 mL, 15.3 mmol) and sodium ethoxide (manufactured by Wako Pure Chemical Industries, Ltd., 0.0520 g, 0.767 mmol) were added thereto, followed by stirring under reflux by heating for 3 hours. The reaction mixture was concentrated under reduced pressure, and thereafter, the obtained residue was purified by silica gel column chromatography (n-hexane/ethyl acetate=85/15), whereby Compound XI-6 (0.699 g, yield: 74%) was obtained.

ESI-MS m/z: 625 (M+H)$^+$; $^1$H-NMR (CDCl$_3$) δ: 0.89 (t, J=6.9 Hz, 6H), 1.21-1.45 (m, 39H), 2.02-2.08 (m, 8H), 2.35-2.44 (m, 6H), 2.75-2.80 (m, 6H), 4.12 (q, J=7.0 Hz, 2H), 5.30-5.42 (m, 8H)

EXAMPLE 21

3-(Di((9Z,12Z)-octadeca-9,12-dienyl)amino)propan-1-ol (Compound C-1)

Compound XI-6 (0.199 g, 0.324 mmol) obtained in Reference Example 11 was dissolved in tetrahydrofuran (2 mL), and lithium aluminum hydride (manufactured by Junsei Chemical Co., Ltd., 0.012 g, 0.324 mmol) was added thereto under ice cooling, followed by stirring for 3 hours. To the reaction mixture, water (0.0600 mL, 3.33 mmol) and sodium fluoride (manufactured by Nacalai Tesque, Inc., 0.408 q, 9.72 mmol) were added, followed by stirring at room temperature for 0.5 hours. An insoluble matter was removed by filtration with a celite. The filtrate was concentrated and thereafter purified by silica gel column chromatography (chloroform/methanol=98/2), whereby Compound C-1 (0.181 g, yield: 98%) was obtained.

ESI-MS m/z: 573 (M+H)$^+$; $^1$H-NMR (CDCl$_3$) δ: 0.89 (t, J=6.9 Hz, 6H), 1.21-1.40 (m, 32H), 1.42-1.51 (m, 4H), 1.64-1.71 (m, 2H), 2.02-2.08 (m, 8H), 2.40 (t, J=7.3 Hz, 1H), 2.64 (t, J=5.3 Hz, 2H), 2.17 (t, J=6.7 Hz, 4H), 3.79 (t, J=5.3 Hz, 2H), 5.30-5.42 (m, 8H)

REFERENCE EXAMPLE 12

3-(Di((9Z,12Z)-octadeca-9,12-dienyl)amino)propane-1,2-diol (Compound XI-7)

Compound B-1 (0.228 g, 0.444 mmol) obtained in Example 1 was dissolved in dichloroethane (2 mL), and methanol (2 mL) and 2,3-dihydroxypropanal (manufactured by Nacalai Tesque, Inc., 0.400 g, 4.44 mmol) were added thereto, followed by stirring at room temperature for 0.5 hours. To the reaction mixture, sodium triacetoxyborohydride (manufactured by Tokyo Chemical Industry Co., Ltd., 0.470 g, 2.22 mmol) was added, followed by stirring overnight at room temperature. To the reaction mixture, 2,3-dihydroxypropanal (0.400 g, 4.44 mmol) was added, followed by stirring at room temperature for 3 hours. To the reaction mixture, sodium triacetoxyborohydride (0.470 g, 2.22 mmol) was added, followed by stirring overnight at room temperature. To the reaction mixture, a saturated sodium hydrogencarbonate aqueous solution was added, and the mixture was extracted two times with chloroform. The organic layers were combined, washed with saturated brine, and dried over anhydrous magnesium sulfate. Thereafter, the resultant was filtered and concentrated under reduced pressure. The obtained residue was purified by amino-silica gel column chromatography (n-hexane/ethyl acetate=50/50), whereby Compound XI-7 (0.0449 g, yield: 1.7%) was obtained.

ESI-MS m/z: 589 (M+H)+; $^1$H-NMR (CDCl$_3$) δ: 0.89 (t, J=6.9 Hz, 6H), 1.19-1.51 (m, 36H), 2.02-2.08 (m, 8H), 2.38-2.62 (m, 6H), 2.77 (t, J=6.7 Hz, 4H), 3.46-3.50 (m, 1H), 3.69-3.77 (m, 2H), 5.30-5.42 (m, 8H)

REFERENCE EXAMPLE 13

3-((3R,4R)-3,4-Bis((9Z,12Z)-octadeca-9,12-dienyloxy)pyrrolidin-1-yl)propan-1-ol (Compound XI-8)

Compound XI-8 was synthesized by the method described in WO2011/136368.

EXAMPLE 22

4-(Dimethylamino)butyl di((9Z,12Z)-octadeca-9,12-dienyl)carbamate (Compound A-13)

Step 1:

To a solution of 4-nitrophenyl chloroformate (0.867 g, 4.21 mmol) in dichloromethane (20 mL), 4-(tert-butyldimethylsilyl)oxy-1-butanol (manufactured by SIGMA-ALDRICH Co., Ltd., 1.0 mL, 4.21 mmol) and triethylamine (0.881 mL, 6.32 mmol) were added, followed by stirring at room temperature for 1 hour. To the reaction mixture, a saturated sodium hydrogencarbonate aqueous solution was added, and the mixture was extracted two times with chloroform. The organic layer was dried over anhydrous magnesium sulfate and thereafter filtered. The resultant was concentrated under reduced pressure. The obtained residue was purified by silica gel column chromatography (n-hexane/ethyl acetate=90/10), whereby 4-(tert-butyldimethylsilyloxy)butyl 4-nitrophenyl carbonate (1.44 g, yield: 92%) was obtained.

Step 2:

A crude purified product of 4-(tert-butyldimethylsilyloxy) butyl di((9Z,12Z)-octadeca-9,2-dienyl)carbamate was obtained in the same manner as in Example 10 by using 4-(tert-butyldimethylsilyloxy)butyl 4-nitrophenyl carbonate (0.640 g, 1.733 mmol) obtained in Step 1 in place of Compound VI-3. The obtained crude purified product of 4-(tert-butyldimethylsilyloxy)butyl di((9Z,12Z)-octadeca-9,12-dienyl)carbamate was dissolved in tetrahydrofuran (10 mL), and tetrabutylammonium fluoride (manufactured by Tokyo Chemical Industry Co., Ltd., about 1 mol/L tetrahydrofuran solution, 2.14 mL, 2.14 mmol) was added thereto, followed by stirring at room temperature for 1 hour. To the reaction mixture, tetra-n-butylammonium fluoride (about 1 mol/L tetrahydrofuran solution, 2.14 mL, 2.14 mmol) was added, followed by stirring at room temperature for 2 hours and thereafter stirring at 50° C. for 1 hour. To the reaction mixture, a saturated sodium hydrogencarbonate aqueous solution was added, and the mixture was extracted two times with ethyl acetate. The organic layer was dried over anhydrous magnesium sulfate and thereafter filtered. The resultant was concentrated under reduced pressure. The obtained residue was purified by silica gel column chromatography (chloroform/methanol=95/5), whereby 4-hydroxybutyl di(9Z,12Z)-octadeca-9,12-dienyl)carbamate (0.652 g, yield: 73%) was obtained.
Step 3:
To a solution of 4-hydroxybutyl di((9Z,12Z)-octadeca-9,12-dienyl)carbamate (0.193 g, 0.306 mmol) obtained in Step 2 in dichloromethane (2 mL), mesylic acid chloride (manufactured by Junsei Chemical Co., Ltd., 0.0360 mL, 0.460 mmol) and triethylamine (0.0930 mL, 0.919 mmol) were added under ice cooling, followed by stirring at 0° C. for 30 minutes. To the reaction mixture, a saturated sodium hydrogencarbonate aqueous solution was added, and the mixture was extracted two times with chloroform. The organic layer was dried over anhydrous magnesium sulfate and thereafter filtered. The resultant was concentrated under reduced pressure. The obtained residue was dissolved in tetrahydrofuran (1 mL), and dimethylamine (manufactured by SIGMA-ALDRICH Co., Ltd., about 2 mol/L tetrahydrofuran solution, 1.53 mL, 3.06 mmol) was added, followed by stirring at 100° C. for 1 hour using a micro wave reactor and thereafter stirring at 130° C. for 1 hour using a micro wave reactor. The reaction mixture was concentrated under reduced pressure, and the obtained residue was purified by amino-silica gel column chromatography (n-hexane/ethyl acetate=80/20), whereby Compound A-13 (0.159 g, yield: 79%) was obtained.
ESI-MS m/z: 658 (M+H)$^+$; $^1$H-NMR (CDCl$_3$) δ: 0.90 (q, 0=6.5 Hz, 6H), 1.20-1.38 (m, 32H), 1.45-1.56 (m, 6H), 1.61-1.69 (m, 2H), 2.01-2.08 (m, 8H), 2.21 (s, 6H), 2.28 (t, J=7.6 Hz, 2H), 2.77 (t, J=6.6 Hz, 4H), 3.12-3.23 (m, 4H), 4.07 (t, J=6.6 Hz, 2H), 5.29-5.42 (m, 81H)

REFERENCE EXAMPLE 14

(1-Methylpiperidin-4-yl)methyl 4-nitrophenyl carbonate hydrochloride (Compound VI-6)

To a solution of 4-nitrophenyl chloroformate (1.50 g, 7.28 mmol) in tetrahydrofuran (3 mL), 1-methyl-4-piperidinemethanol (manufactured by Tokyo Chemical Industry Co., Ltd., 1.0 mL, 7.28 mmol) was added, followed by stirring at room temperature for 2 hours. A deposited crystal was collected by filtration, whereby Compound VI-6 (1.55 g, yield: 64%) was obtained.
ESI-MS m/z: 295 (M+H)$^+$; $^1$H-NMR (CDCl$_3$) δ: 1.93-2.19 (m, 4H), 2.68-2.82 (m, 3H), 3.51-3.62 (m, 5H), 4.21 (d, J=6.0 Hz, 2H), 7.38 (d, J=9.1 Hz, 2H), 8.27 (d, J=9.1 Hz, 2H), 12.44 (br s, 1H)

REFERENCE EXAMPLE 15

(1-Methylpiperidin-3-yl)methyl 4-nitrophenyl carbonate hydrochloride (Compound VI-7)

Compound VI-7 (2.32 g, yield: 97%) was obtained in the same manner as in Reference Example 14 by using 1-methyl-3-piperidinemethanol (manufactured by Tokyo Chemical Industry Co., Ltd., 1.0 mL, 7.21 mmol) in place of 1-methyl-4-piperidinemethanol.
ESI-MS m/z: 295 (M+H)$^+$

REFERENCE EXAMPLE 16

(1-Methylpiperidin-2-yl)methyl 4-nitrophenyl carbonate hydrochloride (Compound VI-8)

Compound VI-8 (2.37 g, yield: 96%) was obtained in the same manner as in Reference Example 14 by using 1-methyl-2-piperidinemethanol (manufactured by Tokyo Chemical Industry Co., Ltd., 1.0 mL, 7.43 mmol) in place of 1-methyl-4-piperidinemethanol.
$^1$H-NMR (CDCl$_3$) δ: 1.51-1.63 (m, 1H), 1.81-2.38 (m, 5H), 2.85-2.99 (m, 4H), 3.21-3.30 (m, 1H), 3.49-3.60 (m, 1H), 4.66 (dd, J=13.1, 2.4 Hz, 1H), 4.78-4.86 (m, 1H), 7.47 (d, J=9.1 Hz, 2H), 8.28 (d, J=9.1 Hz, 2H), 12.40 (br s, 1H)

REFERENCE EXAMPLE 17

3-(Azepan-1-yl)propyl 4-nitrophenyl carbonate hydrochloride (Compound VI-9)

Compound VI-9 (1.47 g, yield: 92%) was obtained in the same manner as in Reference Example 14 by using 3-(azepan-1-yl)propanol (manufactured by ChemBridge Corporation, 0.700 g, 4.45 mmol) in place of 1-methyl-4-piperidinemethanol.
ESI-MS m/z: 323 (M+H)$^+$; $^1$H-NMR (CDCl$_3$) δ: 1.60-1.75 (m, 2H), 1.79-1.94 (m, 5H), 2.15-2.27 (m, 2H), 2.44-2.53 (m, 2H), 2.90-3.02 (m, 2H), 3.14-3.24 (m, 2H), 3.55-3.65 (m, 2H), 4.41 (t, J=5.9 Hz, 2H), 7.37-7.43 (m, 2H), 0.25-8.32 (m, 2H), 12.48 (br s, 1H)

REFERENCE EXAMPLE 18

1-Methylpiperidin-4-yl 4-nitrophenyl carbonate hydrochloride (Compound VI-10)

Compound VI-10 (0.740 g, yield: 90%) was obtained in the same manner as in Reference Example 14 by using 1-methylpiperidin-4-ol (manufactured by SIGMA-ALDRICH Co., Ltd., 0.300 g, 2.60 mmol) in place of 1-methyl-4-piperidinemethanol.
ESI-MS m/z: 281 (M+H)$^+$

REFERENCE EXAMPLE 19

1-Methylpiperidin-3-yl 4-nitrophenyl carbonate hydrochloride (Compound VI-11)

Compound VI-11 (0.410 g, yield: 49%) was obtained in the same manner as in Reference Example 14 by using 1-methylpiperidin-3-ol (manufactured by SIGMA-ALDRICH Co., Ltd., 0.305 g, 2.65 mmol) in place of 1-methyl-4-piperidinemethanol.
ESI-MS m/z: 281 (M+H)$^+$

REFERENCE EXAMPLE 20

(1-Methylpyrrolidin-3-yl)methyl 4-nitrophenyl carbonate hydrochloride (Compound VI-12)

Compound VI-12 (0.943 g, yield: 69%) was obtained in the same manner as in Reference Example 14 by using (1-methyl-3-pyrrolidiny)methanol (manufactured by Matrix Scientific, 0.500 g, 7.43 mmol) in place of 1-methyl-4-piperidinemethanol.

ESI-MS m/z: 281 (M+H)$^+$

EXAMPLE 23

(1-Methylpiperidin-4-yl)methyl di((9Z,12Z)-octadeca-9,12-dien-1-yl)carbamate (Compound A-14)

Compound A-14 (0.258 g, yield: 84%) was obtained in the same manner as in Example 10 by using Compound VI-6 (0.228 g, 0.689 mmol) obtained in Reference Example 14 in place of Compound VI-3.

ESI-MS m/z: 670 (M+H)$^+$; $^1$H-NMR (CDCl$_3$) δ: 0.89 (t, J=6.9 Hz, 6H), 1.22-1.39 (m, 32H), 1.46-1.54 (m, 4H), 1.56-1.66 (m, 3H), 1.67-1.74 (m, 2H), 1.88-1.95 (m, 2H), 2.05 (q, J=6.9 Hz, 8H), 2.26 (s, 3H), 2.77 (t, J=6.8 Hz, 4H), 2.85 (d, J=11.7 Hz, 2H), 3.13-3.23 (m, 4H), 3.92 (d, J=6.3 Hz, 2H), 5.30-5.42 (m, 8H)

EXAMPLE 24

(1-Methylpiperidin-3-yl)methyl di(9Z,12Z)-octadeca-9,12-dien-1-yl)carbamate (Compound A-15)

Compound A-15 (0.239 g, yield: 74%) was obtained in the same manner as in Example 10 by using Compound VI-7 (0.238 g, 0.719 mmol) obtained in Reference Example 15 in place of Compound VI-3.

ESI-MS m/z: 670 (M+H)r; $^1$H-NMR (CDCl$_3$) δ: 0.89 (t, J=6.9 Hz, 6H), 0.92-1.02 (m, 1H), 1.22-1.39 (m, 32H), 1.46-1.54 (m, 4H), 1.55-1.65 (m, 1H), 1.66-1.74 (m, 3H), 1.82-1.89 (m, 1H), 1.91-2.00 (m, 1H), 2.05 (q, J=7.0 Hz, 8H), 2.26 (s, 3H), 2.74-2.80 (m, 5H), 2.84-2.89 (m, 1H), 3.12-3.23 (m, 4H), 3.87 (dd, J=10.7, 7.6 Hz, 1H), 3.97 (dd, J=10.7, 5.4 Hz, 1H), 5.30-5.41 (m, 8H)

EXAMPLE 25

(1-Methylpiperidin-2-yl)methyl di((9Z,12Z)-octadeca-9,12-dien-1-yl)carbamate (Compound A-16)

Compound A-16 (0.313 g, yield: 91%) was obtained in the same manner as in Example 10 by using Compound VI-8 (0.256 g, 0.774 mmol) obtained in Reference Example 16 in place of Compound VI-3.

ESI-MS m/z: 670 (M+H)$^+$; $^1$H-NMR (CDCl$_3$) δ: 0.89 (t, J=6.9 Hz, 6H), 1.22-1.39 (m, 32H), 1.46-1.64 (m, 8H), 1.71-1.76 (m, 2H), 2.02-2.12 (m, 10H), 2.32 (s, 3H), 2.77 (t, J=6.8 Hz, 4H), 2.79-2.84 (m, 1H), 3.11-3.24 (m, 4H), 4.05 (dd, J=11.1, 4.9 Hz, 1H), 4.17 (dd, J=11.1, 4.9 Hz, 1H), 5.30-5.42 (m, 8H)

EXAMPLE 26

2-(1-Methylpyrrolidin-2-yl)ethyl di((Z)-octadec-9-enyl)carbamate (Compound A-17)

Compound A-17 (0.360 g, yield: 92%) was obtained in the same manner as in Example 10 by using Compound B-2 (0.300 g, 0.579 mmol) obtained in Example 2 in place of Compound B-1.

ESI-MS m/z: 674 (M+H)+; $^1$H-NMR (CDCl$_3$) δ: 0.88 (t, J=6.9 Hz, 6H), 1.21-1.38 (m, 44H), 1.45-1.85 (m, 8H), 1.93-2.18 (m, 12H), 2.32 (s, 3H), 3.03-3.26 (m, 5H), 4.05-1.18 (m, 2H), 5.30-5.39 (m, 4H)

EXAMPLE 27

(1-Methylpiperidin-3-yl)methyl di((Z)-octadec-9-enyl)carbamate (Compound A-18)

Compound A-18 (0.390 g, yield: 100%) was obtained in the same manner as in Example 10 by using Compound B-2 (0.300 g, 0.579 mmol) obtained in Example 2 in place of Compound B-1 and Compound VI-7 (0.287 g, 0.896 mmol) obtained in Reference Example 15 in place of Compound VI-3.

ESI-MS m/z: 674 (M+H)$^+$; $^1$H-NMR (CDCl$_3$) δ: 0.85-1.04 (m, 7H), 1.20-1.38 (m, 44H), 1.46-1.74 (m, 8H), 1.82-2.06 (m, 10H), 2.26 (s, 3H), 2.74-2.82 (m, 1H), 2.83-2.89 (m, 1H), 3.1.0-3.25 (m, 4H), 3.87 (dd, J=10.5, 7.3 Hz, 1H), 3.98 (dd, J=10.5, 5.3 Hz, 1H), 5.30-5.39 (m, 4H)

EXAMPLE 28

2-(1-Methylpyrrolidin-2-yl)ethyl di((11Z,14Z)-icosa-11,14-dienyl)carbamate (Compound A-19)

Compound A-19 (0.369 g, yield: 97%) was obtained in the same manner as in Example 10 by using Compound B-4 (0.300 g, 0.526 mmol) obtained in Example 4 in place of Compound B-1.

ESI-MS m/z: 726 (M+H)$^+$; $^1$H-NMR (CDCl$_3$) δ: 0.89 (t, J=6.9 Hz, 6H), 1.21-1.40 (m, 40H), 1.44-1.85 (m, 8H), 1.93-2.18 (m, 12H), 2.32 (s, 3H), 2.77 (t, J=6.4 Hz, 4H), 3.04-3.27 (m, 5H), 4.05-4.18 (m, 2H), 5.29-5.42 (m, 8H)

EXAMPLE 29

(1-Methylpiperidin-3-yl)methyl di((11Z,14Z)-icosa-11,14-dienyl)carbamate (Compound A-20)

Compound A-20 (0.374 g, yield: 98%) was obtained in the same manner as in Example 10 by using Compound B-4 (0.300 g, 0.526 mmol) obtained in Example 4 in place of Compound B-1 and Compound VI-7 (0.261 g, 0.789 mmol) obtained in Reference Example 15 in place of Compound VI-3.

ESI-MS m/z: 726 (M+H)$^+$; $^1$H-NMR (CDCl$_3$) δ: 0.85-1.04 (m, 7H), 1.21-1.40 (m, 40H), 1.45-1.75 (m, 8H), 1.82-2.09 (m, 10H), 2.26 (s, 3H), 2.74-2.90 (m, 6H), 3.11-3.24 (m, 4H), 3.87 (dd, J=10.5, 7.5 Hz, 1H), 3.98 (dd, J=10.5, 5.5 Hz, 1H), 5.29-5.43 (m, 8H)

EXAMPLE 30

(1-Methylpyrrolidin-2-yl)methyl di((9Z,12Z)-octadeca-9,12-dien-1-yl)carbamate (Compound A-21)

Compound B-1 (0.0831 g, 0.162 mmol) obtained in Example 1 was dissolved in dichloroethane (1 mL), and 1,1'-carbonyl diimidazole manufactured by Nacalai Tesque, Inc., 0.0394 g, 0.243 mmol) were added thereto, followed by stirring overnight at room temperature. To the reaction mixture, iodomethane (manufactured by Tokyo Chemical Industry Co., Ltd., 0.101 mL, 1.62 mmol) was added, followed by stirring overnight at 60° C. The reaction mixture was concentrated under reduced pressure. The obtained residue was dissolved in tetrahydrofuran (1 mL), and 1-methylpyrrolidine-2-methanol (manufactured by Wako Pure Chemical Industries, Ltd., 0.0372 g, 0.323 mmol) and triethylamine (0.0563 mL, 0.404 mmol) were added thereto, followed by stirring overnight at room temperature. Thereafter, the reaction mixture was stirred at 60° C. for 3 hours. To the reaction mixture, a saturated sodium hydrogencarbonate aqueous solution was added, and the mixture was extracted two times with n-hexane. The organic layer was dried over anhydrous magnesium sulfate and thereafter filtered. The resultant was concentrated under reduced pressure. The obtained residue was purified by amino-silica gel column chromatography (n-hexane/ethyl acetate=90/10), whereby Compound A-21 (0.0318 g, yield: 30%) was obtained.

ESI-MS m/z: 656 (M+H)$^+$; $^1$H-NMR (CDCl$_3$) δ: 0.89 (t, J=6.9 Hz, 6H), 1.24-1.39 (m, 32H), 1.46-1.67 (m, 5H), 1.67-1.85 (m, 2H), 1.89-2.00 (m, 1H), 2.05 (q, J=7.0 Hz, 8H), 2.21-2.30 (m, 1H), 2.42 (s, 3H), 2.43-2.51 (m, 1H), 2.77 (t, J=6.6 Hz, 4H), 3.03-3.08 (m, 1H), 3.11-3.25 (m, 4H), 4.00 (dd, J=10.5, 6.0 Hz, 1H), 4.08 (dd, J=10.5, 5.5 Hz, 1H), 5.29-5.42 (m, 8H)

EXAMPLE 31

(1-Methylpyrrolidin-3-yl)methyl di(9Z,12Z)-octadeca-9,12-dienyl)carbamate (Compound A-22)

Compound A-22 (0.263 g, yield: 66%) was obtained in the same manner as in Example 10 by using Compound VI-12 (0.277 g, 0.876 mmol) obtained in Reference Example 20 in place of Compound VI-3.

ESI-MS m/z: 656 (M+H)$^+$; $^1$H-NMR (CDCl$_3$) δ: 0.89 (t, J=6.9 Hz, 6H), 1.20-1.40 (m, 32H), 1.44-1.78 (m, 5H), 1.92-2.09 (m, 9H), 2.24 (dd, J=9.4, 6.2 Hz, 1H), 2.34 (s, 3H), 2.39-2.63 (m, 3H), 2.68-2.80 (m, 5H), 3.10-3.25 (m, 4H), 3.95 (dd, J=10.5, 7.8 Hz, 1H), 4.03 (dd, J=10.5, 6.4 Hz, 1H), 5.28-5.42 (m, 8H)

EXAMPLE 32

2-(1-Methylpiperidin-2-yl)ethyl di(9Z,12Z)-octadeca-9,12-diethylcarbamate (Compound A-23)

Step 1:
To a solution of 4-introphenyl chloroformate (0.844 g, 7.19 mmol) in tetrahydrofuran (12 mL), 2-(1-methylpiperidin-2-yl) ethanol (manufactured by Matrix Scientific, 0.500 g, 3.49 mmol) was added, followed by stirring overnight at room temperature. The reaction mixture was concentrated under reduced pressure, whereby a crude purified product of 2-(1-methylpiperidin-2-yl) ethyl 4-nitrophenyl carbonate hydrochloride was obtained.
Step 2:
Compound A-23 (0.299 g, yield: 75%) was obtained in the same manner as in Example 10 by using the crude purified product of 2-(1-methylpiperidin-2-yl) ethyl 4-nitrophenyl carbonate hydrochloride (0.302 g, 0.876 mmol) obtained in Step 1 in place of Compound VI-3.

ESI-MS m/z: 684 (M+H)$^+$; $^1$H-NMR (CDCl$_3$) δ: 0.89 (t, J=6.9 Hz, 6H), 1.19-1.40 (m, 32H), 1.45-1.75 (m, 11H), 1.93-2.11 (m, 11H), 2.21 (s, 3H), 2.74-2.86 (m, 51H), 3.10-3.24 (m, 4H), 4.06-4.19 (m, 2H), 5.29-5.42 (m, 8H)

EXAMPLE 33

3-(Azepan-1-yl)propyl di((9Z,12Z)-octadeca-9,12-dien-1-yl)carbamate (Compound A-24)

Compound A-24 (0.136 g, yield: 67%) was obtained in the same manner as in Example 10 by using Compound VI-9 obtained in Reference Example 17 in place of Compound VI-3.

ESI-MS m/z: 698 (M+H)$^+$; $^1$H-NMR (CDCl$_3$) δ: 0.86-0.94 (m, 6H), 1.22-1.41 (m, 36H), 1.45-1.67 (m, 8H), 1.75-1.85 (m, 2H), 2.00-2.11 (m, 8H), 2.55 (t, J=7.5 Hz, 21H), 2.62 (t, J=5.1 Hz, 4H), 2.77 (t, J=5.9 Hz, 4H), 3.13-3.23 (m, 4H), 4.10 (t, J=6.4 Hz, 2H), 5.28-5.45 (m, 8H)

EXAMPLE 34

3-(Piperidin-1-yl)propyl ((9Z,12Z)-octadeca-9,12-dienyl)(2-((9Z,12Z)-octadeca-9,12-dienyloxy)ethyl) carbamate (Compound A-29)

Compound A-29 (0.170 g, yield: 87%) was obtained in the same manner as in Example 10 by using Compound B-8 (0.150 g, 0.269 mmol) obtained in Example 19 in place of Compound B-1 and Compound VI-4 (0.201 g, 0.672 mmol) obtained in Reference Example 5 in place of Compound VI-3.

ESI-MS m/z: 728 (M+H)$^+$; $^1$H-NMR (CDCl$_3$) δ: 0.09 (t, J=6.8 Hz, 6H), 1.22-1.40 (m, 32H), 1.40-1.63 (m, 14H), 1.78-1.87 (m, 2H), 2.05 (q, J=6.6 Hz, 8H), 2.33-2.41 (m, 6H), 2.77 (t, J=6.0 Hz, 4H), 3.20-3.31 (m, 2H), 3.40 (t, J=6.6 Hz, 4H), 3.46-3.57 (m, 2H), 4.10 (t, J=6.4 Hz, 2H), 5.27-5.45 (m, 8H)

EXAMPLE 35

2-(1-Methylpyrrolidin-2-yl)ethyl ((9Z,12Z)-octadeca-9,12-dienyl)(2-(9Z,12Z)-octadeca-9,12-dienyloxy)ethyl)carbamate (Compound A-30)

Compound A-30 (0.140 g, yield: 91%) was obtained in the same manner as in Example 10 by using Compound B-8 (0.120 g, 0.215 mmol) obtained in Example 19 in place of Compound B-1.

ESI-MS m/z: 714 (M+H)$^+$; $^1$H-NMR (CDCl$_3$) δ: 0.89 (t, J=6.8 Hz, 6H), 1.21-1.40 (m, 32H), 1.45-1.59 (m, 6H), 1.64-1.82 (m, 2H), 1.93-2.17 (m, 12H), 2.31 (s, 3H), 2.70-2.81 (m, 4H), 3.06 (t, J=7.8 Hz, 1H), 3.20-3.31 (m, 2H), 3.40 (t, J=5.9 Hz, 4H), 3.46-3.58 (m, 2H), 4.06-4.17 (m, 2H), 5.28-5.44 (m, 8H)

EXAMPLE 36

3-(Azepan-1-yl)propyl ((9Z,12Z)-octadeca-9,12-dienyl) (2-((9Z,12Z)-octadeca-9,12-dienyloxy)ethyl) carbamate (Compound A-31)

Compound A-31 (0.170 g, yield: 85%) was obtained in the same manner as in Example 10 by using Compound E-8 (0.150 g, 0.269 mmol) obtained in Example 19 in place of Compound B-1 and Compound VI-9 (0.145 g, 0.403 mmol) obtained in Reference Example 17 in place of Compound VI-3.

ESI-MS m/z: 742 (M+H)$^+$; $^1$H-NMR (CDCl$_3$) δ: 0.89 (t, J=6.8 Hz, 6H), 1.21-1.39 (m, 32H), 1.18-1.65 (m, 12H), 1.72-1.85 (m, 2H), 2.05 (q, J=6.6 Hz, 8H), 2.55 (t, J=7.5 Hz, 2H), 2.61 (t, J=5.3 Hz, 4H), 2.77 (t, J=5.9 Hz, 4H), 3.21-3.30 (m, 2H), 3.40 (t, J=6.8 Hz, 4H), 3.46-3.55 (m, 2H), 4.10 (t, J=6.4 Hz, 2H), 5.26-5.42 (m, 8H)

EXAMPLE 37

(1-Methylpiperidin-3-yl)methyl ((9Z,12Z)-octadeca-9,12-dienyl)(2-((Z,12Z)-octadeca-9,12-dienyloxy) ethyl)carbamate (Compound A-32)

Compound A-32 (0.145 g, yield: 76%) was obtained in the same manner as in Example 10 by using Compound B-8

(0.150 g, 0.269 mmol) obtained in Example 19 in place of Compound B-1 and Compound VI-7 (0.133 g, 0.403 mmol) obtained in Reference Example 15 in place of Compound VI-3.

ESI-MS m/z: 714 (M+H)$^+$; $^1$H-NMR (CDCl$_3$) δ: 0.91 (t, J=6.8 Hz, 6H), 1.23-1.45 (m, 32H), 1.49-1.77 (m, 9H), 1.83-2.03 (m, 2H), 2.07 (q, J=6.6 Hz, 8H), 2.28 (s, 3H), 2.76-2.91 (m, 2H), 2.80 (t, J=5.9 Hz, 4H), 3.21-3.33 (m, 2H), 3.43 (t, J=6.4 Hz, 4H), 3.48-3.58 (m, 2H), 3.85-4.05 (m, 2H), 5.30-5.47 (m, 8H)

REFERENCE EXAMPLE 21

2-((Z)-Octadec-9-enyloxy) ethyl methanesulfonate (Compound IIIc-2)

Compound IIIc-2 (1.29 g, yield: 57%) was obtained in the same manner as in Example 8 by using (Z)-octadec-9-en-1-yl methanesulfonate (2.00 g, 5.77 mmol) in place of (9Z,12Z)-octadeca-9,12-dien-1-yl methanesulfonate.

ESI-MS m/z: 391 (M+H)$^+$; $^1$H-NMR (CDCl$_3$) δ: 0.89 (t, J=6.6 Hz, 3H), 1.22-1.38 (m, 22H), 1.50-1.62 (m, 2H), 1.97-2.05 (m, 4H), 3.06 (s, 3H), 3.48 (t, J=6.8 Hz, 2H), 3.67-3.72 (m, 2H), 4.36-4.39 (m, 2H), 5.35 (t, J=5.5 Hz, 2H)

REFERENCE EXAMPLE 22

2-((Z)-Hexadec-9-enyloxy) ethyl methanesulfonate (Compound IIIc-3)

Compound IIIc-3 (1.52 g, yield: 67%) was obtained in the same manner as in Example 8 by using (Z)-hexadec-9-en-1-yl methanesulfonate (2.00 g, 6.28 mmol) in place of (9Z,12Z)-octadeca-9,12-dien-1-yl methanesulfonate.

ESI-MS m/z: 363 (M+H)$^+$; $^1$H-NMR (CDCl$_3$) δ: 0.90 (t, J=6.6 Hz, 3H), 1.25-1.38 (m, 18H), 1.53-1.62 (m, 2H), 1.98-2.06 (m, 4H), 3.07 (s, 3H), 3.49 (t, J 6.6 Hz, 2H), 3.68-3.72 (m, 2H), 4.36-4.40 (m, 2H), 5.36 (t, J=5.5 Hz, 2H)

EXAMPLE 38

(9Z,12Z)—N-(2-((Z)-Octadec-9-enyloxy)ethyl)octadeca-9,12-diene-1-amine (Compound B-9)

Compound B-9 (0.600 g, yield: 60%) was obtained in the same manner as in Example 13 by using Compound IId-1 (0.800 g, 1.78 mmol) obtained in Reference Example 7 and Compound IIIc-2 (0.728 g, 1.86 mmol) obtained in Reference Example 21 in place of 1-bromododecane.

ESI-MS m/z: 560 (M+H)$^4$; $^1$H-NMR (CDCl$_3$) δ: 0.86-0.94 (m, 6H), 1.24-1.39 (m, 40), 1.51-1.62 (m, 2H), 1.96-2.10 (m, 8H), 2.68 (t, J=7.3 Hz, 2H), 2.78 (t, J=6.0 Hz, 2H), 2.85 (t, J=5.1 Hz, 2H), 3.45 (t, J=6.8 Hz, 2H), 3.57 (t, J=5.1 Hz, 2H), 5.30-5.44 (m, 6H)

EXAMPLE 39

(9Z,12Z)—N-(2-((Z)-Hexadec-9-enyloxy)ethyl) octadeca-9,12-dien-1-amine (Compound B-10)

Compound B-10 (0.550 g, yield: 76%) was obtained in the same manner as in Example 13 by using Compound IId-1 (0.610 g, 1.35 mmol) obtained in Reference Example 7 and Compound IIIc-3 (0.589 g, 1.62 mmol) obtained in Reference Example 22 in place of 1-bromododecane.

ESI-MS m/z: 532 (M+H)$^+$; $^1$H-NMR (CDCl$_3$) δ: 0.85-0.93 (m, 6H), 1.23-1.36 (m, 34H), 1.45-1.54 (m, 4H), 1.94-2.11 (m, 8H), 2.60 (t, J=7.3 Hz, 2H), 2.77 (t, J=5.4 Hz, 4H), 3.43 (t, J=6.8 Hz, 2H), 3.53 (t, J=5.4 Hz, 2H), 5.29-5.44 (m, 6H)

EXAMPLE 40

3-Piperidin-1-yl)propyl (2-((Z)-octadec-9-enyloxy) ethyl)((9Z,12Z)-octadeca-9,12-dienyl)carbamate (Compound A-33)

Compound A-33 (0.137 g, yield: 81%) was obtained in the same manner as in Example 10 by using Compound B-9 (0.130 g, 0.232 mmol) obtained in Example 38 in place of Compound B-1 and Compound VI-4 (0.120 g, 0.348 mmol) obtained in Reference Example 5 in place of Compound VI-3.

ESI-MS m/z: 729 (M+H)$^+$; $^1$H NMR (CDCl$_3$) δ: 0.84-0.92 (m, 6H), 1.20-1.36 (m, 38H), 1.40-1.62 (m, 10H), 1.77-1.87 (m, 2H), 1.96-2.09 (m, 8H), 2.37 (t, J=7.5 Hz, 6H), 2.77 (t, J=5.9 Hz, 2H), 3.20-3.31 (m, 2H), 3.40 (t, J=6.6 Hz, 4H), 3.45-3.56 (m, 2H), 4.10 (t, J=6.4 Hz, 2H), 5.28-5.44 (m, 6H)

EXAMPLE 41

2-(1-Methylpyrrolidin-2-yl)ethyl (2-((Z)-octadec-9-enyloxy)ethyl)((9Z,12Z)-octadeca-9,12-dienyl)carbamate (Compound A-34)

Compound A-34 (0.131 g, yield: 79%) was obtained in the same manner as in Example 10 by using Compound R-9 (0.130 g, 0.232 mmol) obtained in Example 38 in place of compound B-1.

ESI-MS m/z: 716 (M+H)$^+$; $^1$H-NMR (CDCl$_3$) δ: 0.85-0.92 (m, 6H), 1.20-1.39 (38H, in), 1.47-1.61 (m, 8H), 1.66-1.83 (n, 2H), 1.93-2.18 (10H, m), 2.32 (s, 3H), 2.78 (t, J=5.9 Hz, 2H), 3.07 (t, J=8.4 Hz, 1H), 3.21-3.31 (m, 2H), 3.41 (t, J=6.6 Hz, 4H), 3.47-3.56 (m, 2H), 4.08-4.19 (m, 2H), 5.29-5.43 (m, 6H)

EXAMPLE 42

3-(Dimethylamino)propyl (2-((Z)-octadec-9-enyloxy)ethyl)((9Z,12Z)-octadeca-9,12-dienyl)carbamate (Compound A-35)

Compound A-35 (0.100 g, yield: 63%) was obtained in the same manner as in Example 10 by using Compound B-9 (0.130 q, 0.232 mmol) obtained in Example 38 in place of Compound B-1 and Compound VI-1 (0.106 g, 0.348 mol) in place of Compound VI-3.

ESI-MS m/z: 690 (M+H)$^+$; $^1$H-NMR (CDCl$_3$) δ: 0.85-0.92 (m, 6H), 1.20-1.39 (m, 38H), 1.45-1.59 (m, 4H), 1.74-1.84 (m, 2H), 1.96-2.09 (m, 8H), 2.23 (s, 6H), 2.34 (t, J=7.5 Hz, 2H), 2.77 (t, J=5.7 Hz, 2H), 3.21-3.30 (m, 2H), 3.35-3.44 (m, 4H), 3.45-3.55 (m, 2H), 4.11 (t, J=6.4 Hz, 2H), 5.26-5.44 (m, 6H)

EXAMPLE 43

3-(Dimethylamino)propyl (2-((Z)-hexadec-9-enyloxy)ethyl)((9Z,12Z)-octadeca-9,12-dienyl)carbamate (Compound A-36)

Compound A-36 (0.148 g, yield: 79%) was obtained in the same manner as in Example 10 by using Compound B-10 (0.150 g, 0.282 mmol) obtained in Example 39 in place of Compound B-1 and Compound VI-1 (0.095 g, 0.310 mmol) in place of Compound VI-3.

ESI-MS m/z: 662 (M+H)⁺; ¹H-NMR (CDCl₃) δ: 0.85-0.94 (m, 6H), 1.21-1.39 (m, 34H), 1.47-1.59 (m, 4H), 1.76-1.84 (m, 2H), 1.94-2.09 (m, 8H), 2.23 (s, 6H), 2.34 (t, J=7.3 Hz, 2H), 2.77 (t, J=6.3 Hz, 2H), 3.20-3.31 (m, 2H), 3.31-3.45 (m, 4H), 3.45-3.57 (m, 2H), 4.11 (t, J=6.3 Hz, 2H), 5.27-5.46 (m, 6H)

EXAMPLE 44

3-(Piperidin-1-yl)propyl (2-((Z)-hexadec-9-enyloxy)ethyl)((9Z,12Z)-octadeca-9,12-dienyl)carbamate (Compound A-37)

Compound A-37 (0.148 g, yield: 75%) was obtained in the same manner as in Example 10 by using Compound B-10 (0.150 g, 0.282 mmol) obtained in Example 39 in place of Compound B-1 and Compound VI-4 (0.107 g, 0.310 mmol) obtained in Reference Example 5 in place of Compound VI-3.

ESI-MS m/z: 702 (M+H)⁺; ¹H-NMR (CDCl₃) δ: 0.82-0.96 (m, 6H), 1.23-1.39 (m, 34H), 1.39-1.48 (m, 2H), 1.49-1.61 (m, OH), 1.79-1.86 (m, 2H), 1.95-2.09 (m, 8H), 2.33-2.42 (m, 6H), 2.78 (t, J=0.8 Hz, 2H), 3.21-3.32 (m, 2H), 3.34-3.44 (m, 4H), 3.46-3.56 (m, 2H), 4.10 (t, J=6.3 Hz, 2H), 5.29-5.44 (m, 6H)

EXAMPLE 45

3-(Di((Z)-octadec-9-enyl)amino)propan-1-ol (Compound C-2)

Step 1:
Ethyl 3-(di(Z)-octadec-9-enyl)amino)propionate (548 mg, yield: 92%) was obtained in the same manner as in Reference Example 11 by using Compound b-2 (500 mg, 0.965 mmol) obtained in Example 2 in place of Compound B-1.

Step 2:
Compound C-2 (0.445 g, yield: 87%) was obtained in the same manner as in Example 21 by using ethyl 3-(di((Z)-octadec-9-enyl)amino)propionate (548 mg, 0.887 mmol) in place of Compound XI-6.

ESI-MS m/z: 577 (M+H)⁺; ¹H-NMR (CDCl₃) δ: 0.88 (t, J=6.9 Hz, 6H), 1.24-1.42 (m, 44H), 1.42-1.50 (m, 4H), 1.65-1.70 (m, 2H), 2.01 (q, J 6.4 Hz, 8H), 2.40 (t, J=7.5 Hz, 4H), 2.63 (t, J=5.5 Hz, 2H), 3.79 (t, J=5.3 Hz, 2H), 5.30-5.39 (m, 4H)

EXAMPLE 46

3-(Di((11Z,14Z)-icosa-11,14-dienyl)amino)propan-1-ol (Compound C-3)

Step 1:
Ethyl 3-(di(11Z,14Z)-icosa-11,14-dienyl)amino)propionate (548 mg, yield: 90%) was obtained in the same manner as in Reference Example 11 by using Compound B-4 (400 mg, 0.702 mmol) obtained in Example 4 in place of Compound B-1.

Step 2:
Compound C-3 (352 mg, yield: 88%), was obtained in the same manner as in Example 21 by using ethyl 3-(di((11Z,14Z)-icosa-11,14-dienyl)amino)propionate (424 mg, 0.633 mmol) in place of Compound XI-6.

ESI-MS m/z: 629 (M+H)⁺; ¹H-NMR (CDCl₃) δ: 0.89 (t, J=6.9 Hz, 6H), 1.24-1.40 (m, 40H), 1.42-1.50 (m, 4H), 1.64-1.70 (m, 2H), 2.02-2.08 (m, 8H), 2.40 (t, J=7.5 Hz, 4H), 2.63 (t, J=5.3 Hz, 2H), 2.78 (t, J=6.4 Hz, 4H), 3.79 (t, J=5.0 Hz, 2H), 5.29-5.42 (m, 8H)

EXAMPLE 47

2-(Di((9Z,12Z)-octadeca-9,12-dienyl)amino)ethanol (Compound C-4)

Step 1:
To a solution of Compound H-1 (600 mg, 1.17 mmol) obtained in Example 1 in 1,2-dichloroethane (2.0 mL), potassium carbonate (243 mg, 1.76 mmol) and ethyl bromoacetate (195 μL, 1.76 mmol) were added, followed by stirring overnight at 85° C. To the obtained mixture, water was added, and the mixture was extracted two times with heptane. The organic layers were combined, washed with water, and dried over anhydrous sodium sulfate. The resultant was filtered and concentrated under reduced pressure. The residue was purified by amino-silica gel column chromatography (heptane/ethyl acetate=100/0 to 95/5), whereby ethyl 2-(di((9Z,12Z)-octadeca-9,12-dienyl)amino)acetate (527 mg, yield: 75%) was obtained.

Step 2:
Compound C-4 (433 mg, yield: 88%) was obtained in the same manner as in Example 21 by using ethyl 2-(di((9Z,12Z)-octadeca-9,12-dienyl)amino)acetate (527 mg, 0.878 mmol) in place of Compound XI-6.

ESI-MS m/z: 559 (M+H)⁺; ¹H-NMR (CDCl₃) δ: 0.89 (t, J=6.9 Hz, 6H), 1.24-1.39 (m, 32H), 1.39-1.46 (m, 4H), 2.02-2.08 (m, 8H), 2.43 (t, J=7.5 Hz, 4H), 2.57 (t, J=5.3 Hz, 2H), 2.77 (t, J=6.2 Hz, 4H), 3.52 (t, J=5.5 Hz, 2I), 5.29-5.41 (m, 8H)

EXAMPLE 48

4-(Di((9Z,12Z)-octadeca-9,12-dienyl)amino)butan-1-ol (Compound C-5)

Step 1:
To a solution of Compound B-1 (500 mg, 0.973 mmol) obtained in Example 1 in 1,2-dichloroethane (2.0 mL), potassium carbonate (202 mg, 1.46 mmol) and tert-butyl(4-iodobutoxy)dimethylsilane (manufactured by SIGMA-ALDRICH Co., Ltd., 378 μL, 1.46 mmol) were added, followed by stirring at 85° C. for 4 hours. To the obtained mixture, water was added, and the mixture was extracted two times with heptane. The organic layers were combined, washed with water, and dried over anhydrous sodium sulfate. The resultant was filtered and concentrated under reduced pressure. The residue was purified by silica gel column chromatography (heptane/ethyl acetate=95/5 to 80/20), whereby (4-(tert-butyldimethylsilyloxy)butyl)di((9Z,12Z)-octadeca-9,12-dienyl)amine (233 mg, yield: 34%) was obtained.

Step 2:
To a solution of (4-(tert-butyldimethylsilyloxy)butyl)di(9Z,12Z)-octadeca-9,12-dienyl)amine (233 mg, 0.333 mmol) in tetrahydrofuran (5 mL), tetrabutylammonium fluoride (1 mol/L tetrahydrofuran solution, 0.666 mL, 0.666 mmol) was added, followed by stirring overnight at room temperature. To the obtained mixture, saturated brine was added, and the mixture was extracted with ethyl acetate. The organic layer was dried over anhydrous sodium sulfate, filtered, and concentrated under reduced pressure. The residue was purified by amino-silica gel column chromatography (heptane/ethyl acetate=90/10) and further purified by silica gel column chromatography (ethyl acetate/methanol=100/0 to 90/10), whereby Compound C-5 (160 mg, yield: 82%) was obtained.

ESI-MS m/z: 587 (M+H)$^+$; $^1$H-NMR (CDCl$_3$) δ: 0.89 (t, J=6.9 Hz, 6H), 1.23-1.40 (m, 32H), 1.43-1.51 (m, 4H), 1.62-1.68 (m, 4H), 2.05 (q, J=7.0 Hz, 8H), 2.41-2.45 (m, 6H), 2.77 (t, J=6.6 Hz, 4H), 3.53-3.56 (m, 2H), 5.29-5.42 (m, 8H)

REFERENCE EXAMPLE 23

3-(Dimethylamino)propyl 2,3-bis((9Z,12Z)-octadeca-9,12-dienyloxy)propyl(methyl)carbamate (Compound XI-9)

Step 1:

To a solution of 2,3-bis((9Z,12Z)-octadeca-9,12-dienyloxy)propan-1-ol (0.303 g, 0.514 mmol) synthesized by the method described in WO2009/129395 in dichloromethane (4 mL), triethylamine (0.108 mL, 0.772 mmol) and mesylic acid chloride (0.060 mL, 0.772 mmol) were added at 0° C., followed by stirring at room temperature for 3 hours. To the reaction mixture, a saturated aqueous sodium bicarbonate solution was added, and the mixture was extracted with ethyl acetate. The resultant was washed with saturated brine and dried over anhydrous magnesium sulfate. Thereafter, the resultant was filtered and concentrated under reduced pressure.

The obtained residue was dissolved in dichloromethane (4 mL), and methylamine (7 mol/L methanol solution, 2.20 mL) was added thereto, followed by stirring at 110° C. for 5 minutes using a micro wave reactor. To the reaction mixture, water was added, and the mixture was extracted with n-hexane. The resultant was washed with saturated brine and dried over anhydrous magnesium sulfate. The resultant was filtered and concentrated under reduced pressure. The obtained residue was purified by amino-silica gel column chromatography (n-hexane/ethyl acetate=95/5 to 70/30), whereby N-methyl-2,3-bis((9Z,12Z)-octadeca-9,12-dien-1-yloxy)propan-1-amine (0.278 g, yield: 90%).

ESI-MS m/z: 603 (M+H)$^+$; $^1$H-NMR (CDCl$_3$) δ: 0.89 (t, J=7.1 Hz, 6H), 1.27-1.39 (m, 34H), 1.51-1.58 (m, 3H), 2.05 (q, J=7.1 Hz, 8H), 2.44 (s, 3H), 2.64-2.70 (m, 2H), 2.77 (t, J=6.9 Hz, 4H), 3.41-3.50 (m, 5H), 3.54-3.58 (m, 1H), 3.61-3.65 (m, 1H), 5.30-5.41 (m, 8H)

Step 2:

To a suspension of N-methyl-2,3-bis(9Z,12Z)-octadeca-9,12-dien-1-yloxy)propan-1-amine (0.220 g, 0.365 mmol) in acetonitrile (2 mL), Compound VI-1 (0.167 g, 0.548 mmol) and triethylamine (0.255 mL, 1.827 mmol) were added, followed by stirring overnight at 80° C. The reaction mixture was diluted with a saturated aqueous sodium bicarbonate solution and extracted with ethyl acetate. The organic layer was washed with saturated brine and dried over anhydrous magnesium sulfate. Thereafter, the resultant was filtered and concentrated under reduced pressure. The residue was purified by amino-silica gel column chromatography (n-hexane/ethyl acetate=80/20 to 65/35), whereby Compound XI-9 (0.178 g, yield: 67%) was obtained.

ESI-MS m/z: 732 (M+H)$^+$; $^1$H-NMR (CDCl$_3$) δ: 0.89 (t, 0.7=6.9 Hz, 6H), 1.26-1.38 (m, 32H), 1.51-1.59 (m, 4H), 1.77-1.83 (m, 2H), 2.05 (q, J=7.0 Hz, 8H), 2.22 (s, 6H), 2.34 (t, J=7.4 Hz, 2H), 2.77 (t, J=6.8 Hz, 4H), 2.97 (s, 3H), 3.19-3.25 (m, 1H), 3.38-3.65 (m, 8H), 4.12 (t, J=6.3 Hz, 2H), 5.30-5.41 (m, 8H)

EXAMPLE 49

Compositions were prepared as follows by using the compounds (Compounds A-1 to A-5) obtained in Examples 5 to 9. The used nucleic acid is an anti-APO-B siRNA, which suppresses the expression of an apolipoprotein-B (hereinafter, represented by "apo-b") gene, and is composed of the base sequence of a sense strand [5'-rGmUrCrAmUr-CrArCrArCmUrGrArAmUrArCrCrArAmU-3' (the sugars attached to the bases marked with r are riboses, and marked with m are riboses having —O-methyl substituted for the hydroxyl group at the 2' position)] and an antisense strand [5'-rArUrUrGrGrUrArUrUrCrArGrUrGrUrGrArUrGrAr-CrArC-3' (all the sugars attached to the bases are riboses, and the 5' end is phosphorylated)], and was obtained from Gene Design, Inc. (hereinafter referred to as "apo-b siRNA").

Each sample was weighed so that the ratio of each of Compounds A-1 to A-5/1,2-dimyristoyl-sn-glycero-3-phosphoethanolamine-N-(methoxy(polyethylene glycol)-2000) sodium salt (PEG-DMPE Na, N-(carbonylmethoxypolyethylene glycol 2000)-1,2-dimyristoyl-sn-glycero-3-phosphoethanolamine sodium salt, manufactured by NOF Corporation)/distearoylphosphatidyl choline (DSPC, 1,2-distearoyl-sn-glycero-3-phosphocholine, manufactured by NOF Corporation)/cholesterol (manufactured by NOF Corporation)=8.947/1.078/5.707/13.698 mmol/L, and dissolved in 90 vol % ethanol, whereby a solution containing the constituent components of a lipid membrane was prepared. Separately, apo-b siRNA in distilled water (24 mg/mL) was diluted with a Tris-EDTA buffer solution (200 mM Tris-HCl, 20 mM EDTA, manufactured by Invitrogen Co., Ltd.) and a 20 mM citric acid buffer solution (pH 5.0), whereby a 1.5 mg/mL apo-b siRNA aqueous solution (2 mM Tris-EDTA buffer solution, 20 mM citric acid buffer solution, pH 5.0) was prepared.

The obtained lipid solution was heated to 37° C., and a 500 µL portion was transferred to a container for preparing a preparation. The obtained apo-b siRNA aqueous solution (500 µL) was then added thereto while stirring. Then, a 20 mM citric acid buffer solution (containing 300 mM NaCl, pH 6.0, 1000 µL) was added to the obtained lipid nucleic acid mixed suspension (1,000 µL) while stirring, and further, 3,310 µL of DPBS (Dulbecco's phosphate-buffered saline, manufactured by Invitrogen Co., Ltd.) was added dropwise thereto, whereby a crude preparation was obtained. The obtained crude preparation was concentrated by using Amicon Ultra (manufactured by Millipore Co., Ltd.) and then diluted with DPBS, and the resulting mixture was filtered through a 0.2-µm filter (manufactured by Toyo Roshi Kaisha, Ltd.) in a laminar flow cabinet. The siRNA concentration in the obtained composition was measured, and the composition was diluted with DPBS so that the siRNA concentration was 0.3 or 0.03 mg/mL, whereby preparations (compositions containing any of Compounds A-1 to A-5, and the nucleic acid) were obtained.

The average particle diameter of each preparation (composition) was measured using a particle diameter measurement device (Zetasizer Nano ZS, manufactured by Malvern, hereafter the same). The results are shown in Table 8.

TABLE 8

| Compound No. | A-1 | A-2 | A-3 | A-4 | A-5 |
|---|---|---|---|---|---|
| Particle diameter of Preparation obtained (nm) | 151.8 | 135.8 | 150.0 | 159.0 | 137.0 |

COMPARATIVE EXAMPLE 1

Preparations were obtained in the same manner as in Example 49 except that Compounds 1 were changed to DLin-KC2-DMA synthesized by a modified method of the method described in Patent Document 1 and the compounds obtained in Reference Examples 1 to 3 (Compounds XI-1 to XI-3).

The structural formulae of the compounds (DLin-KC2-DMA and Compounds XI-1 to XI-3) used in the comparative example are shown in Table 9.

The average particle diameter of each preparation (composition) was measured using a particle diameter measurement device. The results are shown in Table 10.

TABLE 9

| Compound | Structural formula |
|---|---|
| DLin-KC2-DMA | (structure) |
| XI-1 | (structure) |
| XI-2 | (structure) |
| XI-3 | (structure) |

TABLE 10

| Compound No. | DLin-KC2-DMA | XI-1 | XI-2 | XI-3 |
|---|---|---|---|---|
| Particle diameter of Preparation obtained (nm) | 159.8 | 176.6 | 160.1 | 177.7 |

TEST EXAMPLE 1

Each of the preparation: obtained in Example 49 (the compositions containing any of Compounds A-1, and A-3 to A-5, and the nucleic acid) and the preparations obtained in Comparative Example 1 (the compositions containing any of DLin-KC2-DMA and Compounds XI-1 to XI-3, and the nucleic acid) was introduced into cells of human liver cancer-derived cell line HepG2 (HB-8065) by the following method.

Each preparation diluted with Opti-MEM (GIBCO Co., Ltd., 31985) so that the final concentration of the nucleic acid was 3 to 100 nM was dispensed in a 96-well culture plate at 20 μL/well. Then, HepG2 cells suspended in Opti-MEM containing 1.25% fetal bovine serum (FBS, SAFC Biosciences, Inc., 12203C) were inoculated at 6250 cells/80 μL/well, and cultured under the conditions of 37° C. and 5% $CO_2$, thereby introducing the preparation into the HepG2 cells. In addition, untreated cells were inoculated as a negative control group.

The cells after the introduction of the preparation were cultured in a 5% $CO_2$ incubator at 37° C. for 24 hours, and then washed with ice-cooled phosphate buffered saline (PBS, GIBCO Co., Ltd., 14190). Thereafter, by using a Cells-to-Ct Kit (Applied Biosystems (ABI), Inc., AM1728), the total RNA was collected, and cDNA was synthesized by a reverse transcription reaction using the obtained total RNA as a template according to the method described in the protocol attached to the kit.

By using the obtained cDNA as a template and also using a universal probe library (Roche Applied Science, Inc., 04683633001) as the probe and ABI7900HT Fast (manufactured by ABI, Inc.), a PCR reaction was performed according to the method described in the protocol attached thereto, so that the apo-b gene and D-glyceraldehyde-3-phosphate dehydrogenase (hereinafter, represented by "gapdh") gene, which is a constitutively expressed gene, were subjected to the PCR reaction. Then, the amount of the amplified mRNA was measured for each gene, and a quasi-quantitative value of the apo-b mRNA was calculated using the amount of the amplified gapdh mRNA as the internal control. The expression ratio of the apo-b mRNA was determined from the quasi-quantitative value of the apo-b mRNA while a quasi-quantitative value of the apo-b mRNA in the negative control group as measured in the same manner was taken as 1. The results of the obtained expression ratio of the apo-b mRNA are shown in FIG. 1.

As apparent from FIG. 1, the preparations obtained in Example 49 (the compositions containing any of Compounds A-1, and A-3 to A-5, and the nucleic acid), and among the preparations obtained in Comparative Example 1, the compositions containing DLin-KC2-DMA, Compound XI-1, or Compound XI-3, and the nucleic acid suppressed the expression of the apo-b gene mRNA after the introduction thereof into the cells of the human liver cancer-derived cell line HepG2. On the other hand, among the preparations obtained in Comparative Example 1, the composition containing Compound XI-2 and the nucleic acid did not suppress the expression of the apo-b gene mRNA after the introduction thereof into the cells of the human liver cancer-derived cell line HepG2.

TEST EXAMPLE 2

Each of the preparations obtained in Example 49 (the compositions containing any of Compounds A-1 to A-5, and the nucleic acid) and the preparations obtained in Comparative Example 1 (the compositions containing any of DLin-KC2-DMA and Compounds XI-1 to XI-3, and the nucleic acid) was tested for evaluating the in vivo drug efficacy according to the following method. Incidentally, each preparation was used after it was diluted with DPBS in accordance with the test.

After mice (Balb/c, obtained from CLEA Japan, Inc.) were housed and acclimated, each preparation was intravenously administered to mice at a dose of 3 or 0.3 mg/kg in terms of siRNA concentration. At 48 hours after the administration, blood was collected, and the collected blood was centrifuged at 3,000 rpm for 20 minutes at 4° C. using a refrigerated microcentrifuge (05PR-22, manufactured by Hitachi, Ltd.). A Cholesterol Assay Kit (Cat. No. 10007640, manufactured by Cayman Chemical Company) was used, and according to the method described in the protocol attached to the kit, the intensity of fluorescence was measured in a standard solution and in the serum sample using ARVO (530 nm/595 nm) or EnVision (531 nm/595 mm). On the basis of the obtained intensity of fluorescence, a calibration curve was prepared, and the cholesterol level in the serum was calculated.

The results of the calculated cholesterol level in the serum are shown in FIGS. 2 and 3.

As apparent from FIGS. 2 and 3, the measurement results of the cholesterol level obtained by testing the preparations obtained in Example 49 (the compositions containing anti-APO-B siRNA which suppresses the expression of the apo-b gene, and any of Compounds A-1 to A-5) for evaluating the in vivo drug efficacy are lower as compared with the measurement results obtained by using the compositions containing any of Compounds XI-1 to XI-3, and the nucleic acid among the preparations obtained in Comparative Example 1, and it is shown that by administering the preparation obtained in Example 22, the expression of the apo-b gene is strongly suppressed.

Accordingly, it was revealed that the composition of the present invention can introduce a nucleic acid into a cell or the like, and the cationic lipid of the present invention is a cationic lipid which facilitates the in vivo delivery of a nucleic acid into a cell.

EXAMPLE 50

Compositions were prepared as follows by using the compound (Compound A-6) obtained in Example 10. The used nucleic acid is an anti-f7 siRNA, which suppresses the expression of a coagulation factor VII (hereinafter, represented by "f7") gene, and is composed of a sense strand [5'-rGrGrAfUfCrAfUfCfUfCrArArGfUfCfUfUrAfCdTdT-3' (the sugars attached to the bases marked with r are riboses, marked with d are deoxyriboses, and marked with f are riboses having fluorine substituted for the hydroxyl group at the 2' position, and a bond between the deoxyribose attached to the base at the position 20 from the 5' end side to the 3' end side and the deoxyribose attached to the base at the position 21 is a phosphorothioate bond)] and the base sequence of an antisense strand [5'-rGfUrArArGrAfCfUfUr-GrArGrAfUrGrAfUfCfCdTdT-3' (the sugars attached to the bases marked with r are riboses, marked with d are deoxyriboses, and marked with f are riboses having fluorine substituted for the hydroxyl group at the 2' position, and a bond between the deoxyribose attached to the base at the position 20 from the 5' end side to the 3' end side and the deoxyribose attached to the base at the position 21 is a phosphorothioate bond)], and was obtained from Gene Design, Inc. (hereinafter referred to as "f7 siRNA").

Each sample was weighed so that the ratio of Compound A-6/PEG-DMPE Na (manufactured by NOF Corporation)/DSPC (manufactured by NOF Corporation)/cholesterol (manufactured by NOF Corporation)=3.532/0.270/1.156/2.401 mmol/L, and dissolved in 100 vol % ethanol, whereby a solution containing the constituent components of a lipid membrane was prepared. Separately, f7 siRNA in distilled water (24 mg/mL) was diluted with a Tris-EDTA buffer solution (200 mM Tris-HCl, 20 mM EDTA, manufactured by Invitrogen Co., Ltd.) and a 20 mM citric acid buffer solution (pH 4.0), whereby a 0.375 mg/mL f7 siRNA aqueous solution (2 mM Tris-EDTA buffer solution, 20 mM citric acid buffer solution, pH 4.0) was prepared.

The obtained lipid solution was heated to 37° C., and an 800 µL portion was transferred to a container for preparing a preparation. The obtained f7 siRNA aqueous solution (800 µL) was then added thereto while stirring. Then, a 20 mM citric acid buffer solution (containing 300 mM NaCl, pH 6.0, 1,600 µL) was added to the obtained lipid nucleic acid mixed suspension (1,600 µL) while stirring, and further, DPBS (manufactured by Invitrogen Co., Ltd., 7,086 µL) was added dropwise thereto, whereby a crude preparation was obtained. The obtained crude preparation was concentrated by using Amicon Ultra (manufactured by Millipore Co., Ltd.) and then diluted with DPBS, and the resulting mixture was filtered through a 0.45-µm filter (manufactured by Toyo Roshi Kaisha, Ltd.) in a laminar flow cabinet. The siRNA concentration in the obtained composition was measured, and the preparation was diluted with DPBS so that the siRNA concentration was 0.03 mg/mL, whereby a preparation (a composition containing Compound A-6 and the nucleic acid) was obtained.

The average particle diameter of each preparation (composition) was measured using a particle diameter measurement device. The results are shown in Table 11.

EXAMPLE 51

Preparations (compositions containing each of Compounds A-1, A-5, A-7 to A-21, A-28 to A-36, B-1, B-8, and C-1 to C-5, and the nucleic acid) were obtained in the same manner as in Example 50 by using each of Compounds A-1, A-5, A-7 to A-21, A-28 to A-36, B-1, B-8, and C-1 to C-5 among the compounds obtained in Examples 1 to 48.

The average particle diameter of each preparation (composition) was measured using a particle diameter measurement device. The results are shown in Table 11.

TABLE 11

| Compound No. | A-1 | A-5 | A-6 | A-7 | A-8 | A-9 | A-10 | A-11 | A-12 |
|---|---|---|---|---|---|---|---|---|---|
| Particle diameter of Preparation obtained (nm) | 118.9 | 139.2 | 121.1 | 131.8 | 121.6 | 116.4 | 148.7 | 153.4 | 133.0 |
| Compound No. | A-13 | A-14 | A-15 | A-16 | A-17 | A-18 | A-19 | A-20 | A-21 |
| Particle diameter of Preparation obtained (nm) | 135.0 | 134.4 | 124.0 | 133.4 | 129.1 | 138.4 | 140.0 | 145.1 | 141.0 |
| Compound No. | A-28 | A-29 | A-30 | A-31 | A-32 | A-33 | A-34 | A-35 | A-36 |
| Particle diameter of Preparation obtained (nm) | 132.0 | 130.6 | 130.4 | 139.1 | 124.6 | 136.6 | 140.2 | 137.8 | 126.5 |
| Compound No. | B-1 | B-8 | C-1 | C-2 | C-3 | C-4 | C-5 | | |
| Particle diameter of Preparation obtained (nm) | 160.6 | 149.6 | 124.3 | 125.4 | 138.4 | 137.3 | 134.9 | | |

COMPARATIVE EXAMPLE 2

Preparations were obtained in the same manner as in Example 50 except that Compound A-6 was changed to each of the compounds obtained in Reference Examples 9 to 13 (Compounds XI-4 to XI-8).

The structural formulae of the compounds used in Comparative Example 2 (Compounds XI-4 to XI-8) are shown in Table 12.

The average particle diameter of each preparation (composition) was measured using a particle diameter measurement device. The results are shown in Table 13.

TABLE 12

| Compound No. | Structural formula |
|---|---|
| XI-4 | (structure) |
| XI-5 | (structure) |
| XI-6 | (structure) |
| XI-7 | (structure) |
| XI-8 | (structure) |
| XI-9 | (structure) |

TABLE 13

| Compound No. | XI-4 | XI-5 | XI-6 | XI-7 | XI-8 | XI-9 |
|---|---|---|---|---|---|---|
| Particle diameter of Preparation obtained (nm) | 105.3 | 114.1 | 174.2 | 142.8 | 128.0 | 116.2 |

TEST EXAMPLE 3

Each of the preparations obtained in Examples 50 and 51 (compositions containing each of Compounds A-1, A-5 to A-21, A-28 to A-36, B-1, B-8, and C-1 to C-5, and the nucleic acid) and each of the preparations obtained in Comparative Example 2 (compositions containing each of Compounds XI-4 to XI-8, and the nucleic acid) were tested for evaluating the in vivo drug efficacy according to the following method. Incidentally, each preparation was used after it was diluted with DPBS or saline in accordance with the test.

After mice (Balb/c, obtained from CLEA Japan, Inc.) were housed and acclimated, each preparation was intravenously administered to mice at a dose of 0.3, 0.1, and 0.03 mg/kg, respectively in terms of siRNA concentration. At 48 hours after the administration, blood was collected, and the collected blood was centrifuged at 8,000 rpm for 8 minutes at 4° C. using a high speed refrigerated microcentrifuge (TOMY MX305, manufactured by Tomy Seiko Co., Ltd.). A BIOPHEN VII Kit (Cat. No. A221304, manufactured by ANIARA Company) was used, and according to the method described in the protocol attached to the kit, the absorbance was measured in a standard solution and in the plasma sample using ARVO (405 nm). On the basis of the obtained absorbance, a calibration curve was prepared, and the Factor VII protein level in the plasma was calculated. Incidentally, the number of mice in each group was set to 3.

The results of the calculated Factor VII protein level in the plasma are shown in FIGS. 4 to 9.

As apparent from FIGS. 4 to 9, the measurement results of the Factor VII protein level in the plasma obtained by testing each of the preparations obtained in Examples 50 and 51 (the compositions containing anti-Factor VII siRNA which suppresses the expression of the Factor VII gene, and each of Compounds A-6, A-1, A-7 to A-12, B-1, B-8, C-1, A-5, A-13 to A-21, A-28 to A-36, and C-2 to C-5) for evaluating the in vivo drug efficacy show that by administering each of the preparations obtained in Examples 50 and 51, the expression of the Factor VII gene is strongly suppressed.

Accordingly, it was revealed that the composition of the present invention can introduce a nucleic acid into a cell or the like, and the cationic lipid of the present invention is a cationic lipid which facilitates the in vivo delivery of a nucleic acid into a cell.

EXAMPLE 52

By using Compound A-1 obtained in Example 5, compositions were prepared as follows.

As a nucleic acid, the same nucleic acid as in Example 50 was used after it was prepared at 24 mg/mL with distilled water.

Each sample was weighed and suspended in an aqueous solution containing hydrochloric acid and ethanol so that the ratio of Compound A-1/PEG-DMPE Na (manufactured by NOF Corporation) was 57.3/5.52 mmol/L, and then, the resulting mixture was repeatedly subjected to stirring using a vortex stirring mixer and heating, whereby a uniform suspension was obtained. This suspension was passed through a 0.2-μm polycarbonate membrane filter and thereafter passed through a 0.05-μm polycarbonate membrane filter at room temperature, whereby a dispersion liquid of particles (liposome) of Compound A-1/PEG-DMPE Na was obtained. The average particle diameter of the obtained liposome was measured using a particle diameter measuring apparatus to confirm that the average particle diameter was within the range from 30 nm to 100 nm. In the obtained dispersion liquid of liposome, the f7 siRNA solution was mixed at a ratio of the dispersion liquid of liposome to the fl siRNA solution of 3:1, and then, distilled water that was three times the amount was added thereto and mixed therewith, whereby a dispersion liquid of Compound A-1/PEG-DMPE Na/f7 siRNA complex was prepared.

Separately, each sample was weighed so that the ratio of Compound A-1/PEG-DMPE Na (manufactured by NOF Corporation)/DSPC (manufactured by NOF Corporation)/cholesterol (manufactured by NOF Corporation) was 8.947/1.078/5.707/13.698 mmol/L, and dissolved in 90 vol % ethanol, whereby a solution containing the constituent components of a lipid membrane was prepared.

The obtained solution containing the constituent components of a lipid membrane was heated and then mixed with the obtained dispersion liquid of Compound A-1/PFG-DMPE Na/f7 siRNA complex at a ratio of 1/1, and the resulting mixture was further mixed with distilled water that was several times the amount, whereby a crude preparation was obtained.

The obtained crude preparation was concentrated by using Amicon Ultra (manufactured by Millipore Co., Ltd.) and then diluted with saline, and the resulting mixture was filtered through a 0.2-μm filter (manufactured by Toyo Roshi Kaisha, Ltd.) in a laminar flow cabinet. The siRNA concentration in the obtained composition was measured and diluted with saline so that the siRNA concentration was 0.03, 0.01, or 0.003 mg/mL, whereby a preparation (composition containing Compound A-1 and the nucleic acid) was obtained.

The average particle diameter of the preparation (composition) was measured using a particle diameter measurement device. The results are shown in Table 14.

EXAMPLE 53

Preparations (compositions containing each of Compounds A-5 to A-7, A-10, A-12 to A-21, A-28 to A-36, B-8, and C-1 to C-5, and the nucleic acid) were obtained in the same manner as in Example 52 by using each of Compounds A-5 to A-7, A-10, A-12 to A-21, A-28 to A-36, B-8, and C-1 to C-5 among the compounds obtained in Examples 1 to 48.

The average particle diameter of each preparation (composition) was measured using a particle diameter measurement device. The results are shown in Table 14.

TABLE 14

| Compound No. | A-1 | A-5 | A-6 | A-7 | A-10 | A-12 | A-13 | A-14 |
|---|---|---|---|---|---|---|---|---|
| Particle diameter of Preparation obtained (nm) | 95.9 | 93.4 | 93.6 | 94.6 | 123.1 | 111.5 | 103.1 | 99.7 |
| Compound No. | A-15 | A-16 | A-17 | A-18 | A-19 | A-20 | A-21 | A-28 |
| Particle diameter of Preparation obtained (nm) | 98.4 | 105.5 | 101.4 | 112.0 | 91.4 | 95.7 | 104.8 | 111.3 |
| Compound No. | A-29 | A-30 | A-31 | A-32 | A-33 | A-34 | A-35 | A-36 |
| Particle diameter of Preparation obtained (nm) | 103.4 | 106.2 | 102.2 | 101.4 | 98.8 | 92.6 | 115.4 | 127.2 |
| Compound No. | B-8 | C-1 | C-2 | C-3 | C-4 | C-5 | | |
| Particle diameter of Preparation obtained (nm) | 103.7 | 88.3 | 91.9 | 94.1 | 98.8 | 96.4 | | |

COMPARATIVE EXAMPLE 3

A preparation was obtained in the same manner as in Example 52 except that Compound A-1 was changed to Compound XI-9 obtained in Reference Example 23.

A structural formula of the compound (Compound XI-9) used in Comparative Example 3 is shown in Table 12.

The average particle diameter of the preparation (composition) was measured using a particle diameter measurement device. The results are shown in Table 13.

TEST EXAMPLE 4

Each of the preparations obtained in Examples 52 and 53 or preparations obtained in the same manner as in Examples 52 or 53 (compositions containing each of Compounds A-1, A-5 to A-7, A-10, A-12 to A-21, A-28 to A-36, B-8, and C-1 to C-5, and the nucleic acid) and the preparation obtained in Comparative Example 3 (composition containing Compound XI-9 and the nucleic acid) were tested for evaluating the in vivo drug efficacy in the same manner as in Test Example 3. The results of the calculated Factor VII protein level in the plasma are shown in FIGS. 10 to 13.

EXAMPLE 54

By using each of the compounds (Compounds A-1, A-7, and A-10) obtained in Examples 5, 11, and 17, compositions were prepared as follows. As a nucleic acid, the same nucleic acid as in Example 50 was used.

Each sample was weighed so that the ratio of each of A-1, A-7, and A-10/PEG-DMPE Na (manufactured by NOF Corporation)/DSPC (manufactured by NOF Corporation)/cholesterol (manufactured by NOF Corporation)=7.030/0.755/2.038/4.892 mmol/L, and dissolved in 100 vol % ethanol, whereby a solution containing the constituent components of a lipid membrane was prepared. Separately, f7 siRNA in distilled water (24 mg/mL) was diluted with a Tris-EDTA buffer solution (200 mM Tris-HCl, 20 mM EDTA, manufactured by Invitrogen Co., Ltd.) and a 20 mM citric acid buffer solution (pH 4.0), whereby a 0.536 mg/mL f7 siRNA aqueous solution (2 mM Tris-EDTA buffer solution, 20 mM citric acid buffer solution, pH 4.0) was prepared.

The obtained lipid solution was heated to 37° C., and an 560 µL portion was transferred to a container for preparing a preparation. The obtained f7 siRNA aqueous solution (560 µL) was then added thereto while stirring. Then, a 20 mM citric acid buffer solution (containing 300 mM NaCl, pH 6.0, 1,120 µL) was added to the obtained lipid nucleic acid mixed suspension (1,120 µL) while stirring, and further, DPBS (manufactured by Invitrogen Co., Ltd., 4,960 µL) was added dropwise thereto, whereby a crude preparation was obtained. The obtained crude preparation was concentrated by using Amicon Ultra (manufactured by Millipore Co., Ltd.) and then diluted with DPBS, and the resulting mixture was filtered through a 0.45-µm filter (manufactured by Toyo Roshi Kaisha, Ltd.) in a laminar flow cabinet. The siRNA concentration in the obtained composition was measured, and the preparation was diluted with DPBS so that the siRNA concentration was 0.03 or 0.01 mg/mL, whereby preparations (compositions containing each of Compound A-1, A-7, and A-10, and the nucleic acid) were obtained.

The average particle diameter of each preparation (composition) was measured using a particle diameter measurement device. The results are shown in Table 15.

TABLE 15

| Compound No. | A-1 | A-7 | A-10 |
|---|---|---|---|
| Particle diameter of Preparation obtained (nm) | 113.0 | 123.3 | 156.2 |

TEST EXAMPLE 5

Each of the preparations obtained in Examples 54 (compositions containing each of Compounds A-1, A-7, and A-10, and the nucleic acid) was tested for evaluating the in vivo drug efficacy in the same manner as in Test Example 3. The results of the calculated Factor VII protein level in the plasma are shown in FIG. 14.

INDUSTRIAL APPLICABILITY

By administering a composition containing the cationic lipid of the present invention and a nucleic acid to a mammal or the like, the nucleic acid can be easily introduced into, for example, a cell or the like.

SEQUENCE LISTING FREE TEXT

SEQ No. 1: Apolipoprotein-B siRNA sense strand
SEQ No. 2: Apolipoprotein-B siRNA antisense strand
SEQ No. 3: Coagulation factor VII siRNA sense strand
SEQ No. 4: Coagulation factor VII siRNA antisense strand

The invention claimed is:

1. A cationic lipid represented by: formula (C):

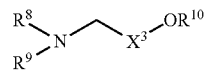

wherein:
- $R^8$ is linear alkenyl having 12 to 24 carbon atoms,
- $R^9$ is linear or branched alkyl or alkenyl, each having 8 to 24 carbon atoms,
- $X^3$ is alkylene having 1 to 3 carbon atoms, and
- $R^{10}$ is a hydrogen atom,
- with the provisos that $R^8$ is not (Z)-octadec-9-enyl, $R^9$ is not (Z)-octadec-9-enyl and $X^3$ is not methylene at the same time,
- $R^8$ is not (Z)-octadec-9-enyl, $R^9$ is not (Z)-octadec-9-enyl and $X^3$ is not ethylene at the same time, and
- $R^8$ is not (Z)-octadec-9-enyl, $R^9$ is not octadecyl and $X^3$ is not methylene at the same time.

2. The cationic lipid according to claim 1, wherein $R^8$ is (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, or (Z)-docos-13-enyl.

3. The cationic lipid according to claim 1, wherein $R^8$ is (Z)-hexadec-9-enyl, (Z)-octadec-6-enyl, (Z)-octadec-9-enyl, (9Z,12Z)-octadeca-9,12-dienyl, (Z)-icosa-11-enyl, or (11Z,14Z)-icosa-11,14-dienyl.

4. The cationic lipid according to claim 1, wherein $X^3$ is methylene or ethylene.

5. A composition comprising: a cationic lipid represented by formula (C):

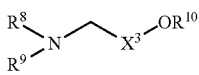

wherein:
- $R^8$ is linear or branched alkenyl having 8 to 24 carbon atoms,
- $R^9$ is linear or branched alkyl or alkenyl, each having 8 to 24 carbon atoms,
- $X^3$ is alkylene having 1 to 3 carbon atoms, and
- $R^{10}$ is a hydrogen atom, and a nucleic acid.

6. The composition according to claim 5, wherein the cationic lipid and the nucleic acid form a complex, or a combination of a neutral lipid and/or a polymer with the cationic lipid and the nucleic acid form a complex.

7. The composition according to claim 5, wherein the cationic lipid and the nucleic acid form a complex, or a combination of a neutral lipid and/or a polymer with the cationic lipid and the nucleic acid form a complex, and the composition comprises a lipid membrane which encapsulates the complex.

8. The composition according to claim 5, wherein the nucleic acid is a nucleic acid which has an activity of suppressing the expression of a target gene by utilizing RNA interference (RNAi).

9. The composition according to claim 8, wherein the target gene is a gene which is expressed in the liver, lung, kidney, or spleen.

10. A pharmaceutical composition for use in the treatment of a disease, comprising the composition according to claim 8.

11. The pharmaceutical composition according to claim 10, which is for intravenous administration.

12. The pharmaceutical composition according to claim 10, wherein the disease is associated with the liver, lung, kidney, or spleen.

* * * * *